US006333153B1

(12) United States Patent
Fishel et al.

(10) Patent No.: US 6,333,153 B1
(45) Date of Patent: Dec. 25, 2001

(54) COMPOSITIONS, KITS, AND METHODS FOR EFFECTING ADENINE NUCLEOTIDE MODULATION OF DNA MISMATCH RECOGNITION PROTEINS

(75) Inventors: Richard A. Fishel, Penn Valley; Scott Gradia; Samir Acharya, both of Philadelphia, all of PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/143,571

(22) Filed: Aug. 28, 1998

Related U.S. Application Data

(60) Provisional application No. 60/093,935, filed on Jul. 23, 1998, provisional application No. 60/066,977, filed on Nov. 28, 1997, and provisional application No. 60/057,136, filed on Aug. 28, 1997.

(51) Int. Cl.[7] .......... C12Q 1/68; G01N 33/53; C12P 19/34; C07K 14/00; C07H 21/04

(52) U.S. Cl. .......... 435/6; 435/7.1; 435/91.2; 530/350; 536/23.1

(58) Field of Search .......... 435/6, 91.2, 7.1, 435/810; 530/350; 536/23.1

(56) References Cited

U.S. PATENT DOCUMENTS 5,556,750 9/1996 Modrich .......... 435/6

FOREIGN PATENT DOCUMENTS

WO 96/41192 7/1996 (WO) .

OTHER PUBLICATIONS

Acharya et al., 1996, Proc. Natl. Acad. Sci. USA 93:13629–13634.
Adams et al., 1991, Science 252:1651–1656.
Alani et al., 1997, Mol. Cell Biol. 1 7: 2436–2447.
Alani et al., 1995, Genes & Dev. 9:234–247.
Alberts, 1998, Cell 92:291–294.
Allen et al., 1997, EMBO J. 16:4467–4476.
Apte et al., 1993, BioTechniques 15:890–893.
Au et al., 1992, J. Biol. Chem. 267:12142–12148.
Baker et al., 1990, Science 249:912–915.
Biswas et al., 1997, J. Biol. Chem. 272: 13355–13364.
Blyth et al., 1995, Oncogene 10:1717–1723.
Bokoch et al., 1993, FASEB J. 7:750–759.
Bronner et al., 1994, Nature 368:258–261.
Burns et al., 1994, Genes Dev. 8:1087–1105.
Campbell and Kleckner, 1990, Cell 62:967–979.
Chi et al., 1994, J. Biol. Chem. 269:29984–29997.
Cooper et al., 1993, J. Biol. Chem. 268:11823–11829.
de Wind et al., 1995, Cell 82:321–330.
Demerec et al., 1957, Bact. Genet., Carnegie Inst. Wash. Yearbook 370:390–406.
Dickson and Hafen, 1994, Curr. Opinion in Gen. and Dev. 4:64–70.

(List continued on next page.)

*Primary Examiner*—Stephanie W. Zitomer
(74) *Attorney, Agent, or Firm*—Akin, Gump, Strauss, Hauer & Feld, L.L.P.

(57) ABSTRACT

Compositions, and products comprising a MutS homolog which binds to a mismatched region of a duplex DNA molecule in the presence of ADP are provided, as are methods of binding MutS homologs to mismatched DNA in the presence of ADP. The use of MutL homolog derivatives in combination with MutS homologs is also included. Non-human mammals which are nullizygous for both Msh2 and p53 are also provided, as are methods of making and using the same.

88 Claims, 25 Drawing Sheets

OTHER PUBLICATIONS

Diller et al., 1990, Mol. Cell. Biol. 10:5772–5781.
Dohlman and Thorner, 1997, J. Biol. Chem. 272:3871–3874.
Donehower et al., 1995, Genes Dev. 9:882–895.
Donehower et al., 1992, Nature 356:215–221.
Drummond et al., 1995, Science 268:1909–1912.
Fang et al., 1993, J. Biol. Chem. 268:11838–11844.
Fearon et al., 1990, Cell 61:759–767.
Fishel et al., 1997, Curr. Opin. Genet. Dev. 7:105–113.
Fishel et al., 1994, Science 266:1403–1405.
Fishel et al., 1994, Cancer Res. 54:5539–5542.
Fishel et al., 1993, Cell 75:1027–1038.
Fishel et al., 1988, Proc. Natl. Acad. Sci. USA 85:36–40.
Fishel et al., 1983, UCLA Symp. Mol. Cell. Biol. New Series 11:309–324.
Fishel et al., 1986, J. Mol. Biol. 188:147–157.
Fujii and Shimada, 1989, J. Biol. Chem. 264:10057–10064.
Glazer et al., 1987, Mol. Cell. Biol., 7:218–224.
Gradia et al., 1997, Cell 91:995–1005.
Grilley et al., 1990, Mutat. Res. 236:253–267.
Grilley et al., 1989, J. Biol. Chem. 264:1000–1004.
Grilley et al., 1993, J. Biol. Chem. 268:11830–11837.
Haber et al., 1988, J. Bacteriol. 170:197–202.
Haber et al., 1991, EMBO. J. 10:2707–2715.
Harris et al., 1998, J. Bacteriol. 180:989–993.
Hawn et al., 1995, Cancer Res. 55:3721–3725.
Hill, 1970, Mutat. Res. 9:341–344.
Holliday, 1964, Genet. Res. 5:282–304.
Hollingsworth et al., 1995, Genes Dev. 9:1728–1739.
Holmes et al., 1990, Proc. Natl. Acad. Sci. USA 87:5837–5841.
Hudson et al., 1995, Science 270:1945–1954.
Hughes et al., 1992, J. Biol. Chem. 267:23876–23882.
Jacks et al., 1994, Curr. Biol. 4:1–7.
Johnson et al., 1996, J. Biol. Chem. 271:7285–7288.
Kallal et al., 1997, Mol. Cell. Biol. 17:2897–2907.
Kastan et al., 1992, Cell 71:587–597.
Kolodner, 1996, Genes Dev. 10:1433–1442.
Kramer et al., 1989, J. Bacteriol. 171:5339–5346.
Laalami et al., 1996, Biochimie 78:577–589.
Lahue et al., 1989, Science 245:160–164.
Lahue et al., 1987, Proc. Natl. Acad. Sci. USA 84:1482–1486.
Li et al., 1995, Proc. Natl. Acad., Sci. USA 92: 1950–1954.
Lin et al., 1992, Proc. Natl. Acad. Sci. USA 89:9210–9214.
Linton et al., 1989, Mol. Cell. Biol. 9:3058–3072.
Loeb, 1991, Cancer Res. 51:3075–3079.
Longley et al., 1997, J. Biol. Chem. 272: 10917–10921.
Lu et al., 1983, Proc. Natl. Acad. Sci. USA 80:4639–4643.
Lukkarinen et al., 1997, Stroke 28:639–645.
Lyon, 1961, Nature 190:372–373.
Maegley et al., 1996, Proc. Natl. Acad. Sci. USA 93:8160–8166.
Mankovich et al., 1989, J. Bacteriol. 171:5325–5331.
Marra et al., 1996, Oncogene 13:2189–2196.
Marsischky et al., 1996, Genes Dev. 10:407–420.
Mederna et al., 1993, Crit. Rev. Oncol. 4:615–661.
Mello et al., 1996, Chemistry & Biology 3:579–589.
Meyers et al., 1997, Cancer Res. 57:206–208.
Miller et al., 1976, Proc. Natl. Acad. Sci. USA 73:3073–3077.
Miret et al., 1993, J. Biol. Chem. 268:3507–3513.
Miret et al., 1996, Nuc. Acids Res. 24:721–729.
Miyake, 1960, Genetics 45:755–762.
Modrich, 1989, J. Biol. Chem. 264:6597–6600.
Modrich, 1991, Annu. Rev. Genet. 25:229–253.
Modrich, 1987, Ann. Rev. Biochem. 56:435–466.
Modrich, 1997, J. Biol. Chem. 272:24727–24730.
Modrich 1986, Basic Life Sci. 38:303–310.
Modrich and Lahue, 1996, Annu. Rev. Biochem. 65:101–133.
Nacht et al., 1996, Genes Dev. 10:2055–2066.
New et al., 1993, Mol. Gen. Genet. 239:97–108.
Nicolaides et al., 1994, Nature 371:75–80.
Nicol et al., 1995, Nature Genet. 10:181–187.
Palmiter et al., 1986, Ann. Rev. Genet. 20:465–499.
Palombo et al., 1995, Science 268:1912–1914.
Palombo et al., 1996, Curr. Biol. 6:1181–1184.
Papadopoulos et al., 1995, Science 268:1915–1917.
Parmeggiani et al., 1981, Mol. Cell. Biochem. 35:129–158.
Prolla et al., 1994, Science 265:1091–1093.
Prolla et al., 1994, Mol. Cell. Biol. 14:407–415.
Purdie et al., 1994, Oncogene 9:603–609.
Quilliam et al., 1995, Bioessays 17:395–404.
Rastan, 1994, Curr. Opin. Genet. Dev. 4:292–297.
Reenan et al., 1992, Genetics 132:963–973.
Reitmair et al., 1995, Nature Genet. 11:64–70.
Risinger et al., 1996, Nature Genet. 14:102–105.
Rogel et al., 1985, Mol. Cell. Biol. 5:2851–2855.
Sah et al., 1995, Nature Genet. 10:175–180.
Sekimizu et al., 1987, Cell 50:259–265.
Siegel et al., 1967, J. Bacteriol. 94:38–47.
Smith et al., 1990, Mol. Cell. Biol. 10:6003–6012.
Song et al., 1994, Biophys. J. 67:91–104.
Spiegel, 1987, Mol. Cell. Endocrinol. 49:1–16.
Strand et al., 1995, Proc. Natl. Acad. Sci. USA 92:10418–10421.
Strasser et al., 1994, Cell 329–339.
Su et al., 1986, Proc. Natl. Acad. Sci. USA 83:5057–5061.
Su et al., 1988, J. Biol. Chem. 263:6829–6835.
Su et al., 1989, Genome 31:104–111.
Tagaki, 1974, Exp. Cell. Res. 86:127–135.
Taylor, 1960, J. Biophys. Biochem. Cytol. 7:455–464.
Theiler, 1972, In: *The House Mouse Development and Normal Stages from Fertilization to 4 Weeks of Age,* Springer–Verlag, New York, p. 168.
Thomas et al., 1991, J. Biol. Chem. 266:3744–3751.
Tocque et al., 1997, Cell Signal. 9:153–158.
Trahey and McCormick, 1987, Science 238:542–545.
Trahey et al., 1987, Mol. Cell. Biol. 7:541–544.
Varlet et al., 1994, Nucl. Acids Res. 22:5723–5728.
Walker et al., 1982, EMBO J. 1:945–951.
Welsh et al., 1987, J. Biol. Chem. 262:15624–15629.
Wiesmuller et al., 1994, Cell Signal. 6:247–267.
Williams et al., 1994, Cold Spring Harbor Symp. Quant. Biol. 59:449–457.
Wilson et al., 1995, Cancer Res. 55:5146–5150.
Wu et al., 1994, J. Bacteriol 176:5393–5400.
Yu et al., 1992, J. Mol. Biol. 225:193–216.

Fig. 8A

CCTGGTACCT CGAGCGATCA AGCTTGGTGG AATTCGCCG

Fig. 8B

CCTGGTACCT CGAGCGATCG AGCTTGGTGG AATTCGCCG

Fig. 8C

ACTATAGGGC GAATTGGGTA CCGCTGAATT GCACCGAGCT CGATCCTCGA
TGATCCTAAG CTAAGCTTCA GCTCCAGCTT T

Fig. 8D

ACTATAGGGC GAATTGGGTA CCGCTGAATT GCACCGAGCT TGATCCTCGA
TGATCCTAAG CTAAGCTTCA GCTCCAGCTT T

```
  1                     CAGAAACCTCATACTTCTCGGGTCAGGGAAGGTTTGGAGGGC
 44 GTGGCGGTCGGTCAGCGGGGCGTTCTCCCACCTGTAGCGACTCAGAGCCTCCAAGCTC

  1 Met Ala Ser Leu Gly Ala Asn Pro Arg Arg Thr Pro Gln Gly Pro
102 ATG GCC TCC TTA GGA GCG AAC CCA AGG AGG ACA CCG CAG GGA CCG

 16 Arg Pro Gly Ala Ala Ser Ser Gly Phe Pro Ser Pro Ala Pro Val
147 AGA CCT GGG GCG GCC TCC TCC GGC TTC CCC AGC CCG GCC CCA GTG

 31 Pro Gly Pro Arg Glu Ala Glu Glu Glu Glu Val Glu Glu Glu Glu
192 CCG GGC CCC AGG GAG GCC GAG GAG GAG GAA GTC GAG GAG GAG GAG

 46 Glu Leu Ala Glu Ile His Leu Cys Val Leu Trp Asn Ser Gly Tyr
237 GAG CTG GCC GAG ATC CAT CTG TGT GTG CTG TGG AAT TCA GGA TAC

 61 Leu Gly Ile Ala Tyr Tyr Asp Thr Ser Asp Ser Thr Ile His Phe
282 TTG GGC ATT GCC TAC TAT GAT ACT AGT GAC TCC ACT ATC CAC TTC

 76 Met Pro Asp Ala Pro Asp His Glu Ser Leu Lys Leu Leu Gln Arg
327 ATG CCA GAT GCC CCA GAC CAC GAG AGC CTC AAG CTT CTC CAG AGA

 91 Val Leu Asp Glu Ile Asn Pro Gln Ser Val Val Thr Ser Ala Lys
372 GTT CTG GAT GAG ATC AAT CCC CAG TCT GTT GTT ACG AGT GCC AAA

106 Gln Asp Glu Asn Met Thr Arg Phe Leu Gly Lys Leu Ala Ser Gln
417 CAG GAT GAG AAT ATG ACT CGA TTT CTG GGA AAG CTT GCC TCC CAG
```

Fig. 19A

```
121 Glu His Arg Glu Pro Lys Arg Pro Glu Ile Ile Phe Leu Pro Ser
462 GAG CAC AGA GAG CCT AAA AGA CCT GAA ATC ATA TTT TTG CCA AGT

136 Val Asp Phe Gly Leu Glu Ile Ser Lys Gln Arg Leu Leu Ser Gly
507 GTG GAT TTT GGT CTG GAG ATA AGC AAA CAA CGC CTC CTT TCT GGA

151 Asn Tyr Ser Phe Ile Pro Asp Ala Met Thr Ala Thr Glu Lys Ile
552 AAC TAC TCC TTC ATC CCA GAC GCC ATG ACT GCC ACT GAG AAA ATC

166 Leu Phe Leu Ser Ser Ile Ile Pro Phe Asp Cys Leu Leu Thr Val
597 CTC TTC CTC TCT TCC ATT ATT CCC TTT GAC TGC CTC CTC ACA GTT

181 Arg Ala Leu Gly Gly Leu Leu Lys Phe Leu Gly Arg Arg Arg Ile
642 CGA GCA CTT GGA GGG CTG CTG AAG TTC CTG GGT CGA AGA AGA ATC

196 Gly Val Glu Leu Glu Asp Tyr Asn Val Ser Val Pro Ile Leu Gly
687 GGG GTT GAA CTG GAA GAC TAT AAT GTC AGC GTC CCC ATC CTG GGC

211 Phe Lys Lys Phe Met Leu Thr His Leu Val Asn Ile Asp Gln Asp
732 TTT AAG AAA TTT ATG TTG ACT CAT CTG GTG AAC ATA GAT CAA GAC

226 Thr Tyr Ser Val Leu Gln Ile Phe Lys Ser Glu Ser His Pro Ser
777 ACT TAC AGT GTT CTA CAG ATT TTT AAG AGT GAG TCT CAC CCC TCA

241 Val Tyr Lys Val Ala Ser Gly Leu Lys Glu Gly Leu Ser Leu Phe
822 GTG TAC AAA GTG GCC AGT GGA CTG AAG GAG GGG CTC AGC CTC TTT
```

Fig. 19B

```
 256Gly Ile Leu Asn Arg Cys His Cys Lys Trp Gly Glu Lys Leu Leu
 867 GGA ATC CTC AAC AGA TGC CAC TGT AAG TGG GGA GAG AAG CTG CTC

 271 Arg Leu Trp Phe Thr Arg Pro Thr His Asp Leu Gly Glu Leu Ser
 912 AGG CTA TGG TTC ACA CGT CCG ACT CAT GAC CTG GGG GAG CTC AGT

 286 Ser Arg Leu Asp Val Ile Gln Phe Phe Leu Leu Pro Gln Asn Leu
 957 TCT CGT CTG GAC GTC ATT CAG TTT TTT CTG CTG CCC CAG AAT CTG

 301 Asp Met Ala Gln Met Leu His Arg Leu Leu Gly His Ile Lys Asn
1002 GAC ATG GCT CAG ATG CTG CAT CGG CTC CTG GGT CAC ATC AAG AAC

 316 Val Pro Leu Ile Leu Lys Arg Met Lys Leu Ser His Thr Lys Val
1047 GTG CCT CTG ATT CTG AAA CGC ATG AAG TTG TCC CAC ACC AAG GTC

 331 Ser Asp Trp Gln Val Leu Tyr Lys Thr Val Tyr Ser Ala Leu Gly
1092 AGC GAC TGG CAG GTT CTC TAC AAG ACT GTG TAC AGT GCC CTG GGC

 346 Leu Arg Asp Ala Cys Arg Ser Leu Pro Gln Ser Ile Gln Leu Phe
1137 CTG AGG GAT GCC TGC CGC TCC CTG CCG CAG TCC ATC CAG CTC TTT

 361 Arg Asp Ile Ala Gln Glu Phe Ser Asp Asp Leu His His Ile Ala
1182 CGG GAC ATT GCC CAA GAG TTC TCT GAT GAC CTG CAC CAT ATC GCC

 376 Ser Leu Ile Gly Lys Val Val Asp Phe Glu Gly Ser Leu Ala Glu
1227 AGC CTC ATT GGG AAA GTA GTG GAC TTT GAG GGC AGC CTT GCT GAA
```

Fig. 19C

```
 391 Asn Arg Phe Thr Val Leu Pro Asn Ile Asp Pro Glu Ile Asp Glu
1272 AAT CGC TTC ACA GTC CTC CCC AAC ATA GAT CCT GAA ATT GAT GAG

 406 Lys Lys Arg Arg Leu Met Gly Leu Pro Ser Phe Leu Thr Glu Val
1317 AAA AAG CGA AGA CTG ATG GGA CTT CCC AGT TTC CTT ACT GAG GTT

 421 Ala Arg Lys Glu Leu Glu Asn Leu Asp Ser Arg Ile Pro Ser Cys
1362 GCC CGC AAG GAG CTG GAG AAT CTG GAC TCC CGT ATT CCT TCA TGC

 436 Ser Val Ile Tyr Ile Pro Leu Ile Gly Phe Leu Leu Ser Ile Pro
1407 AGT GTC ATC TAC ATC CCT CTG ATT GGC TTC CTT CTT TCT ATT CCC

 451 Arg Leu Pro Ser Met Val Glu Ala Ser Asp Phe Glu Ile Asn Gly
1452 CGC CTG CCT TCC ATG GTA GAG GCC AGT GAC TTT GAG ATT AAT GGA

 466 Leu Asp Phe Met Phe Leu Ser Glu Glu Lys Leu His Tyr Arg Ser
1497 CTG GAC TTC ATG TTT CTC TCA GAG GAG AAG CTG CAC TAT CGT AGT

 481 Ala Arg Thr Lys Glu Leu Asp Ala Leu Leu Gly Asp Leu His Cys
1542 GCC CGA ACC AAG GAG CTG GAT GCA TTG CTG GGG GAC CTG CAC TGC

 496 Glu Ile Arg Asp Gln Glu Thr Leu Leu Met Tyr Gln Leu Gln Cys
1587 GAG ATC CGG GAC CAG GAG ACG CTG CTG ATG TAC CAG CTA CAG TGC

 511 Gln Val Leu Ala Arg Ala Ala Val Leu Thr Arg Val Leu Asp Leu
1632 CAG GTG CTG GCA CGA GCA GCT GTC TTA ACC CGA GTA TTG GAC CTT
```

Fig. 19D

526 Ala Ser Arg Leu Asp Val Leu Leu Ala Leu Ala Ser Ala Ala Arg

1677 GCC TCC CGC CTG GAC GTC CTG CTG GCT CTT GCC AGT GCT GCC CGG

541 Asp Tyr Gly Tyr Ser Arg Pro Arg Tyr Ser Pro Gln Val Leu Gly

1722 GAC TAT GGC TAC TCA AGG CCG CGT TAC TCC CCA CAA GTC CTT GGG

556 Val Arg Ile Gln Asn Gly Arg His Pro Leu Met Glu Leu Cys Ala

1767 GTA CGA ATC CAG AAT GGC AGA CAT CCT CTG ATG GAA CTC TGT GCC

571 Arg Thr Phe Val Pro Asn Ser Thr Glu Cys Gly Gly Asp Lys Gly

1812 CGA ACC TTT GTG CCC AAC TCC ACA GAA TGT GGT GGG GAC AAA GGG

586 Arg Val Lys Val Ile Thr Gly Pro Asn Ser Ser Gly Lys Ser Ile

1857 AGG GTC AAA GTC ATC ACT GGA CCC AAC TCA TCA GGG AAG AGC ATA

601 Tyr Leu Lys Gln Val Gly Leu Ile Thr Phe Met Ala Leu Val Gly

1902 TAC CTC AAA CAG GTA GGC TTG ATC ACA TTC ATG GCC CTG GTA GGC

616 Ser Phe Val Pro Ala Glu Glu Ala Glu Ile Gly Ala Val Asp Ala

1947 AGC TTT GTG CCA GCA GAG GAG GCC GAA ATT GGG GCA GTA GAC GCC

631 Ile Phe Thr Arg Ile His Ser Cys Glu Ser Ile Ser Leu Gly Leu

1992 ATC TTC ACA CGA ATT CAT AGC TGC GAA TCC ATC TCC CTT GGC CTC

646 Ser Thr Phe Met Ile Asp Leu Asn Gln Val Ala Lys Ala Val Asn

2037 TCC ACC TTC ATG ATC GAC CTC AAC CAG GTG GCG AAA GCA GTG AAC

Fig. 19E

```
 661 Asn Ala Thr Ala Gln Ser Leu Val Leu Ile Asp Glu Phe Gly Lys
2082 AAT GCC ACT GCA CAG TCG CTG GTC CTT ATT GAT GAA TTT GGA AAG

 676 Gly Thr Asn Thr Val Asp Gly Leu Ala Leu Leu Ala Ala Val Leu
2127 GGA ACC AAC ACG GTG GAT GGG CTC GCG CTT CTG GCC GCT GTG CTC

 691 Arg His Trp Leu Ala Arg Gly Pro Thr Cys Pro His Ile Phe Val
2172 CGA CAC TGG CTG GCA CGT GGA CCC ACA TGC CCC CAC ATC TTT GTG

706 Ala Thr Asn Phe Leu Ser Leu Val Gln Leu Gln Leu Leu Pro Gln
2217 GCC ACC AAC TTT CTG AGC CTT GTT CAG CTA CAA CTG CTG CCA CAA

 721 Gly Pro Leu Val Gln Tyr Leu Thr Met Glu Thr Cys Glu Asp Gly
2262 GGG CCC CTG GTG CAG TAT TTG ACC ATG GAG ACC TGT GAG GAT GGC

 736 Asn Asp Leu Val Phe Phe Tyr Gln Val Cys Glu Gly Val Ala Lys
2307 AAC GAT CTT GTC TTC TTC TAT CAG GTT TGC GAA GGT GTT GCG AAG

 751 Ala Ser His Ala Ser His Thr Ala Ala Gln Ala Gly Leu Pro Asp
2352 GCC AGC CAT GCC TCC CAC ACA GCT GCC CAG GCT GGG CTT CCT GAC

 766 Lys Leu Val Ala Arg Gly Lys Glu Val Ser Asp Leu Ile Arg Ser
2397 AAG CTT GTG GCT CGT GGC AAG GAG GTC TCA GAC TTG ATC CGC AGT

 781 Gly Lys Pro Ile Lys Pro Val Lys Asp Leu Leu Lys Lys Asn Gln
2442 GGA AAA CCC ATC AAG CCT GTC AAG GAT TTG CTA AAG AAG AAC CAA
```

Fig. 19F

```
 796 Met Glu Asn Cys Gln Thr Leu Val Asp Lys Phe Met Lys Leu Asp
2487 ATG GAA AAT TGC CAG ACA TTA GTG GAT AAG TTT ATG AAA CTG GAT

 811 Leu Glu Asp Pro Asn Leu Asp Leu Asn Val Phe Met Ser Gln Glu
2532 TTG GAA GAT CCT AAC CTG GAC TTG AAC GTT TTC ATG AGC CAG GAA

 826 Val Leu Pro Ala Ala Thr Ser Ile Leu Stop
2577 GTG CTG CCT GCT GCC ACC AGC ATC CTC TGA GAGTCCTTCCAGTGTCCTC

2626 CCCAGCCTCCTGAGACTCCGGTGGCTGCCATGCCCTCTTTGTTTCCTTATCTCCCTCA
2686 GACGCAGAGTTTTTAGTTTCTCACAATTCTAATGTAATAATATATCTTAA
```

Fig. 19G

COMPOSITIONS, KITS, AND METHODS FOR EFFECTING ADENINE NUCLEOTIDE MODULATION OF DNA MISMATCH RECOGNITION PROTEINS

CROSS REFERENCE TO RELATED APPLICATIONS

This application is entitled to priority pursuant to 35 U.S.C. §119(e) to U.S. Provisional Application No. 60/093,935, filed Jul. 23, 1998, to U.S. Provisional Application No. 60/066,977, filed Nov. 28, 1997, and to U.S. Provisional Application No. 60/057,136, filed Aug. 28, 1997. +gi

GOVERNMENT SUPPORT

This research was supported in part by U.S. Government finds (NIH grants numbers CA56542 and CA67007 and NRSA grant CA73134), and the U.S. Government may therefore have certain rights in the invention.

FIELD OF THE INVENTION

The field of the invention is DNA mismatch protein binding, including animals useful as models for tumorigenesis, apoptosis, and aging.

BACKGROUND OF THE INVENTION

DNA Mismatch Repair

The most widely accepted model for DNA post-replication mismatch repair is based largely on the model of the DNA adenine methylation (Dam)-Instructed pathway of *Escherichia coli* proposed by Modrich (1986, Basic Life Sci. 38:303–310; Modrich, 1987, Ann. Rev. Biochem. 56:435–466; Modrich, 1989, J. Biol. Chem. 264:6597–6600; Modrich, 1991, Annu. Rev. Genet. 25:229–253; Modrich et al., 1996, Annu. Rev. Biochem. 65:101–133). According to this model, the MutS protein recognizes and binds mismatched nucleotides resulting from polymerase misincorporation errors to form a MutS-DNA product (Su et al., 1986, Proc. Natl. Acad. Sci., USA 83:5057–5061; Su et al., 1988, J. Biol. Chem. 263:6829–6835). MutS mismatch binding is followed by the interaction of MutL protein with the MutS-DNA product (Grilley et al., 1990, Mutat. Res. 236:253–267), which accelerates ATP-dependent translocation of the MutS-MutL complex (Allen et al., 1997, EMBO J. 16:4467–4476) to a hemimethylated GATC Dam site to which MutH protein is bound (Welsh et al., 1987, J. Biol. Chem. 262:15624–15629; Au et al., 1992, J. Biol. Chem. 267:12142–12148). The MutS-MutL complex stimulates an intrinsic endonuclease activity of MutH protein, which cleaves the non-methylated (i.e. more recently replicated) DNA strand (Welsh et al., 1987, J. Biol. Chem. 262:15624–15629; Lahue et al., 1987, Proc. Natl. Acad. Sci. USA 84:1482–1486; Su et al., 1989, Genome 31:104–111; Cooper et al., 1993, J. Biol. Chem. 268:11823–11829; Grilley et al., 1993, J. Biol. Chem. 268:11830–11837). Strand cleavage enables one of three single-stranded exonucleases of *E. coli* (RecJ, ExoI, ExoVII) to degrade the non-methylated strand, which can then be re-synthesized by the *E. coli* PolIII holoenzyme complex (Lahue et al., 1989, Science 245:160–164). The net result is a strand-specific mismatch repair event.

Many genetic studies performed using *E. coli* support this interpretation. For example bacteria having a mutated mutH, mutL, or mutS gene exhibit a mutator phenotype that is presumed to be the result of the increased probability of misincorporation errors leading to mutations (Demerec et al., 1957, Bact. Genet., Carnegie Inst. Wash. Yearbook 370:390–406; Miyake, 1960, Genetics 45:755–762; Siegel et al., 1967, J. Bacteriol. 94:38–47; Hill, 1970, Mutat. Res. 9:341–344). However, not all predictions arising from the *E. coli* Dam-instructed model agree with experimental results. For example, bacteria having a mutation in each of the recJ, exoI, and exo VII genes do not exhibit a mutator phenotype, suggesting that other exonuclease(s) or mechanism(s) are involved in the mismatch repair process.

Homologs of the procaryotic MutS and MutL proteins have been identified in eukaryotes (Fishel et al., 1993, Cell 75:1027–1038; Prolla et al., 1994, Science 265:1091–1093; Bronner et al., 1994, Nature 368:258–261). MutH analogs appear to exist only in gram-negative bacteria.

Multiple MutS and MutL homologs have been identified in yeast and human cells which individually participate in such diverse activities as nuclear and organelle mismatch repair as well as distinct meiotic functions (Fishel et al., 1997, Curr. Opin. Genet. Dev. 7:105–113). Germ-line mutations of the human MutS and MutL Homologs, hMSH2, hMLH1, and hPMS2, have been found to be associated with the common cancer predisposition syndrome, hereditary non-polyposis colorectal cancer (HNPCC; Bronner et al., 1994, Nature 368:258–261; Fishel et al., 1993, Cell 75:1027–1038). Yeast and human MutS and MutL homologs exist primarily as heterodimeric proteins. Yeast MSH2 protein has been found to be associated with MSH3 or MSH6, and yeast MLH1 has been found to be associated with PMS1. Human hMSH2 protein has been found to be associated with hMSH3 or hMSH6 (also designated GTBP or p160 by some authors), and human hMLH1 has been found to be associated with hPMS2 (Li et al., 1995, Proc. Natl. Acad., Sci. USA 92:1950–1954; Prolla et al., 1994, Science 265:1091–1093; Drummond et al., 1995, Science 268:1909–1912; Marsischky et al., 1996, Gen. Dev. 10:407–420; Acharya et al., 1996, Proc. Natl. Acad. Sci. USA 93:13629–13634). Furthermore, MSH2/MSH3 and MSH2/MSH6 protein complexes appear to possess overlapping and redundant mismatch binding activities (Acharya et al., 1996, Proc. Natl. Acad. Sci. USA 93:13629–13634; Risinger et al., 1996, Nature Genet. 14:102–105).

Classification of MutS and MutL homologs is based on the presence in the proteins of highly conserved regions of amino acid identity. The most highly conserved region among MutS homologs includes approximately 150 amino acids which comprise a helix-turn-helix domain associated with a Walker A adenine-nucleotide and magnesium binding motif (Walker et al., 1982, EMBO J. 1:945–951). This adenine nucleotide binding domain constitutes more than 80% of the identifiable homology between MutS homologs (Fishel et al., 1997, Curr. Opin. Genet. Dev. 7:105–113). Both purified bacterial MutS homologs and purified yeast MutS homologs possess an intrinsic low-level ATPase activity (Haber et al., 1991, EMBO. J. 10:2707–2715; Chi et al., 1994, J. Biol. Chem. 269: 29993–29997; Chi et al., 1994, J. Biol. Chem. 269:29984–29992; Alani et al., 1997, Mol. Cell Biol. 17: 2436–2447). This ATPase activity is likely to be important for the function of MutS homologs, as indicated by the fact that mutation of conserved amino acid residues in the adenine nucleotide binding domain results in a dominant mutator phenotype in both bacteria and yeast (Haber et al., 1991, EMBO. J. 10:2707–2715; Wu et al., 1994, J. Bacteriol 176:5393–5400; Alani et al., 1997, Mol. Cell Biol. 17: 2436–2447). A central role for the adenine nucleotide binding domain is consistent with the ATP-dependent translocation model of mismatch repair proposed by Modrich and colleagues (Allen et al., 1997, EMBO J. 16:4467–4476).

Genetic and biochemical studies of the human mismatch repair process indicate that it is similar to bacterial mismatch repair, except that the physiologically relevant mechanism for directing strand specificity is unknown (Miller et al., 1976, Proc. Natl. Acad. Sci. USA 73:3073–3077; Glazer et al., 1987, Mol. Cell. Biol., 7:218–224; Holmes et al., 1990, Proc. Natl. Acad. Sci. USA 87:5837–5841; Thomas et al., 1991, J. Biol. Chem. 266:3744–3751; Fang et al., 1993, J. Biol. Chem. 268:11838–11844; Longley et al., 1997, J. Biol. Chem. 272:10917–10921). Purified hMSH2 protein binds mismatched nucleotides and DNA lesions (Fishel et al., 1994, Science 266:1403–1405; Fishel et al., 1994, Cancer Res. 54:5539–5542; Mello et al., 1996, Chemistry & Biology 3:579–589), and the specificity and affinity of that recognition is enhanced by association of hMSH2 with hMSH3 or hMSH6 (Drummond et al., 1995; Acharya et al., 1996, Proc. Natl. Acad. Sci. USA 93:13629–13634; Palombo et al., 1996, Curr. Biol. 6:1181–1184).

Although the ability of MutS homologs to bind to mismatched duplex DNA has been recognized (e.g. U.S. Pat. No. 5,556,750), methods of using MutS homologs in vitro have been limited by a lack of understanding regarding the properties of such homologs. A need remains for methods of binding MutS homologs and mismatched duplex DNA, which methods take advantages of the biochemical properties of such homologs.

Transgenic and Nullizygous Animals

The development of transgenic animals and nullizygous animal models has provided important new avenues for the study of specific gene functions in differentiation, embryogenesis and neoplastic development (Palmiter et al., 1986, Ann. Rev. Genet. 20:465–499). Transgenic animals frequently serve as model systems for the study of various disease states and also provide an experimental system in which to test compounds for their ability to regulate disease. Nullizygous animals are similarly useful as experimental systems for the testing of compounds useful for diagnosis, treatment, or both, of disease.

Lukkarinen et al. (1997, Stroke 28:639–645) teaches that gene constructs which enable the generation of transgenic mice also enable the generation of other transgenic rodents, including rats. Similarly, nullizygous mutations in a genetic locus of an animal of one species can be replicated in an animal of another species having a genetic locus highly homologous to the first species. For example, many genetic loci are highly homologous among mammals, and even more highly homologous among subgroups of mammals, such as among rodents.

The mutator hypothesis of tumorigenesis suggests that loss in an organism of a chromosomal stability function, a chromosomal maintenance function, or both, results in an elevated mutation rate in the organism. An elevated mutation rate hastens accumulation of the numerous mutations required for multistep carcinogenesis (Loeb, 1991, Cancer Res. 51:3075–3079).

Loss of the function of p53 protein has been proposed to increase cellular hypermutability in an organism, thereby accelerating tumorigenesis, although a clear role for p53 protein in genomic instability remains controversial (Kastan et al., 1992, Cell 71:587–597; Fishel et al., 1997, Curr. Opin. Genet. Dev. 7:105–113). p53, the gene encoding p53 protein, is frequently mutated in a wide range of human cancers including, but not limited to, colonic tumors (Fearon et al., 1990, Cell 61:759–767). Transgenic mice nullizygous for p53 are viable and susceptible to tumorigenesis (de Wind et al., 1995, Cell 82:321–330; Reitmair et al., 1995, Nature Genet. 11:64–70; Donehower et al., 1992, Nature 356:215–221; Jacks et al., 1994, Curr. Biol. 4:1–7; Purdie et al., 1994, Oncogene 9:603–609).

Although nullizygous p53 mice can be used as models of carcinogenesis, the rates at which such mice develop tumors can be slower than what is desirable, particularly for large-scale screening studies involving numerous potential anti-cancer therapeutic or prophylactic compositions. What is needed is a transgenic mouse which, when exposed to a carcinogen, succumbs to tumorigenesis caused by the carcinogen more readily than does a nullizygous p53 mouse and which, even when not exposed to an identifiable carcinogen, succumbs to tumors more readily than does a nullizygous p53 mouse.

Critical unmet needs also exist for animal models of programmed cell death (apoptosis) and of aging.

The present invention satisfies the needs identified above.

SUMMARY OF THE INVENTION

The invention relates to a method of modifying a mismatched duplex DNA. The method comprises contacting an MSH dimer and the mismatched duplex DNA in the presence of a binding solution. In one embodiment, the binding solution comprising a nucleotide selected from the group consisting of ADP and ATP, and the concentration of ATP in the binding solution is less than about 3 micromolar. The MSH dimer thereby associates with the mismatched region of the mismatched duplex DNA, and the mismatched duplex DNA is modified. In one embodiment, the MSH dimer is selected from the group consisting of a prokaryotic MSH homodimer, a prokaryotic MSH heterodimer, a eukaryotic MSH homodimer, and a eukaryotic MSH heterodimer. The MSH dimer may, for example, be a homodimer of a MutS homolog selected from the group consisting of a human MutS homolog, a murine MutS homolog, a rat MutS homolog, a Drosophila MutS homolog, a yeast MutS homolog, and a *Saccharomyces cerevisiae* MutS homolog. An example of a eukaryotic MSH homodimer is an MSH2 homodimer. The eukaryotic MSH heterodimer useful in this method comprises MutS homologs independently selected from the group consisting of an MSH2 protein, an MSH3 protein, an MSH4 protein, an MSH5 protein, and an MSH6 protein. By way of example, the MSH dimer may be selected from the group consisting of an MSH2:MSH3 heterodimer, an MSH2:MSH6 heterodimer, and an MSH4:MSH5 heterodimer. In another embodiment of this method, the prokaryotic MSH dimer is a homodimer of *Escherichia coli* MutS. Preferably, the MSH dimer is substantially purified.

According to this method, the concentration of ATP in the binding solution is preferably less than about 0.3 micromolar, or, more preferably, the binding solution is substantially free of ATP. In another embodiment of this method, at least one of the MSH dimer and the mismatched duplex DNA is bound to a support. In yet another embodiment, the mismatched duplex DNA has at least one free end. In still another embodiment, the mismatched duplex DNA comprises a DNA strand generated by reverse transcription of mRNA obtained from an organism.

According to one aspect of this method, the mismatched duplex DNA comprises a first DNA strand having a reference nucleotide sequence and a second DNA strand. The second strand may, for example, be selected from the group consisting of a DNA strand obtained from an organism, a DNA strand obtained by amplification of at least a portion of a polynucleotide obtained from an organism, a DNA strand obtained by cleavage of a polynucleotide obtained from an organism, and a DNA strand obtained by reverse transcription of a polynucleotide obtained from an organism. The second DNA strand may also comprise at least a portion of a gene associated with a cancer in the organism. In one embodiment, the organism is a human and the gene is selected from the group consisting of an oncogene and a tumor suppressor gene. By way of example, such genes include abl, akt2, apc, bcl2α, bcl2β, bcl3, bcr, brcal, brca2, cbl, ccnd1, cdk4, crk-II, csf1r/fins, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, Ick, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf1, wnt1, wnt2, wt1, and yes1. Preferably, the cancer is hereditary non-polyposis colon cancer and the gene is selected from the group consisting of mlh1, msh2, msh3, msh6, pms1, and pms2. Alternately, the cancer may be selected from the group consisting of a leukemia, a lymphoma, a meningioma, a mixed tumor of a salivary gland, an adenoma, a carcinoma, an adenocarcinoma, a sarcoma, a dysgerminoma, a retinoblastoma, a Wilms' tumor, a neuroblastoma, a melanoma, and a mesothelioma.

In another aspect of this method, the mismatched duplex DNA and the MSH dimer are contacted in the presence of at least one non-mismatched duplex DNA. According to this aspect, the method may further comprise separating the MSH dimer from the non-mismatched duplex DNA after contacting the mismatched duplex DNA and the MSH dimer. In one embodiment, the method further comprising dissociating the mismatched duplex DNA and the MSH dimer after separating the MSH dimer from the non-mismatched duplex DNA and thereafter amplifying the mismatched duplex DNA. The MSH dimer may be bound to a support prior to separating the non-mismatched duplex DNA from the MSH dimer and the non-mismatched duplex DNA is separated from the MSH dimer in the presence of a separating solution which is substantially free of ATP. In one embodiment, this method further comprises releasing the mismatched duplex DNA from the MSH dimer after separating the non-mismatched duplex DNA from the MSH dimer. If the mismatched duplex DNA has at least one free end, it may be released from the MSH dimer by contacting the MSH dimer with a releasing solution. The releasing solution may, for example, be selected from the group consisting of a solution comprising ATP and $Mg^{2+}$ ions, a solution comprising ATP and a magnesium-chelating agent, a solution comprising high salt, a solution comprising a gamma-modified ATP analog and $Mg^{2+}$ ions, and a solution comprising a gamma-hydrolysis-resistant ATP analog and $Mg^{2+}$ ions. Preferably, the releasing solution comprises ATP and $Mg^{2+}$ ions. If the mismatched duplex DNA does not have a free end, it may be released from the MSH dimer by contacting the MSH dimer with a releasing solution. This releasing solution may be selected from the group consisting of a solution comprising a magnesium-chelating agent, a solution comprising high salt, a solution comprising a double-stranded DNA cleaving enzyme, ATP and $Mg^{2+}$ ions, a solution comprising a double-stranded DNA cleaving enzyme, a gamma-modified ATP analog, and $Mg^{2+}$ ions, and a solution comprising a double-stranded DNA cleaving enzyme, a gamma-hydrolysis-resistant ATP analog, and $Mg^{2+}$ ions. According to one embodiment, after contacting the mismatched DNA and the MSH dimer, the MSH dimer may be contacted with a MutL homolog.

In another aspect of this method, association of the MSH dimer with the mismatched duplex DNA is detected after or while contacting the MSH dimer with the mismatched duplex DNA. Association of the MSH dimer with the mismatched duplex DNA may be detected, for example, using an assay selected from the group consisting of a gel mobility shift assay, a filter binding assay, an immunological assay, a sedimentation centrifugation assay, a spectroscopic assay, an optical affinity assay, a DNA footprint assay, and a nucleolytic cleavage protection assay.

In still another aspect of this method, the duplex DNA with which the MSH dimer is contacted does not have a free end. If the MSH dimer is present in molar excess with respect to the mismatched duplex DNA, then an average of more than one the MSH dimer associates with one molecule of the mismatched duplex DNA.

The invention also includes a method of modifying a mismatched duplex DNA which does not have a free end. This method comprising contacting the mismatched duplex DNA and an MSH dimer having ADP bound thereto in the presence of a binding solution. The concentration of ATP in the binding solution is less than about 3 micromolar, and the homolog associates with the mismatched region of the mismatched duplex DNA, thereby modifying the mismatched duplex DNA.

The invention further includes a method of segregating a mismatched duplex DNA from a population of DNA molecules. The method comprises contacting an MSH dimer and the population in the presence of a binding solution and segregating the MSH dimer from the population. The binding solution comprises a nucleotide selected from the group consisting of ADP and ATP, an the concentration of ATP in the binding solution is less than about 3 micromolar. The MSH dimer associates with the duplex DNA in the presence of the binding solution. When the MSH dimer is segregated from the population, the mismatched duplex DNA is also segregated from the population.

The invention still further includes a method of detecting a difference between a sample nucleotide sequence and a reference nucleotide sequence. According to this method, a first DNA strand and a second DNA strand are annealed to form a duplex DNA. The first DNA strand has the sample nucleotide sequence, and the second DNA strand has a nucleotide sequence which is complementary to the reference nucleotide sequence. If there is a difference between the sample nucleotide sequence and the reference nucleotide sequence, then the duplex DNA is a mismatched duplex DNA. The duplex DNA and an MSH dimer are contacted in the presence of a binding solution comprising a nucleotide selected from the group consisting of ADP and ATP. The concentration of ATP in the binding solution is less than about 3 micromolar, and the MSH dimer associates with the duplex DNA if the duplex DNA is a mismatched duplex DNA. According to this method, it is then determined whether the MSH dimer is associated with the duplex DNA molecule. Association of the MSH dimer with the duplex DNA molecule is an indication that there is a difference between the sample nucleotide sequence and the reference nucleotide sequence.

In addition, the invention includes a kit for separating a mismatched duplex DNA from non-mismatched duplex DNAs. The kit comprises at least two MutS homologs, a linker for binding the at least one of the MutS homologs to a support, and an additional reagent. The reagent may, for example, be selected from the group consisting of a nucleotide and a releasing solution, wherein the nucleotide is selected from the group consisting of ADP and ATP, and wherein the releasing solution comprises $Mg^{2+}$ and a compound selected from the group consisting of ATP, a gamma-modified ATP analog, and a gamma-hydrolysis-resistant ATP analog.

The invention also includes a method of determining whether a mammal is predisposed for carcinogenesis. This method comprises annealing a first DNA strand and a second DNA strand to form a duplex DNA. The first DNA strand has the nucleotide sequence of at least a portion of a gene selected from the group consisting of an oncogene and a tumor suppressor gene of the mammal. The second DNA strand has a nucleotide sequence which is complementary to the consensus nucleotide sequence of this region. If there is a sequence difference between the first DNA strand and the second DNA strand then the duplex DNA is a mismatched duplex DNA. The duplex DNA and an MSH dimer are contacted in the presence of a binding solution comprising a nucleotide selected from the group consisting of ADP and ATP. The concentration of ATP in the binding solution is less than about 3 micromolar, and the MSH dimer associates with the duplex DNA if the duplex DNA is a mismatched duplex DNA. According to this method, it is determined whether the MSH dimer is associated with the duplex DNA, whereby association of the MSH dimer with the duplex DNA is an indication that the mammal is predisposed for carcinogenesis.

The invention further includes a method of fractionating a population of duplex DNAs. This method comprises contacting the population with an MSH dimer in the presence of a binding solution comprising a nucleotide selected from the group consisting of ADP and ATP. The concentration of ATP in the binding solution is less than about 3 micromolar, and the MSH dimer associates with at least one mismatched duplex DNA in the population. The MSH dimer is segregated from the population of duplex DNAs, whereby the mismatched duplex DNA is also segregated from the population. The population is thereby fractionated.

The invention still further includes a method of selectively amplifying at least one mismatched duplex DNA of a population of duplex DNAs. This method comprises contacting the population with an MSH dimer in the presence of a binding solution comprising a nucleotide selected from the group consisting of ADP and ATP. The concentration of ATP in the binding solution is less than about 3 micromolar, and the MSH dimer associates with the mismatched duplex DNA. The MSH dimer is thereafter segregated from the population of duplex DNAs, whereby the mismatched duplex DNA is also segregated from the population of duplex DNAs. The mismatched duplex DNA is then amplified, whereby the mismatched duplex DNA is selectively amplified.

The invention also includes a method of determining whether the nucleotide sequence of a first copy of a genomic sequence differs from the nucleotide sequence of a second copy of the genomic sequence. This method comprises amplifying a region of each of the first copy and the second copy of the genomic sequence to yield amplified first copies and amplified second copies. The amplified first copies and the amplified second copies are mixed and denatured to form a first mixture. The nucleic acids in the first mixture are then annealed to form a second mixture comprising duplex DNAs. If the nucleotide sequence of first copy and the nucleotide sequence of the second copy of the genomic sequence differ, then at least some of the duplex DNAs in the second mixture are mismatched duplex DNAs. The annealed second mixture is contacted with an MSH dimer in the presence of a binding solution comprising a nucleotide selected from the group consisting of ADP and ATP. The concentration of ATP in the binding solution is preferably less than about 3 micromolar, whereby the MSH dimer associates with mismatched duplex DNA. According to this method, it is then determined whether the MSH dimer is associated with at least some of the duplex DNAs. Association of the MSH dimer with at least some of the duplex DNAs is an indication that the nucleotide sequence of the first copy of the genomic sequence differs from the nucleotide sequence of the second copy of the genomic sequence.

The invention further includes a composition for segregating a mismatched duplex DNA from a population of duplex DNAs. The composition comprises an MSH heterodimer bound to a support.

The invention still further includes a kit for screening a genomic region for a nucleotide sequence which differs from a reference nucleotide sequence. This kit comprises a pair of primers complementary to the ends of the region for amplifying the region, a DNA strand having the reference nucleotide sequence, and at least two MutS homologs.

The invention yet further relates to a nonhuman mammal which is nullizygous for both Msh2 and p53. The mammal does not express Msh2 or p53 and exhibits a phenotype selected from the group consisting of inappropriate fetal apoptosis and a predisposition for carcinogenesis.

The invention also relates to a method of making a nonhuman mammal which is nullizygous for both Msh2 and p53, does not express Msh2 or p53, and exhibits a phenotype selected from the group consisting of a predisposition for inappropriate fetal apoptosis and a predisposition for carcinogenesis. This method comprises mating a) a first parent mammal which comprises at least one null allele of Msh2 and at least one null allele of p53 and b) a second parent mammal comprising at least one null allele of Msh2 and at least one null allele of p53. As a result of this mating, a non-human mammal is generated which is nullizygous for both Msh2 and p53, does not express Msh2 or p53, and exhibits a phenotype selected from the group consisting of inappropriate fetal apoptosis and a predisposition for carcinogenesis.

The invention further relates to a method of determining whether a compound affects tumorigenesis in mammals. This method comprises administering the compound to a first nonhuman mammal which is nullizygous for both Msh2 and p53, does not express Msh2 or p53, and exhibits a predisposition for carcinogenesis. Tumor incidence in the first nonhuman mammal is compared with tumor incidence in a second nonhuman mammal of the same type which is nullizygous for both Msh2 and p53, does not express Msh2 or p53, exhibits a predisposition for carcinogenesis, and to which the compound is not administered. A difference in tumor incidence in the first transgenic mammal compared with tumor incidence in the second transgenic mammal is an indication that the compound affects tumorigenesis in mammals.

The invention still further relates to a method of determining whether a compound affects a biological phenomenon in mammals. The phenomenon may, for example, be selected from the group consisting of apoptosis, aging, and fetal development. The method comprises administering the compound in utero to a first nonhuman mammalian embryo which is nullizygous for both Msh2 and p53, does not express Msh2 or p53, and exhibits a predisposition for inappropriate fetal apoptosis. The development of the first nonhuman mammalian embryo is compared with the development of a second nonhuman mammalian embryo of the same type which is nullizygous for both Msh2 and p53, does not express Msh2 or p53, exhibits a predisposition for inappropriate fetal apoptosis, and to which the compound is not administered. A difference in the development of the first nonhuman mammalian embryo compared with the development of the second nonhuman mammalian embryo is an indication that the compound affects the biological phenomenon in mammals.

The invention yet further relates to a cell line which is nullizygous for both Msh2 and p53, does not express Msh2 or p53, and exhibits a phenotype selected from the group consisting of a predisposition for carcinogenesis and a predisposition for apoptosis. The cell line is made by culturing a cell obtained from the nonhuman mammal described herein.

The invention also relates to a method of determining whether a composition affects expression of a gene selected from the group consisting of the p53 gene and a gene encoding a MutS homolog. This method comprising administering the composition to a first non-human mammal which is nullizygous for one of the p53 gene and the gene encoding a MutS homolog. A phenotype of the non-human mammal is compared with the phenotype of a second non-human mammal of the same type which is not nullizygous for the one of the p53 gene and the gene encoding a MutS homolog, wherein the phenotype is selected from the group consisting of inappropriate fetal apoptosis and a predisposition for carcinogenesis. A difference between the phenotype of the first non-human mammal and the phenotype of the second non-human mammal is an indication that the composition affects expression of the other of the p53 gene and the gene encoding a MutS homolog.

The invention further relates to a method of determining whether a composition affects expression of a gene selected from the group consisting of the p53 gene and a gene encoding a MutS homolog. This method comprises administering the composition to a first cell derived from a non-human mammal which is nullizygous for one of the p53 gene and the gene encoding a MutS homolog. A phenotype of the first cell is compared with the phenotype of a second cell derived from a non-human mammal of the same type which is not nullizygous for the one of the p53 gene and the gene encoding a MutS homolog, wherein the phenotype is selected from the group consisting of inappropriate fetal apoptosis and a predisposition for carcinogenesis. A difference between the phenotype of the first cell and the phenotype of the second cell is an indication that the composition affects expression of the other of the p53 gene and the gene encoding a MutS homolog.

The invention still further relates to a composition comprising a human MutS homolog fragment, wherein the fragment comprises a MutS homolog interaction region.

The invention yet further relates to a method of inhibiting association of a first human MutS homolog and a second human MutS homolog. This method comprises contacting at least one of the first human MutS homolog and the second human MutS homolog with a human MutS homolog fragment comprising a MutS homolog interaction region. Inhibition of the first and the second human MutS homologs is thus inhibited.

The invention also relates to a composition comprising substantially purified hMSH5.

The invention further relates to a composition comprising an isolated nucleic acid encoding hMSH5.

The invention still further includes an alternate method of modifying a mismatched duplex DNA. This method comprises contacting an MSH dimer and the mismatched duplex DNA in the presence of a binding solution comprising ADP. The concentration of ADP in the binding solution is at least about ten times the concentration of ATP, if ATP is present in the binding solution. The MSH dimer thereby associates with the mismatched region of the mismatched duplex DNA and modifies the mismatched duplex DNA.

BRIEF DESCRIPTION OF THE DRAWINGS

FIG. 1, comprising FIGS. 1A, 1B, 1C, 1D, 1E, and IF, depict binding of hMSH2:hMSH6 heterodimer to mismatched and non-mismatched duplex DNA.

FIG. 2, comprising FIG. 2A is an image of an assay in which the product corresponding to the S-shifted electrophoretic band was incubated in the presence of ATP at the following concentration, in micromolar, 0 in A and B, 0.5 in C, 1 in D, 2 in E, 3.9 in F, 7.8 in G, 15.6 in H, 31.3 in I, 62.5 in J, and 125 in K. FIG. 2B is an image of an assay in which the product corresponding to the S-shifted electrophoretic band was incubated in the presence of adenosine-5'-O-3'-thiotriphosphate (ATP-γ-S) at the following concentration, in micromolar, 0 in A and B, 0.5 in C, 1 in D, 2 in E, 3.9 in F, 7.8 in G, 15.6 in H, 31.3 in I, 62.5 in J, and 125 in K. FIG. 2C is an image of an assay in which the product corresponding to the S-shifted electrophoretic band was incubated in the presence of ADP at the following concentration, in micromolar, 0 in A and B, 25 in C, and 100 in D. In lane A of each of FIGS. 2A, 2B, and 2C, no heterodimer was included in the assay mixture. FIG. 2D is a graph which depicts quantitated results obtained using the results depicted in FIGS. 2A, 2B, and 2C, as assessed using a phosphoimaging device.

FIG. 4, comprising FIG. 4A is a graph depicting the results of gel mobility shift assays performed in the presence or absence of 15 micromolar ATP and in the presence or absence of 15 micromolar ATP-$\gamma$-S. Magnesium chloride was added at the time designated "0", and samples of the assay mixture were collected at the indicated times (in minutes). The binding reaction in each mixture was halted by addition of 5 millimolar EDTA. FIG. 4B is a graph depicting the results of gel mobility shift assays performed in the presence of the indicated (in millimolar) concentrations of ATP or ADP or both.

FIG. 5 comprises FIGS. 5A and 5B.

FIG. 6, comprising FIG. 6A is an image of the results obtained from gel mobility shift assays in which heterodimer-bound mismatched DNA was incubated with ATP for the following time, in minutes, 0 in A and B, 0.5 in C, 1 in D, 2 in E, 3 in F, 4 in G, 5 in H, 7.5 in I, and 10 in J. FIG. 6B is an image of the results obtained from gel mobility shift assays in which heterodimer-bound mismatched DNA was incubated with ATP and a 400-fold excess of homologous DNA for the following time, in minutes, 0 in A and B, 0.5 in C, 1 in D, 2 in E, 3 in F, 4 in G, 5 in H, 7.5 in I, and 10 in J. FIG. 6C is an image of the results obtained from gel mobility shift assays in which heterodimer-bound mismatched DNA was incubated with a 400-fold excess of homologous DNA for the following time, in minutes, 0 in C, 5 in D, and 10 in E. FIG. 6D is an image of the results obtained from gel mobility shift assays in which the heterodimer was incubated with homoduplex DNA probe for fifteen minutes at 37° C. (Lane B), the assay mixture was cooled to 4° C., and a 1,100-fold excess of unlabeled competitor homoduplex DNA was added (Lane C). In each of FIGS. 6A, 6B, 6C, and 6D, the assay mixtures corresponding to lane A did not comprise the heterodimer.

FIG. 8, comprising FIGS. 8A, 8B, 8C, and 8D, lists the nucleotide sequence of single nucleotide chains of some of the 39- and 81-base pair DNA substrates described herein. FIG. 8A lists SEQ ID NO: 2. FIG. 8B lists SEQ ID NO: 3. FIG. 8C lists SEQ ID NO: 5. FIG. 8D lists SEQ ID NO: 6.

FIG. 9, comprising

Figure 14:
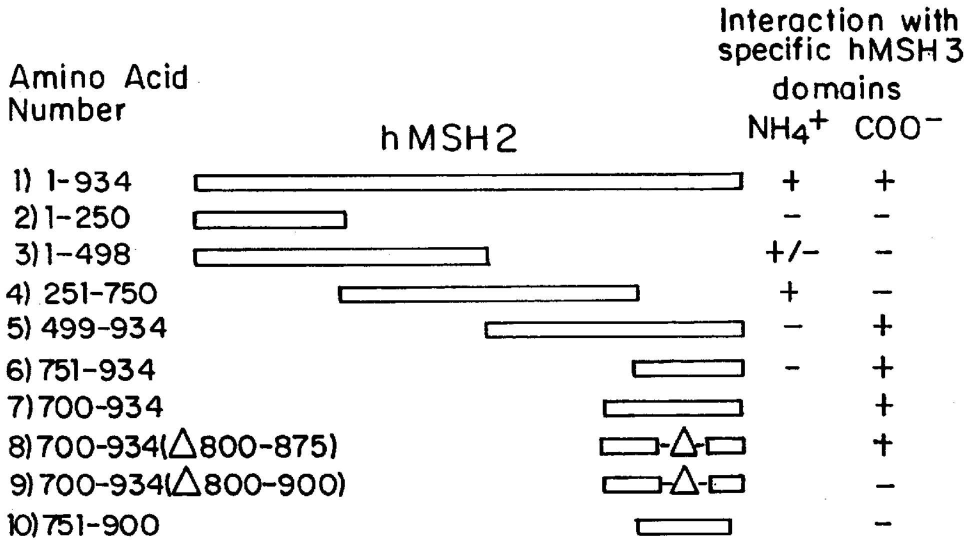

FIG. 14 is a diagram which indicates the primary structure of $^{35}$S-labeled IVTT-hMSH2 polypeptides used to identify the linear orientation of the hMSH3-interaction regions of hMSH2. "Amino Acid Number" refers to the amino acid residues of hMSH2 which were present in the corresponding IVTT-hMSH2 polypeptide. The rectangular entities in the central part of the figure represent relative positions of the amino acid residues which were present in the corresponding IVTT-hMSH2 polypeptide with respect to full length hMSH3, which is represented by polypeptide 1). The symbol, Δ, indicates a deleted region of a polypeptide. "Interaction with specific hMSH3 domains" indicates whether or not the corresponding polypeptide interacted with a GST-hMSH3 fusion protein comprising the amino-terminal ("$NH_4^+$") interaction region of hMSH3 or with a GST-hMSH3 fusion protein comprising the carboxy-terminal ("$COO^-$") interaction region of hMSH3.

Figure 15:
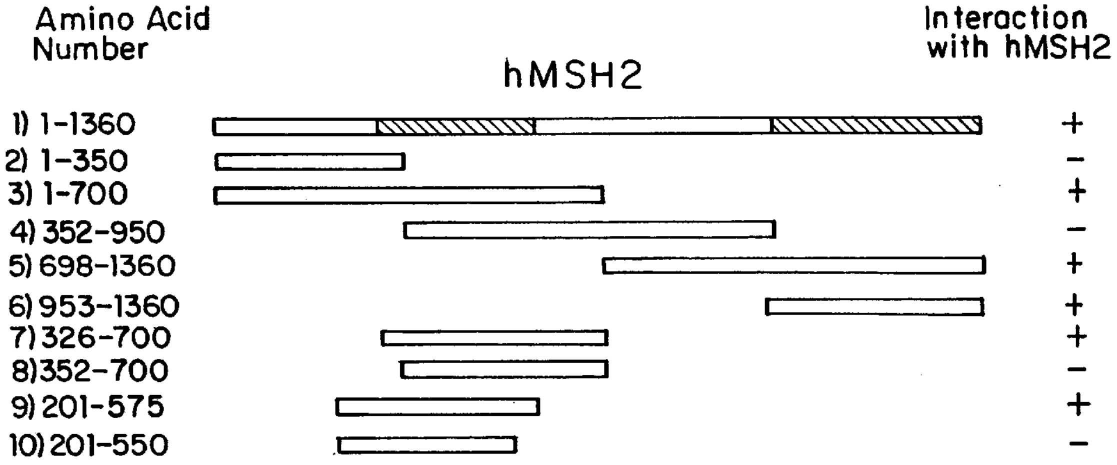

FIG. 15 is a diagram which indicates the primary structure of $^{35}$S-labeled IVTT-hMSH6 polypeptides used to identify approximate boundaries of hMSH2-interaction regions of hMSH6. "Amino Acid Number" refers to the amino acid residues of hMSH6 which were present in the corresponding IVTT-hMSH2 polypeptide. The rectangular entities in the central part of the figure represent relative positions of the amino acid residues which were present in the corresponding IVTT-hMSH6 polypeptide with respect to full length hMSH6, which is represented by polypeptide 1). The shaded regions of polypeptide 1) represent the hMSH2-interaction regions of hMSH6. "Interaction with hMSH2" indicates whether or not the corresponding polypeptide interacted with GST-hMSH2.

Figure 16:
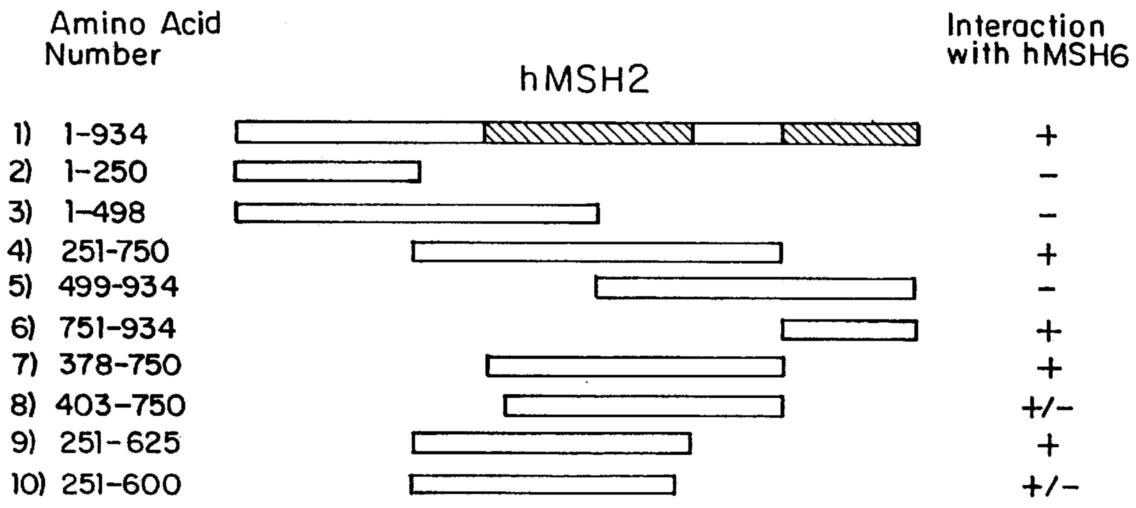

FIG. 16 is a diagram which indicates the primary structure of $^{35}$S-labeled IVTT-hMSH2 polypeptides used to identify approximate boundaries of hMSH6-interaction regions of hMSH2. "Amino Acid Number" refers to the amino acid residues of hMSH2 which were present in the corresponding IVTT-hMSH2 polypeptide. The rectangular entities in the central part of the figure represent relative positions of the amino acid residues which the corresponding IVTT-hMSH2 polypeptide comprised with respect to full length hMSH2, which is represented by polypeptide 1). The shaded regions of polypeptide 1) represent the hMSH6-interaction regions of hMSH2. "Interaction with hMSH3" indicates whether or not the corresponding polypeptide interacted with GST-hMSH6.

Figure 17:

FIG. 17 is a diagram which indicates the primary structure of $^{35}$S-labeled IVTT-hMSH2 polypeptides used to identify the linear orientation of the hMSH6-interaction regions of hMSH2. "Amino Acid Number" refers to the amino acid residues of hMSH2 which were present in the corresponding IVTT-hMSH2 polypeptide. The rectangular entities in the central part of the figure represent relative positions of the amino acid residues which were present in the corresponding IVTT-hMSH2 polypeptide with respect to full length hMSH6, which is represented by polypeptide 1). The symbol, Δ, indicates a deleted region of a polypeptide. "Interaction with specific hMSH6 domains" indicates whether or not the corresponding polypeptide interacted with a GST-hMSH6 fusion protein comprising the amino-terminal ("$NH_4^+$") interaction region of hMSH6 or with a GST-hMSH6 fusion protein comprising the carboxy-terminal ("$COO^-$") interaction region of hMSH6.

Figure 18:
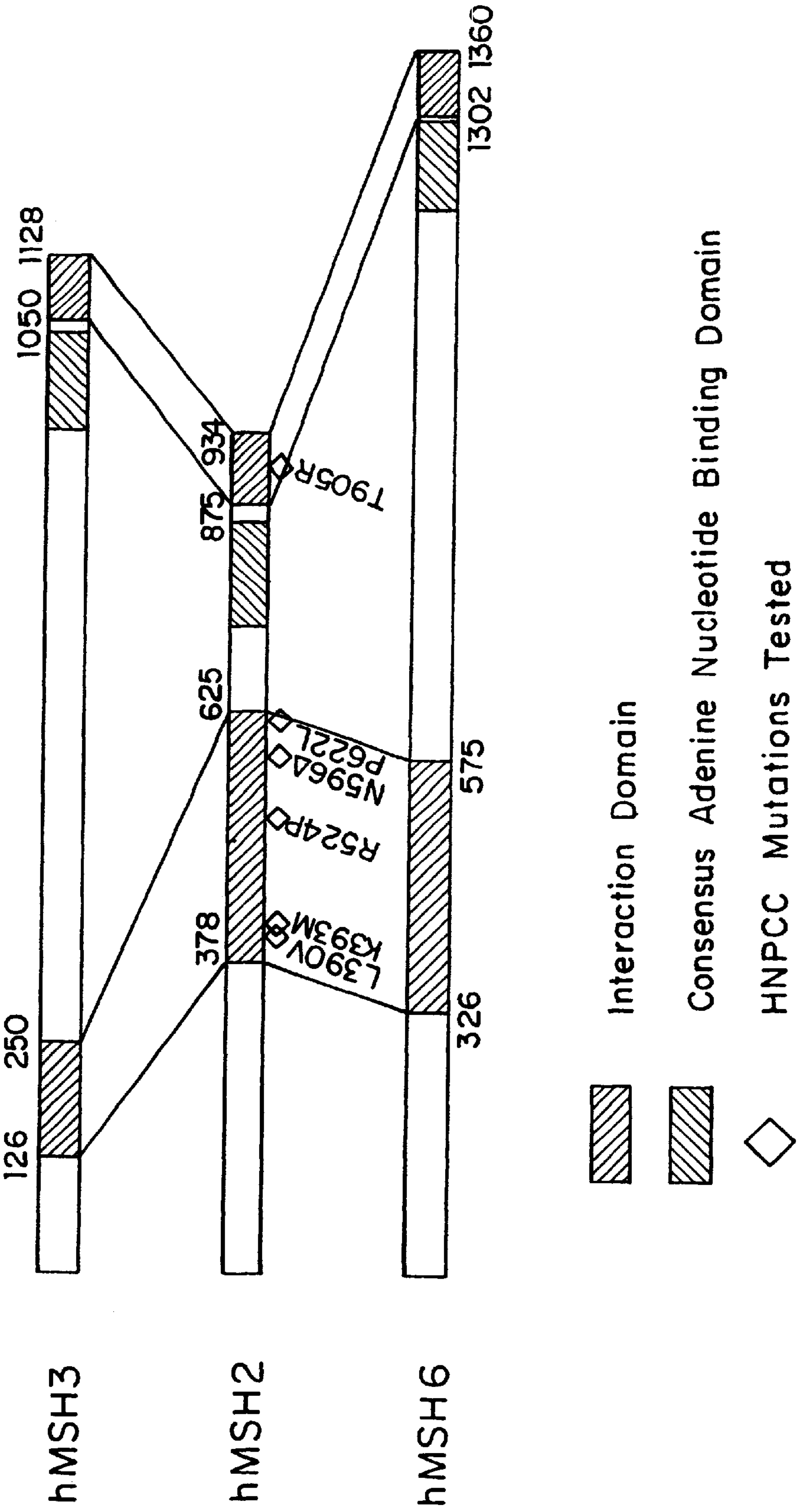

FIG. 18 is a diagram which illustrates a model of hMSH2 consensus interaction with hMSH3 or hMSH6. The interaction regions of hMSH2, hMSH3, and hMSH6 are indicated are connected with lines that illustrate the specificity of each region to its corresponding interaction partner region. The nucleotide binding regions of hMSH2, hMSH3, and hMSH6 are indicated. The location of HNPCC-associated mutations tested in these studies are illustrated as black diamonds.

FIG. 19, comprising FIGS. 19A through 19G, lists the nucleotide sequence of cDNA encoding hMSH5 (SEQ ID NO: 30) and the putative amino acid sequence of hMSH5 (SEQ ID NO: 29).

DETAILED DESCRIPTION OF THE INVENTION

The invention relates to a method of binding one or more MutS homolog (MSH) dimers to a mismatched duplex DNA. The invention also relates to methods of using adenine nucleotides to modulate recognition of mismatched duplex DNA and to modulate DNA-associated diffusion of MSH dimers after binding of such dimers to mismatched duplex DNA. The invention further relates to a method of binding a complex comprising a MutL homolog and a MutS homolog to mismatched duplex DNA. The MutL homolog interacts with the MutS homolog and influences the ability of the MutS homolog to bind with a mismatched region of the duplex DNA.

A Summary of Some of the Novel Properties of MutS Homologs and MutL Homologs

The compositions, kits, and methods of the invention may be better understood by understanding the novel properties of MutS homologs and MutL homologs which have been discovered by the inventors. This section presents merely a brief introduction to several these properties. It is understood that the operability of the compositions, kits, and methods of the invention does not depend upon the correctness of the information provided in this section.

An important aspect of the invention is the discovery that MutS homolog (MSH) dimers and, in some organisms, MSH heterodimers, associate with mismatched regions of a mismatched duplex DNA. Binding of a MutS dimer to mismatched DNA occurs when ADP, but not ATP, is bound to the MSH dimer. The MSH dimer may, for example, be in the form of an MSH homodimer (e.g. an *E. coli* MutS dimer) or an MSH heterodimer (e.g. a human MSH heterodimer such as an hMSH2:hMSH3 dimer, an hMSH2:hMSH6 dimer, or an hMSH4:hMSH5 dimer). This association may be effected either in vitro or in vivo.

ADP-bound MSH dimer associated with a mismatched region of a mismatched duplex DNA does not move along the duplex DNA, but instead remains located at the mismatched region. Exchange of ATP for the ADP bound to the MSH dimer confers to the MSH dimer DNA-associated diffusibility, which means that the MSH dimer becomes able to move from the site of the mismatched region of the duplex DNA to another site on the same duplex DNA. If the mismatched duplex DNA has a free end, then the DNA-associated diffusibility of an ATP-bound MSH dimer enables the dimer to the duplex DNA dissociate from the duplex DNA. If the mismatched duplex DNA does not have a free end (e.g. the DNA is circular or has bulky moieties such as proteins bound to the ends thereof), then neither the ADP-bound form or the ATP-bound form of the MSH dimer is able to dissociate from the duplex DNA.

Because MSH heterodimers, in their ATP-bound form, exhibit DNA-associated diffusibility with regard to the duplex DNA with which they are associated, an ATP-bound MSH dimer will not necessarily be associated with the mismatched region of a mismatched duplex DNA, but instead may have diffused away from the mismatched region to complementary region of the same mismatched duplex DNA. Thus, a mismatched duplex DNA having one or more ATP-bound MSH dimers associated therewith is able to associate with another MSH dimer in an ADP-bound form. Therefore, numerous MSH dimers may be associated with a mismatched duplex DNA by contacting the DNA with ADP-bound MSH dimers in the presence of a binding solution which comprises ATP. It is understood that certain MSH homodimers (e.g. hMSH2 dimers; Fishel et al., 1994, Science 266:1403–1405) exhibit little or no alteration in activity associated with adenine nucleotide binding, and may be useful for these properties. For example, hMSH2 binds a variety of mismatched nucleotides but remains unperturbed in the presence of either ADP or ATP (Fishel et al., 1994, Science 266:1403–1405).

MSH dimers exhibit an intrinsic ATP hydrolytic activity, and this hydrolytic activity is greatly enhanced in their non-DNA-associated form, but not in their DNA-associated form. Thus, an ATP-bound MSH dimer associated with DNA remains ATP-bound. However, ATP bound to an MSH dimer is rapidly converted to ADP if the dimer is not associated with DNA. Thus, the intrinsic ATPase activity exhibited by MSH dimers catalyzes the transformation of an ATP-bound dimer (which cannot associate with a mismatched region of DNA) to an ADP-bound dimer (which can associate with a mismatched region of DNA). In addition, the mismatched DNA-associated form of MSH dimers are able to more rapidly exchange ATP in place of ADP bound to the dimer than MSH dimers not associated with DNA or associated with non-mismatched DNA.

Figure 7:
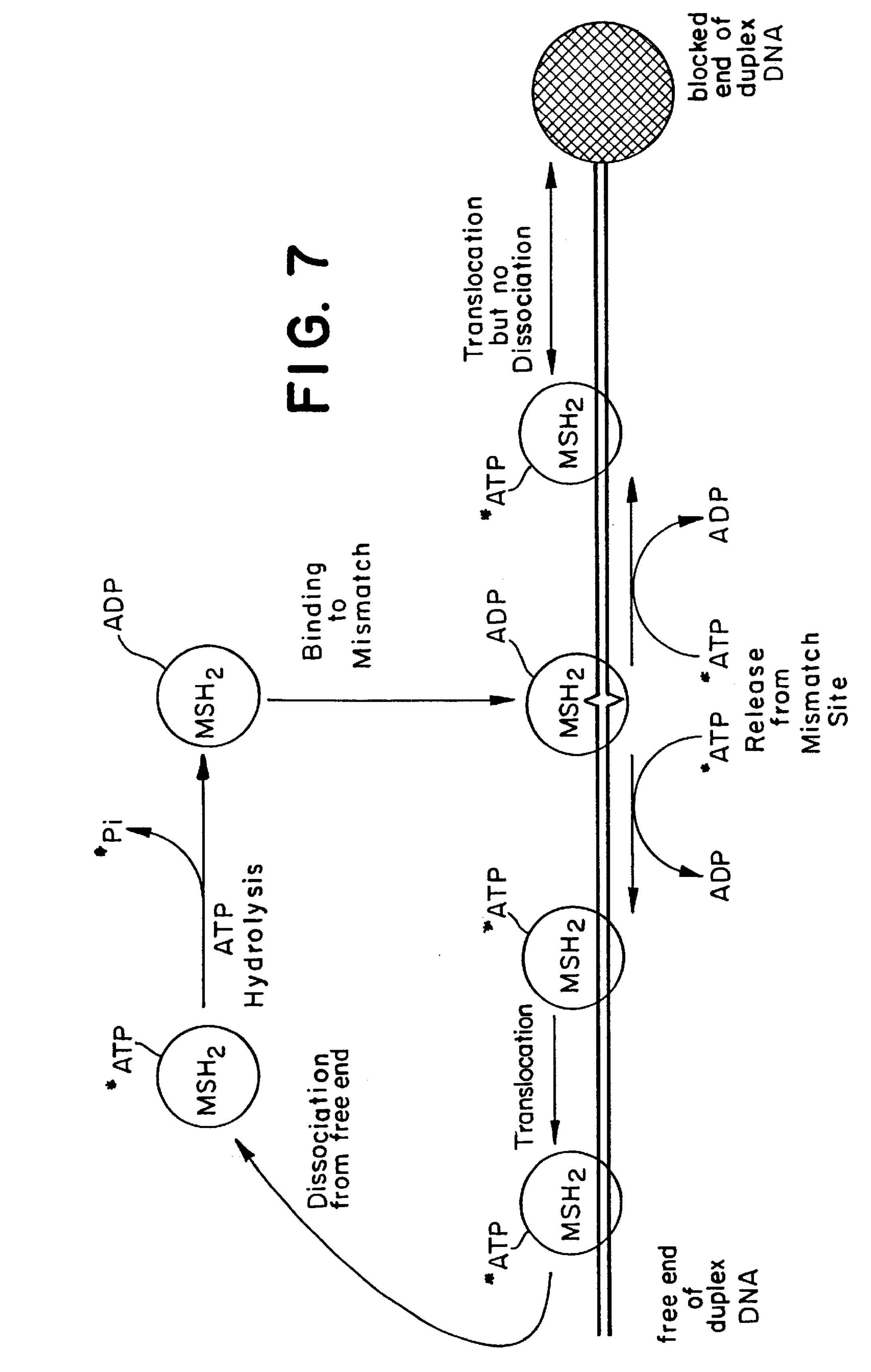
FIG. 7 is a diagram which depicts the model of the hMSH2:hMSH6 heterodimer association with and dissociation from mismatched duplex DNA described herein. The ADP-bound form of the heterodimer ("$MSH_2$"), which is shown in the center of the diagram, is competent to bind mismatched duplex DNA, as shown at the bottom of the diagram, but cannot diffuse from the mismatch site on the DNA. Mismatched DNA-bound complex is enabled to diffuse to a different position on the DNA by displacement of the ADP molecule bound thereto by an ATP molecule (here indicated "*ATP"), which yields the ATP-bound form of the heterodimer. The ATP-bound form of the heterodimer is able to dissociate from a free end of the duplex DNA, but not from a blocked end of the duplex DNA. After dissociating from the duplex DNA, the ATP-bound form of the heterodimer is converted to the ADP-bound form by hydrolysis of the heterodimer-bound ATP molecule, catalyzed by intrinsic ATPase activity of the heterodimer.

Without wishing to be bound by any particular theory of operation, binding of MSH dimers to mismatched duplex DNA may be visualized as illustrated in FIG. 7. An ADP-bound MSH dimer associates with the mismatched region of the DNA. Exchange of ATP in place of the ADP bound to the MSH dimer enables the dimer to diffuse to a different position on the DNA. The DNA-associated ATP-bound MSH dimer cannot dissociate from a blocked end of the DNA in the presence of $Mg^{2+}$, but can dissociate from a free end of the DNA. Alternately, ATP-bound MSH dimer can be dissociated from DNA which does not have a free end in the presence of EDTA or a high salt concentration. ATP-bound MSH dimer not associated with DNA is able to hydrolyze the ATP moiety, yielding an ADP-bound MSH dimer, which is then able to associate with a mismatched region of DNA.

An MSH dimer may be thought of as 'molecular switch,' wherein the ADP-bound dimer represents an 'ON' state, and wherein the ATP-bound dimer represents an 'OFF' state. In the 'ON' state, the dimer is able to associate with a mismatched region of DNA but is not able to diffuse to a different position on the DNA with which it is associated. In the 'OFF' state, the dimer is not able to associate with a mismatched region of DNA but is able to diffuse to a different position on the DNA with which it is associated. Recalling the involvement of MutS homologs in DNA mismatch repair and, as demonstrated herein, in control of the cell replication cycle, it is understood that compounds which modulate the transition of MSH dimers from the 'ON' to the 'OFF' state or vice versa may be used to modulate DNA mismatch repair, timing of and progression through the cell replication cycle, and/or the physiological process (es) associated with either DNA mismatch repair or the cell replication cycle.

A MutL homolog improve the intrinsic ATPase activity exhibited by a MSH dimer when the MutL homolog associates with the MSH dimer. MutL homologs may thus be analogized to GTPase accelerating proteins (sometimes designated "GAP proteins") which have been described in the context of G protein activity. Without wishing to be bound by any particular theory, it is thought that association of a MutL homolog with a MSH dimer increases the rate of dissociation of the ATP-bound MSH dimer from duplex DNA and increases the rate at which ATP is converted to ADP by the non-duplex DNA-associated ATP-bound MSH dimer, thereby rendering the MSH dimer able to bind to a mismatched duplex DNA more rapidly than in the absence of the MutL homolog.

The biochemical properties of MutS homologs and MutL homologs described in this section are used advantageously in the compositions, kits, and methods of the invention.

Definitions

As used herein, each of the following terms has the meaning associated with it in this section.

A "MutS homolog" is a protein which comprises a region which exhibits significant sequence similarity with at least one of the following regions of the human MSH2 protein (wherein the regions are indicated by the numbers of the amino acid residues of MSH2 which, inclusively, bound the region; the corresponding amino acid sequences of hMSH2 is indicated thereafter in parentheses):

Region I: hMSH2 amino acid residues 37–57 (LFDRGDFYTA HGEDALLAAR E; SEQ ID NO: 24);

Region II: hMSH2 amino acid residues 336–368 (TPQGQRLVNQ WIKQPLMDKN RIEERLNLVE AFV; SEQ ID NO: 25);

Region III: hMSH2 amino acid residues 635–662 (LKASRHACVE VQDEIAFIPN DVYFEKDK; SEQ ID NO: 26);

Region IV: hMSH2 amino acid residues 667–770 (IITGPNMGGK STYIRQTGVI VLMAQIGCFV PCESAEVSIV DCILARVGAG DSQLKGVSTF MAEMLETASI LRSATKDSLI IIDELGRGTS TYDGFGLAWA ISEY; SEQ ID NO: 27); and Region V: hMSH2 amino acid residues 812–852 (LTMLYQVKKG VCDQSFGIHV AELANFPKHV IECAKQKALE L; SEQ ID NO: 28).

The amino acid sequence of hMSH2 has been described (e.g. Fishel et al., 1993, Cell 75:1027). Preferably, the MutS homolog of the invention comprises a region which exhibits significant sequence similarity with Region IV, and more preferably with both Region IV and Region V. It is also preferred that the MutS homolog comprises a plurality of regions, each of which exhibits significant sequence similarity with one of Regions I–V of hMSH2, and more preferred that the MutS homolog comprises regions which independently exhibit significant sequence similarity with each of Regions I–V of hMSH2. Thus, MutS homologs which are included in the invention include, but are not limited to *Aquifex aeolicus* MutS, *Aquifex aeolicus* MSH, *Aquifiex pyrophilicus* MutS, *Arabidopsis thaliana* MSH2, *Arabidopsis thaliana* MSH6, *Azotobacter vinelandii* MutS, *Bacillus subtilis* MutS, *Bacillus subtilis* MSH, *Caenorhabdis elegans* MSH4, *Caenorhabdis elegans* MSH5, *Drosophila melanogaster* MSH2, *Escherichia coli* MutS, *Homo sapiens* MSH2, *Homo sapiens* MSH3, *Homo sapiens* MSH4, *Homo sapiens* MSH5, *Homo sapiens* MSH6, *Haemophilus influenzae* type B MutS, *Helicobacter pylori* MSH, *Mus musculus* MSH2, *Mus musculus* MSH3, *Mus musculus* MSH6, *Neurospora crassa* MSH2, *Rattus norvegicus* MSH2, *Saccharomyces cerevisiae* MSH 1, *Saccharomyces cerevisiae* MSH2, *Saccharomyces cerevisiae*

MSH3, *Saccharomyces cerevisiae* MSH4, *Saccharomyces cerevisiae* MSH5, *Saccharomyces cerevisiae* MSH6, *Saccharomyces pombe* MSH1, *Saccharomyces pombe* MSH2, *Saccharomyces pombe* Swi4, *Saccharomyces pombe* MutS, *Salmonella typhimurium* MutS, Synechocystis sp. MutS, Synechocystis sp. MSH, *Thermus aquaticus* MutS, *Thermotoga maritima* MutS, and *Thermus thermophilus* MutS, each of which proteins is described either herein or in the prior art.

A "MutL homolog" is a protein which exhibits significant similarity to the MutL protein of *E. coli*. MutL homologs include, but are not limited to, eukaryotic MLH1, MLH2, PMS1, and PMS2 proteins.

A protein or a region of a protein exhibits "significant similarity" to another protein or a region of another protein if, when the two proteins or regions are compared in a selected alignment, at least 50%, at least 70%, at least 85%, at least 95%, or at least 99% of the aligned amino acid residues of the two proteins or the two regions are either identical or similar. Similar amino acid residues are indicated by the groups listed on the following lines:

glycine, alanine;

valine, isoleucine, leucine;

aspartic acid, glutamic acid;

asparagine, glutamine;

serine, threonine;

lysine, arginine; and phenylalanine, tyrosine.

A "heterodimer" is a protein which comprises more than one subunit, wherein at least one subunit has an amino acid sequences which is different from the amino acid sequence of another subunit of the same protein. Heterodimers having an 'A' protein subunit and a 'B' protein subunit are herein designated "A:B heterodimers".

A "DNA strand" is a single polydeoxyribonucleotide.

A "duplex DNA" is a molecule that comprises at least one polydeoxyribonucleotide, wherein at least a portion of the polydeoxyribonucleotide has a double-stranded, hydrogen bonded conformation.

A "mismatched" duplex DNA is a duplex DNA wherein at least one DNA strand comprises a region which has at least one nucleotide residue that is not base-paired with a complementary nucleotide residue and which is flanked by regions wherein at least about ten nucleotide residues are all base-paired with complementary nucleotide residues.

A first region of an DNA "flanks" a second region of the DNA if the two regions are adjacent one another or if the two regions are separated by no more than about 10 nucleotide residues, and preferably no more than 1 nucleotide residue.

A "non-mismatched" duplex DNA is a duplex DNA wherein all nucleotide residues of the double-stranded portion thereof are base-paired with complementary nucleotide residues.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A chemical entity such as a molecule is "bound" to another chemical entity if at least one portion of each of the two chemical entities are covalently or non-covalently bonded to one another in an essentially fixed position. By way of example, as described herein, an ADP-bound form of an MSH dimer is bound to a mismatched region of a duplex DNA because the MSH dimer predominantly associates with the duplex DNA at the location of the mismatch.

A chemical entity such as a molecule is "associated" with another chemical entity if at least one of the chemical entities can change its position relative to the other without becoming dissociated therefrom. By way of example, as described herein, an ATP-bound form of an MSH dimer is associated with a mismatched duplex DNA because the MSH dimer can diffuse to a different position on the DNA without dissociating therefrom.

A duplex DNA is "modified" if a chemical entity such as a molecule is bound to, associated with, or dissociated from the duplex DNA, or if the duplex DNA is segregated from a population of DNA molecules.

A duplex DNA has a "free end" if the duplex DNA is not circular and if both ends of the duplex DNA are not blocked.

An end of a duplex DNA is "blocked" if a bulky moiety is bound to a portion of the duplex DNA between a reference point on the duplex DNA and the end of the duplex DNA.

A "bulky moiety" bound to a portion of a duplex DNA is any chemical entity which has a size sufficient to prevent sliding of an ATP-bound MSH dimer along the DNA duplex from a location on one side of the bulky moiety to a location on the other side of the bulky moiety. Examples of bulky moieties include proteins, metallic, glass, or polymeric surfaces, and the like.

A "gamma-modified ATP analog" is an ATP molecule which has an a group attached to the gamma phosphodiester moiety thereof, whereby the beta-gamma phosphodiester linkage is cleaved by an MSH dimer with an efficiency less than 25% of the efficiency with which ATP is hydrolyzed by the MSH dimer. By way of example, ATP-$\gamma$-S is a gamma-modified ATP analog.

A "gamma-hydrolysis-resistant ATP analog" is an ATP molecule which has an altered beta-gamma phosphodiester linkage chemistry whereby the altered beta-gamma phosphodiester linkage cannot be cleaved be either the intrinsic ATP hydrolytic activity of an MSH dimer or by the ATP hydrolytic activity of an MSH dimer-MutL homolog complex. Examples of gamma-hydrolysis-resistant ATP analogs include, but are not limited to ATP-PNP and ATP-PCP, which are compounds well known and described in the art.

A solution is "substantially free" of ATP when the concentration of ATP is very low (e.g. less than 30 nanomolar, and preferably less than 1 nanomolar).

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

"Nullizygous" refers to an animal which possesses a pair of null mutant alleles at a given genetic locus. Hence, a nullizygous Xxx mouse (wherein Xxx is any gene normally present in a mouse) does not possess a functional Xxx gene, whereas a wild-type mouse may possess one or two functional copies of the Xxx gene. To illustrate the notation used herein, the term "nullizygous Xxx mouse" is synonymous with the term "$Xxx^{-/-}$ mouse." Similarly, a "heterozygous Xxx mouse" has one functional Xxx allele and one non-functional Xxx allele, and is synonymous with the term "$Xxx^{+/-}$ mouse." A "wild type mouse" has at least one copy, and possibly two copies, of a functional Xxx allele, and is synonymous with the term "$Xxx^{+/\pm}$ mouse." A "homologous wild type mouse' has two copies of a functional Xxx allele, and is synonymous with the term "$Xxx^{+/+}$ mouse."

As used herein, an "instructional material" includes a publication, a recording, a diagram, or any other medium of expression which can be used to communicate the usefulness of the compositions and methods of the invention for associating a MSH dimer with a mismatched duplex DNA. The instructional material of the kit of the invention may, for example, be affixed to a container which contains the dimer or be shipped together with a container which contains the dimer. Alternatively, the instructional material may be shipped separately from the container with the intention that the instructional material and the dimer be used cooperatively by the recipient.

A solution comprises "high salt" if the concentration of one or more salts in the solution is, cumulatively, at least about 1 molar, preferably at least about 3 molar.

A "double-stranded DNA-cleaving enzyme" is an enzyme which catalyzes hydrolysis of both strands of a duplex DNA, leaving either blunt or staggered ends. Examples of double-stranded DNA-cleaving enzymes include, but are not limited to, restriction endonucleases.

Description

The invention relates to a method of modifying a mismatched duplex DNA. The method comprises contacting a MutS homolog (MSH) dimer and the mismatched duplex DNA in the presence of a binding solution. The binding solution comprises either ADP and ATP, and the concentration of ATP in the binding solution is less than 5 micromolar, less than about 3 micromolar, 1 micromolar or less, preferably less than about 0.3 micromolar, and more preferably wherein the binding solution is substantially free of ATP. Alternately, ADP is used in the absence of ATP, or at least in excess with respect to ATP (i.e. ADP at a 2-fold, 10-fold, or 100-fold or greater excess relative to ATP). The MSH dimer thereby binds ADP. When the ADP-bound MSH dimer is contacted with the mismatched duplex DNA, the dimer associates with the mismatched region of the DNA, thus forming a modified mismatched duplex DNA.

The MSH dimer may be a homodimer or a heterodimer of any MutS homolog which is presently known to comprise or is discovered to comprise one or more which exhibits significant sequence similarity with at least one of Region I–V of human MSH2 (hMSH2), as described herein. The MutS homolog may be a prokaryotic MutS homolog or a eukaryotic MutS homolog. Preferably, the MutS homolog is a heterodimer, more preferably a heterodimer comprising MutS homologs obtained from a single species of organism. Thus, by way of example, the MSH dimer useful in the methods, kits, and compositions of the invention may be the *E. coli* MutS protein, an hMSH2 homodimer, a heterodimer comprising hMSH2 and either hMSH3 or hMSH6, a heterodimer comprising hMSH4 and hMSH5, a yeast MSH2 protein homodimer, a heterodimer comprising yeast MSH2 and either yeast MSH3 or yeast MSH6, a homodimer of a rat MSH2 (e.g. GenBank accession number X93591), a dimer of a Xenopus homolog of hMSH2 (Varlet et al., 1994, Nucl. Acids Res. 22:5723–5728), a homodimer of Drosophila MSH2 (e.g. GenBank accession number U17893), a homodimer of murine MSH2 (e.g. GenBank accession number X93591, Varlet et al., 1994, Nucl. Acids Res. 22:5723–5728), a heterodimer comprising murine MSH2 and either murine MSH3 (e.g. Rep-3; Linton et al., 1989, Mol. Cell. Biol. 9:3058–3072; Smith et al., 1990, Mol. Cell. Biol. 10:6003–6012) or murine MSH6 (e.g. Gen Bank accession number U42190), and the like. The MutS homolog of the MSH dimer used in the compositions, kits, and methods of the invention may also be any of the 41 MutS homologs and presently listed in the NCBI database. It is understood that, given the high degree of similarity among mammalian MutS homologs (Fishel et al., 1997, Curr. Op. Genet. Develop. 7:105–113), a dimer of any mammalian hMSH2 homolog can be used in the methods of the invention.

The mismatched duplex DNA molecule useful in the methods of the invention may be any duplex DNA molecule having at least one mismatched region. By way of example, the DNA molecule may be a linear DNA molecule, a circularized DNA molecule such as a plasmid or a viral genome, a chromosome, a cDNA generated by reverse transcription of an RNA molecule, a PCR primer, a PCR product, a complex formed between a single-stranded DNA probe and another single-stranded DNA molecule, and the like. The mismatched region may be any region of a duplex DNA molecule in which the two DNA strands of the molecule are not completely complementary. By way of example, the mismatched region may comprise one or more pairs of mismatched nucleotides in an otherwise complementary region of a duplex DNA molecule, a region of a duplex DNA molecule wherein a thymine dimer exists on one DNA strand of the molecule, a region of a duplex DNA molecule comprising a nucleotide which has been covalently modified by an agent capable of reacting with a nucleotide, such as cisplatin, a region of a duplex DNA molecule which comprises an alkyl-O-6-methyl guanine residue, a region of a duplex DNA molecule which comprises a single stranded loop of one or more nucleotides, a region of a duplex DNA molecule which comprises a pyrimidine dimer, and the like.

While any amount of ADP can be used in the binding solution of the method of the invention, it is preferred that the homolog be contacted with the mismatched duplex DNA in the presence of a binding solution comprising at least about 100 nanomolar ADP, preferably at least about 6 micromolar ADP, and more preferably at least about 60 micromolar ADP. As described with greater particularity in Example 1, ATP displaces ADP from the MSH dimer when the dimer is associated with a mismatched region of duplex DNA. Thus, it is important either that the concentration of ATP in the solution be minimized, for example by maintaining the concentration of ATP lower than about 3 micromolar, preferably lower than about 0.3 micromolar, and more preferably lower than about 10 nanomolar, or that the ratio of the concentration of ADP in the solution to the concentration of ATP in the solution be greater than a minimum value, such as about two, and preferably greater than about eight, and even more preferably greater than about sixteen. Preferably, the solution is substantially free of ATP or the ratio of ADP to ATP is much greater than sixteen (e.g. [ADP]:[ATP] is 100:1 or greater).

It is understood that gamma-hydrolysis-resistant ATP analogs, certain other ATP analogs, and other ADP analogs may be bound to an MSH dimer, and that these analog-bound dimers will associated with mismatched duplex DNA. By way of example, MSH2:MSH6 dimers will associate with mismatched DNA in the presence of either ATP-PNP or ATP-PCP.

The MSH dimer that is useful in the compositions, kits, and methods of the invention may be used in a variety of states of purity or isolation. For example, the dimer may be present in a liquid which a variety of other proteins, nucleic acids, lipids, single stranded nucleic acids, non-mismatched duplex DNA, and the like, it being understood that if the dimer is used in the form of a mismatched duplex DNA-containing liquid then it may be necessary to dissociate, and possibly to separate, the dimer from the mismatched DNA prior to using it in the compositions, kits, and methods of the invention. Preferably, the MSH dimer is substantially purified.

In many of the compositions, kits, and methods of the invention, the MSH dimer or the mismatched duplex DNA may bound to a support. Furthermore, each of the MSH dimer and the mismatched duplex DNA may be bound to different supports.

The MSH dimer or a MutS homolog of the dimer may be bound to a support using any known method for attaching a protein to a surface. For example the MutS homolog may be bound to a support by way of an antibody which is covalently bound to the support and which has a variable region which specifically binds to the MutS homolog. By way of example, an antibody which specifically binds to hMSH2 such as the antibody described by Kinzler et al. (PCT publication number WO96/41192) may be used to bind an hMSH2 protein dimer or a complex comprising an hMSH2 protein molecule and either an hMSH3 protein molecule or an hMSH6 protein molecule to a support to which the antibody is fixed. Methods of fixing an antibody to a support have been described in the art (e.g. Harlow et al., 1988, *Antibodies: A Laboratory Manual*, Cold Spring Harbor, N.Y.). Alternately, covalent, ionic, hydrophobic, or other types of bonding forces may be used to attach an MSH dimer or a MutS homolog to a support.

The duplex DNA molecule may be bound to a support using any known method for attaching a nucleic acid to a support. By way of example, the nucleic acid may be covalently linked to a biotin molecule and the support may be linked to or coated with a streptavidin molecule, whereby the streptavidin molecule is capable of binding the biotin molecule, thereby linking the nucleic acid to the support. Further by way of example, the duplex DNA may be covalently attached to a chemical substituent present on a surface of the support. Alternately, covalent, ionic, hydrophobic, or other types of bonding forces may be used to attach the duplex DNA to the support.

Supports to which an MSH dimer, a MutS homolog, or a duplex DNA molecule may be bound include any support known in the art for use in in vitro or in vitro biochemical or medical applications. By way of example, and not limitation, such supports include latex and other polymeric beads, particles, plates, supports, chromatography media, implants, drug delivery vehicles, metal and glass surfaces, gelatinous surfaces such as agarose, alginates, and polyacrylamides, and the like. It is important that the ability of the MutS homolog monomers or MSH dimers which are bound to the support be attached in such a way that the ability of the monomers to dimers to attain altered conformations is not significantly hindered. It is understood that, for example, by isolating antibodies which specifically bind to various epitopes on the monomer or dimer surface, a variety of antibodies may be isolated an used to bind monomers or dimers to a support. By assaying the ability of the support-bound monomers or dimers to bind to mismatched DNA in the presence of ADP, for example as described herein, an antibody or other support which attaches the monomers or dimers to a support without hindering their ability to bind mismatched duplex DNA may be identified. Such methods are routine in the art of protein immobilization and are not further described herein.

As disclosed herein, after an ADP-bound MSH dimer binds to a mismatched region of a duplex DNA, exchange of ATP for the ADP bound to the dimer results in release of the dimer from the mismatched region, whereby the ATP-bound dimer is enabled to diffuse to a different position on the DNA. If the dimer is able to diffuse to a free end of the duplex DNA, the dimer may dissociate from the duplex DNA.

If the duplex DNA does not have a free end, then ATP-bound dimer may diffuse away from the mismatched region of the duplex DNA, but may not dissociate from the DNA. Thus, if the duplex DNA does not have a free end, a plurality of copies of the dimer may be associated with the DNA in the presence of ATP. No upper limit is known for the number of dimers which may be associated with the DNA, but it is contemplated that this number is roughly proportional to the length of the duplex DNA. It is understood that association of multiple copies of an MSH dimer with a mismatched duplex DNA may be advantageous in situations in which association of the dimer with the DNA is to be detected. Multiple copies of the dimer may boost the detection limit of the DNA to be detected, increasing the signal-to-noise ratio of the detection method.

Duplex DNA not having a free end may be circular DNA or it may be linear DNA wherein both ends of the DNA are blocked. Ends of duplex DNA may be blocked by binding bulky moieties such as proteins to the DNA either directly (e.g. by covalently attaching the protein to the DNA or by binding the protein to the DNA non-covalently with high affinity) or via a linker (e.g. by biotinylating the DNA and binding an avidin such as streptavidin to the biotin moiety). Bulky moieties which may be used to block the ends of duplex DNA include, but are not limited to, proteins, supports, hairpin DNA structures, stem-and-loop DNA structures, and multiple a stem-and-loop DNA structures. Association of MSH dimers with DNA having one, two, or no free ends is expressly contemplated.

The mismatched duplex DNA to which an MSH dimer is to be bound may, for example, comprise a first DNA strand having a reference nucleotide sequence and a second DNA strand selected from the group consisting of a DNA strand obtained from an organism, a DNA strand obtained by amplification of at least a portion of a polynucleotide obtained from an organism, a DNA strand obtained by cleavage of a polynucleotide obtained from an organism, and a DNA strand obtained by reverse transcription of a polynucleotide obtained from an organism. By way of example, the second DNA strand may comprise at least a portion of a gene associated with a cancer in the organism. This gene may, for example, be any of a number of oncogenes and tumor suppressor genes which are known in the art. Examples of such genes include, for example, abl, akt2, apc, bcl2α, bcl2β, bcl3, bcr, brca1, brca2, cbl, ccnd1, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf1, wnt1, wnt2, wt1, and yes1. These genes are described in various publicly available databases, including the U.S. National Cancer Institute/National Center for Biotechnology Information Cancer Genome Anatomy Project database. Various accession numbers for these genes are listed in Table 1.

TABLE 1

| Gene Symbol | Entrez Accession | PubMed UID | UniGene CID | CGAP |
|---|---|---|---|---|
| ABL | X16416 | 90082420 | Hs.82576 | AA601510 |
| AKT2 | M95936 | 93028445 | Hs.37433 | AA505663 |
| APC | M74088 | 91335210 | Hs.75081 | AA592971 |
| BCL2ALPHA | M13994 | 86259760 | Hs.89534 | AA577385 |
| BCL2BETA | M13995 | 86259760 | Hs.99916 | |
| BCL3 | M31732 | 90199880 | Hs.31210 | AA527996 |
| BCR | Y00661 | 85240564 | Hs.2557 | AA592930 |
| BRCA1 | U14680 | 95025896 | Hs.66746 | AA484941 |
| BRCA2 | X95161 | 96112016 | Hs.34012 | AA215820 |
| CBL | X57110 | 92228506 | Hs.99980 | |
| CCND1 | M64349 | 91235304 | Hs.82932 | AA592929 |
| CDK4 | U37022 | 8528263 | Hs.95577 | AA483705 |
| CRK-II | D10656 | 92334347 | Hs.16 | |
| CSF1R/FMS | X03663 | 86175013 | Hs.75116 | AA595091 |
| DBL | X12556 | 89052660 | Hs.89543 | |
| DCC | X76132 | 95011532 | Hs.68149 | |
| DPC4/SMAD4 | U44378 | 96144684 | Hs.75862 | AA576881 |
| E-CAD | Z13009 | 93211394 | Hs.82004 | AA603448 |
| E2F1/RBAP | M96577 | 92346720 | Hs.89494 | |
| EGFR/ERBB-1 | X00588 | 84219729 | Hs.77432 | AA587386 |
| ELK1 | M25269 | 89203250 | Hs.1399 | AA576028 |
| ELK3 | Z36715 | 95047310 | | AA262193 |
| EPH | M18391 | 88070650 | Hs.1113 | |
| ERG | M17254 | 87263429 | Hs.70388 | |
| ETS1 | X14798 | 89083219 | | |
| ETS2 | J04102 | 89042086 | Hs.85146 | AA480196 |
| FER | J03358 | 89261786 | | AA534773 |
| FGR(SRC2) | M12502 | 85205090 | Hs.1422 | |
| FLI1/ERGB2 | M98833 | 93075640 | Hs.736 | |
| FOS | V01512 | 83221560 | Hs.25647 | AA514238 |
| FPS/FES | X06292 | 86055727 | Hs.7636 | |
| FRA1 | X16707 | 90191709 | Hs.4245 | |
| FRA2 | X16706 | 90191709 | Hs.89765 | AA601534 |
| FYN | M14333 | 86287278 | Hs.75390 | AA524156 |
| HCK | M16591 | 87257942 | Hs.77058 | |
| HEK | M83941 | 92179233 | | |
| HER2/ERBB-2/NEU | X03363 | 86118663 | Hs.46254 | AA508596 |
| HER3/ERBB-3 | M29366 | 90083234 | Hs.82186 | AA570304 |
| HER4/ERBB-4 | L07868 | 93189574 | Hs.1939 | |
| HRAS1 | V00574 | 83141783 | Hs.37003 | AA483837 |
| HST2 | X63454 | 92195660 | | |
| HSTF1 | J02986 | 87204251 | Hs.1755 | |
| INK4A | L27211 | 94081956 | Hs.1174 | AA557137 |
| INK4B | L36844 | 94359613 | | |
| INT2/FGF3 | X14445 | 89239468 | Hs.37092 | AA525331 |
| JUN | J04111 | 89057892 | Hs.78465 | AA582267 |
| JUNB | M29039 | 90090625 | Hs.89792 | AA503220 |
| JUND | X56681 | 91232849 | Hs.2780 | AA533575 |

TABLE 1-continued

| Gene Symbol | Entrez Accession | PubMed UID | UniGene CID | CGAP |
|---|---|---|---|---|
| KIP2 | D64137 | 96209909 | Hs.9039 | AA524076 |
| KIT | X06182 | 88111521 | Hs.81665 | AA552932 |
| KRAS2A | L00045 | 83271513 | | |
| KRAS2B | X01669 | 85087906 | | |
| LCK | X13529 | 89123626 | Hs.1765 | AA282059 |
| LYN | M16038 | 87172710 | Hs.80887 | AA524487 |
| MAS | M13150 | 86218084 | Hs.99900 | |
| MAX | M64240 | 91173288 | Hs.89500 | AA592936 |
| MCC | M62397 | 91164855 | Hs.1345 | |
| MET | J02958 | 87317655 | Hs.35379 | |
| MLH1 | U07343 | 8145827 | Hs.57301 | |
| MOS | J00119 | 82275068 | | |
| MSH2 | U04045 | 94084796 | Hs.78934 | AA502616 |
| MYB | M15024 | 87092302 | Hs.1334 | AA535078 |
| MYBA | X66087 | | Hs.2537 | AA459003 |
| MYBB | X13293 | 89083548 | Hs.74605 | AA603093 |
| MYC | X00196 | 84131953 | Hs.79070 | |
| MYCL1 | M19720 | 88094386 | Hs.92137 | |
| MYCN | Y00664 | 88202932 | Hs.25960 | AA548970 |
| NF1 | M89914 | 90335969 | Hs.37170 | AA534609 |
| NF2 | L11353 | 93201601 | Hs.902 | AA617825 |
| NRAS | X02751 | 85269641 | Hs.82602 | AA558915 |
| P53 | K03199 | 85267676 | Hs.1846 | AA514357 |
| PDGFB | M12783 | 87217119 | Hs.1976 | |
| PIM1 | M27903 | 90382681 | Hs.81170 | AA251525 |
| PTC | U59464 | 8658145 | Hs.54503 | |
| RAF1 | X03484 | 86120351 | Hs.85181 | AA578685 |
| RB1 | M15400 | 87149066 | Hs.75770 | AA594282 |
| REL | X75042 | 89330980 | Hs.44313 | AA279536 |
| RET | M16029 | 87257826 | Hs.6253 | |
| ROS1 | M34353 | 90280463 | Hs.1041 | |
| SKI | X15218 | 89345144 | Hs.2969 | AA258011 |
| SRC1 | M16243 | 87257903 | Hs.65442 | AA523427 |
| TAL1 | M29038 | 90099309 | Hs.73828 | AA551582 |
| TGFBR2 | M85079 | 92154690 | Hs.82028 | AA515322 |
| THRA1 | Y00479 | 88067793 | Hs.724 | AA602782 |
| THRB | X04707 | 87090375 | | AA577807 |
| TIAM1 | X86351 | 96129318 | Hs.3205 | |
| TRK | M23102 | 89181575 | Hs.85844 | |
| VAV | X16316 | 90005432 | | |
| VHL | L15409 | 93262488 | Hs.78160 | |
| WAF1 | L25610 | 94061996 | Hs.74984 | AA614342 |
| WNT1 | X03072 | 86055728 | | |
| WNT2 | X07876 | 89005063 | Hs.89791 | AA601910 |
| WT1 | X51630 | 90158822 | Hs.1145 | |
| YES1 | M15990 | 87172733 | Hs.75680 | AA502695 |

In a preferred embodiment, the gene associated with a cancer is a gene associated with hereditary non-polyposis colon cancer. For example, the gene may be selected from the group consisting of mlh1, msh2, msh3, msh6, pms1, and pms2. In another embodiment the gene may be a gene associated with a cancer selected from the group consisting of a leukemia, a lymphoma, a meningioma, a mixed tumor of a salivary gland, an adenoma, a carcinoma, an adenocarcinoma, a sarcoma, a dysgerminoma, a retinoblastoma, a Wilms' tumor, a neuroblastoma, a melanoma, and a mesothelioma.

If an MSH dimer is contacted with a mixture of mismatched duplex DNA and non-mismatched duplex DNA, the dimer will preferentially associate with the mismatched duplex DNA. The mismatched duplex DNA is thereby labeled differently than the non-mismatched duplex DNA, and MSH dimer associated with mismatched duplex DNA may be detected as describe herein or separated from the non-mismatched duplex DNA. By separating the dimer from non-mismatched duplex DNA, the mismatched duplex DNA bound to the dimer is separated from the non-mismatched duplex DNA. Furthermore, mismatched duplex DNA may be dissociated from the dimer after separating it from the non-mismatched duplex DNA.

Methods of detecting an MSH dimer associated with mismatched duplex DNA include, but are not limited to, electrophoretic gel mobility shift assays, HPLC and other column and thin layer chromatographic methods, filter binding assays, immunologic detection methods such as ELISA, tagged antibody, and precipitation assays, centrifugal sedimentation methods, optical affinity sensing, 'footprint' and other nucleolytic cleavage protection assays, and spectroscopic assays.

In a preferred method of detecting specific binding of the MutS homolog to the duplex DNA molecule, an optical affinity biosensor system (OABS) is used to detect specific binding. In an OABS system such as the IAsys™ system (Affinity Sensors, Cambridge, United Kingdom), binding and dissociation events can be detected as one molecule in solution binds to or dissociates from another molecule immobilized on a detector surface of the system. Thus, an OABS may be used to detect specific binding between an MSH dimer and a mismatched duplex DNA in any of the methods of the invention by immobilizing either the MSH dimer or the mismatched duplex DNA on the detector surface of the OABS. Specific binding may be differentiated from non-specific binding by comparing binding of an MSH dimer to a duplex DNA molecule known to comprise a mismatched region and binding of the homolog to a duplex DNA molecule known not to comprise a mismatched region.

By way of example, the separation of a mismatched duplex DNA from a population of duplex DNAs may be achieved by binding an MSH dimer to a support, contacting the support with the population of duplex DNAs, and rinsing the support with a separating solution which does not comprise the population of duplex DNAs. If the mismatched duplex DNA has a free end, then the separating solution is preferably substantially free of ATP. In this example, a mismatched duplex DNA in the population of duplex DNAs binds to the MSH dimer and thereby becomes associated with the support. The mismatched duplex DNA is segregated from the other duplex DNAs of the population by rinsing the support with the separating solution, which carries the non-mismatched DNA molecules away from the support. Thus, according to this example, the mismatched duplex DNA is physically separated from the non-mismatched duplex DNAs of the population.

It is not necessary that the just-described method result in separation of the mismatched duplex DNA from the population such that the molecule and the population are contained in different containers at the conclusion of the method. By way of example, it is sufficient in the OABS described herein that a mismatched duplex DNA comprising a region associate with the detector surface of the OABS and that non-mismatched duplex DNAs do not associate with the detector surface of the OABS. Thus, for example, in OABS methods for detection of mismatched duplex DNAs, an MSH dimer may be associated with the detector surface of the OABS, whereby a mismatched duplex DNA binds to the homolog in the presence of ADP and is detected, and whereby a non-mismatched duplex DNA does not bind appreciably to the dimer and is not detected.

Mismatched duplex DNA may be dissociated from an MSH dimer after separating the MSH dimer from a population comprising the mismatched duplex DNA and non-mismatched duplex DNAs. The mechanism by which this dissociation may be achieved depends upon whether or not the duplex DNA has a free end.

If the duplex DNA has a free end, then the an MSH dimer may be dissociated from the duplex DNA by contacting the dimer-mismatched duplex DNA complex with a solution having a high salt concentration, with a solution comprising EDTA or another magnesium-chelating agent, or with a releasing solution comprising ATP. Preferably, such a releasing solution comprises at least about 0.3 micromolar ATP, more preferably at least about 3 micromolar, more preferably at least about 30 micromolar ATP, and even more preferably much more than 30 micromolar ATP (e.g. 200 micromolar ATP or 500 micromolar ATP). If the mismatched duplex DNA has a free end, then the MSH dimer may be dissociated therefrom simply by contacting the dimer with a solution comprising ATP. The MSH dimer may also be dissociated from the mismatched duplex DNA by contacting the dimer-mismatched duplex DNA complex with a gamma-modified ATP analog.

If the mismatched duplex DNA does not have a free end, then an MSH dimer may be dissociated from the duplex DNA by contacting the dimer-mismatched duplex DNA complex with a solution which comprises high salt or EDTA or another magnesium-chelating agent. The dimer will not dissociate from the duplex DNA having no free end in the presence of ATP and magnesium ions (e.g. at least about 10 nanomolar $Mg^{2+}$, preferably at least about I micromolar $Mg^{2+}$, and more preferably at least about 100 micromolar $Mg^{2+}$. However, if a free end is generated on the mismatched duplex DNA, for example, by cleaving a circular DNA, by removing a blocking group from a blocked end of the DNA, or by cleaving the blocked end of the DNA, then the dimer will dissociate from the duplex DNA in the presence of ATP and magnesium ions. It is understood that there may be some situations in which association of MSH dimers is advantageous (e.g. separating DNA associated with MSH from DNA not associated with MSH). In such situations, taking advantage of the property of MSH dimers to exchange ADP→ATP only when a mismatch is present will permit association of multiple copies of the MSH dimer with the DNA, effectively increasing the amount of MSH dimer which can be detected using one or more of the methods described herein. This increase may be particularly important where the detection limit of the assay is relatively low.

Mismatched duplex DNA may be separated from a population of duplex DNAs by contacting the population and an MSH dimer and binding the MSH dimer to a support after contacting it with the population, but prior to separating the non-mismatched duplex DNA from the MSH dimer.

It is understood that if acceleration of ATP displacement of ADP bound to an MSH dimer or acceleration of ATP hydrolysis by MSH dimer not bound to duplex DNA is desired, the MSH dimer may be contacted with a MutL homolog to achieve this acceleration. It is furthermore understood that if the MSH dimer is present in molar excess with respect to the mismatched duplex DNA an average of more than one copy of the MSH dimer may be associated with individual copies of the mismatched duplex DNA if ATP is available to the MSH dimer. The average number of copies of the MSH dimer associated with individual copies of the mismatched duplex DNA may be further increased by contacting the MSH dimer with a MutL homolog. Similarly, the average number of copies of the MSH dimer associated with individual copies of the mismatched duplex DNA may be increased by employing solutions which favor formation of ADP-bound MSH dimer and displacement of ADP bound to mismatch-bound dimer by ATP. Such conditions include, but are not limited to, increasing the concentration ADP in the binding solution, increasing the concentration ATP, magnesium, or both, in the binding solution, and increasing the concentration of the dimer in the binding solution.

The properties of MSH dimers described above can be employed in a variety of useful methods including, but not limited to the following. It is understood that other methods which usefully employ the methods described above may be devised by the ordinarily skilled worker in view of the teachings provided herein.

The invention includes a method of segregating a mismatched duplex DNA from a population of DNA molecules. This method comprises contacting an MSH dimer and the population in the presence of a binding solution comprising a nucleotide selected from the group consisting of ADP and ATP. In the presence of this binding solution, the MSH dimer associates with the duplex DNA. After contacting the dimer and the population, the MSH dimer is segregated from the population. The duplex DNA is thereby segregated from the population.

The invention also includes a method of detecting a difference between a sample nucleotide sequence and a reference nucleotide sequence. This method comprises annealing a first DNA strand and a second DNA strand to form a duplex DNA. The first DNA strand has the sample nucleotide sequence, and the second DNA strand has a nucleotide sequence which is complementary to the reference nucleotide sequence. If there is a difference between the sample nucleotide sequence and the reference nucleotide sequence, then the duplex DNA will be a mismatched duplex DNA. After annealing the DNA strands, the duplex DNA and an MSH dimer are contacted in the presence of a binding solution as described herein. If the duplex DNA is a mismatched duplex DNA, then the MSH dimer associates with the duplex DNA. After contacting the duplex DNA and the MSH dimer, association of the MSH dimer with the duplex DNA molecule is detected as described herein. Association of the MSH dimer with the duplex DNA molecule is an indication that there is a difference between the sample nucleotide sequence and the reference nucleotide sequence.

The invention further includes a method of determining whether a mammal is predisposed for carcinogenesis. This method comprises annealing a first DNA strand and a second DNA strand to form a duplex DNA. The first DNA strand has the nucleotide sequence of at least a region of an oncogene or a tumor suppressor gene of the mammal, such as one of those described herein. The second DNA strand has a nucleotide sequence which is complementary to the consensus nucleotide sequence of this region. If there is a sequence difference between the first DNA strand and the second DNA strand, then the duplex DNA will be a mismatched duplex DNA. The duplex DNA is contacted with an MSH dimer in the presence of a binding solution as described herein. The MSH dimer associates with the duplex DNA if the duplex DNA is a mismatched duplex DNA. After contacting the duplex DNA and the MSH dimer, association of the MSH dimer with the duplex DNA molecule is detected as described herein. Association of the MSH dimer with the duplex DNA molecule is an indication that the mammal is predisposed for carcinogenesis.

The invention still further includes a method of fractionating a population of duplex DNAs. This method comprises contacting the population with an MSH dimer in the presence of a binding solution as described herein. The MSH dimer associates with any mismatched duplex DNA in the population. The MSH dimer is segregated from the population, and any mismatched duplex DNA from the population is segregated from the population. The population is thereby fractionated.

The invention also includes a method of selectively amplifying at least one mismatched duplex DNA of a population of duplex DNAs. This method comprises contacting the population with an MSH dimer in the presence of a binding solution as described herein. The MSH dimer associates with the mismatched duplex DNA. The MSH dimer is segregated from the population, and the mismatched duplex DNA is thereby segregated from the population. The mismatched duplex DNA is then amplified.

The invention further includes a method of determining whether the nucleotide sequence of a first copy of a genomic sequence differs from the nucleotide sequence of a second copy of the genomic sequence. This method comprises amplifying a region of each of the first copy and the second copy of the genomic sequence to yield amplified first copies and amplified second copies. The amplified first copies and the amplified second copies are mixed and denatured to form a first mixture. The nucleic acids in the first mixture are annealed to form a second mixture comprising duplex DNAs. If the nucleotide sequence of first copy and the nucleotide sequence of the second copy of the genomic sequence differ, then at least some of the duplex DNAs in the second mixture are mismatched duplex DNAs. The second mixture is contacted with an MSH dimer in the presence of a binding solution as described herein. The MSH dimer associates with any mismatched duplex DNAs that are present in the second mixture. Association of the MSH dimer with duplex DNA is then detected. Association of the MSH dimer duplex DNA is an indication that the nucleotide sequence of the first copy of the genomic sequence differs from the nucleotide sequence of the second copy of the genomic sequence. The first and second copies of the genomic sequence may be obtained from a single eukaryotic organism or from different eukaryotic individuals of the same or a different species. If the first and second copies of the genomic sequence are obtained from a single individual, one copy may be obtained from each of a pair of the individual's chromosomes. If the first and second copies of the genomic sequence are obtained from different individuals of the same species, then the individuals may, for example, be related, unrelated, or congenic.

The invention yet further includes a composition for segregating a mismatched duplex DNA from a population of duplex DNAs, the composition comprises an MSH dimer bound to a support, and may be used in any of the methods described herein. The composition may be a component of a kit which includes an instructional material which describes a method of the invention wherein the composition is useful. The kit may instead comprise the composition and a binding solution or a releasing solution, as described herein.

The invention also includes a kit for screening a genomic region for a nucleotide sequence which differs from a reference nucleotide sequence. This kit comprises a pair of primers complementary to the ends of the region. The pair of primers is useful for amplifying the region. The kit further includes a DNA strand having the reference nucleotide sequence and at least one MutS homolog. The MutS homolog may be supplied in the form of an MSH dimer. The kit may be used to perform the methods described herein. The kit may further comprise additional components, such as an instructional material which describes use of the kit to perform a method described herein, an assay reagent for detecting binding of a mismatched duplex DNA to the MSH dimer, or a reagent for blocking the ends of duplex DNAs. By way of example, the primers of the kit may be biotinylated and the kit may further comprise an avidin such as streptavidin for blocking the ends of duplex DNA.

The invention further includes a kit for separating a mismatched duplex DNA from non-mismatched duplex DNAs. This kit comprising at least one MutS homolog, a linker for binding the MutS homolog to a support, and an additional reagent selected from the group consisting of a nucleotide and a releasing solution, as described herein. The releasing solution may, for example, comprise a compound selected from the group consisting of ATP and a gamma-modified ATP analog. The kit may further comprise a reagent for blocking the ends of a duplex DNA, such as biotinylated PCR primers which can be used to amplify the duplex DNA, prior to contacting the biotinylated duplex DNA with an avidin such as streptavidin. Alternately, the kit may comprise a binding solution which is substantially free of ATP, magnesium ions, or both, whereby when a support-bound MSH dimer binds a mismatched duplex DNA, the dimer is not able to bind ATP and magnesium ion, and thus cannot exhibit DNA-associated diffusion and the duplex DNA remains bound to the ADP-bound dimer.

The invention further includes a nonhuman mammal which is nullizygous for both Msh2 and p53. The nonhuman mammal does not express Msh2 or p53 and exhibits a phenotype selected from the group consisting of inappropriate fetal apoptosis and a predisposition for carcinogenesis. Preferably, the mammal is a mouse, but other non-human mammals may also be generated using the teaching provided herein.

The invention still further includes a method of making a nonhuman mammal which is nullizygous for both Msh2 and p53. Such a mammal does not express Msh2 or p53 and exhibits a phenotype selected from the group consisting of a predisposition for inappropriate fetal apoptosis and a predisposition for carcinogenesis. Such mammals are made by mating a first parent mammal comprising at least one null allele of Msh2 and at least one null allele of p53 and a second parent mammal comprising at least one null allele of Msh2 and at least one null allele of p53. The offspring of the two parent mammals inherit the null alleles of these two genes according to normal allelic segregation rules (i.e. generally speaking, most mammals will randomly inherit one of each parent's two alleles of a gene). Thus, the proportion of nonhuman mammals which are nullizygous for both Msh2 and p53 will depend upon the allelic composition of the parents. Offspring which are nullizygous for both Msh2 and p53 do not express Msh2 or p53 and exhibit a phenotype selected from the group consisting of inappropriate fetal apoptosis and a predisposition for carcinogenesis. Further details relating to this method are described herein, such as in Example 2.

The invention also includes several screening methods, all of which make use of the properties of the $Msh2^{-/-}p53^{-/-}$ mice described herein.

A standard screening procedure is now described which is useful for determining the tumorigenesis-, apoptosis-, aging-, or fetal development-modulating potential of a compound. While this procedures is described with respect to particular protocols and mice, it will be appreciated that the screening procedure described should not be construed to limit the invention in any way.

$Msh2^{-/-}p53^{-/-}$ mice are generated as described herein or obtained from a producer of such mice. A predetermined amount of the compound is administered to a $Msh2^{-/-}p53^{-/-}$ mouse by any practical means. The method of administration of the compound is not critical. By way of example, the compound may be administered orally, intraperitoneally, intravenously, topically, intramuscularly, or via a pulmonary route.

Following administration of the compound, the $Msh2^{-/-}p53^{-/-}$ mouse, each $Msh2^{-/-}p53^{-/-}$ mouse is observed for about four months. Each mouse is examined approximately daily. Every week, each mouse is weighed, observed for any clinically-relevant symptoms, and the number and extent of tumors are assessed.

To reduce any potential for bias, the study is blinded. A first investigator treats all mice with compound(s) and identifiably marks or cages the transgenic mice, so that the nature of the treatments will not be known to a second investigator, who performs all tumor counts, weighing, and general observations.

If the mice are being used to screen for tumorigenesis-modulating compounds, then after observations are completed, the rate of tumor incidence and the tumor yield are determined for each group of $Msh2^{-/-}p53^{-/-}$ mice to which the compound was applied. A higher or lower rate of tumor incidence or a higher or lower tumor yield for a group of $Msh2^{-/-}p53^{-/-}$ mice to which the compound was applied, compared with the levels of tumor incidence and tumor yield for a group of $Msh2^{-/-}p53^{-/-}$ mice to which the compound was not applied, is an indication that the compound affects tumorigenesis.

If the mice are being used to screen for apoptosis-modulating compounds or fetal development-modulating compounds, then the mice are preferably administered the compound and observed during fetal development. After observations are completed, the prevalence of inappropriate fetal apoptosis and the fetal survival rate are determined for each group of $Msh2^{-/-}p53^{-/-}$ mouse embryos to which the compound was applied. A higher or lower mouse embryos or a higher or lower fetal survival rate for a group of $Msh2^{-/-}p53^{-/-}$ mouse embryos to which the compound was applied, compared with the mouse embryos and fetal survival rate for a group of $Msh2^{-/-}p53^{-/-}$ mouse embryos to which the compound was not applied, is an indication that the compound affects apoptosis or fetal development.

If the mice are being used to screen for aging-modulating compounds, then after observations are completed, the prevalence of at least one symptom of aging (e.g. graying of hair, other changes in coat color, lethargy, or hair loss) are determined for each group of $Msh2^{-/-}p53^{-/-}$ mice to which the compound was applied. A higher or lower prevalence of a symptom of aging for a group of $Msh2^{-/-}p53^{-/-}$ mice to which the compound was applied, compared with the prevalence of the symptom for a group of $Msh2^{-/-}p53^{-/-}$ mice to which the compound was not applied, is an indication that the compound affects aging.

Preferably, groups of $Msh2^{-/-}p53^{-/-}$ mice or embryos are used, with each mouse in a group being treated identically. Also preferred are studies in which one of at least three different dose levels of the compound are applied to the mice or embryos in each of at least three corresponding groups of transgenic mice. It is preferred, where possible, to demonstrate a statistically significant difference ($P<0.05$) between the observed phenotype for the first dose level and the observed phenotype for the third dose level.

A cell line may be made using cells obtained from a $Msh2^{-/-}p53^{-/-}$ mouse of the invention. Methods of making a cell line from a cell of a nonhuman animal are well known in the art.

The invention also includes a method of determining whether a composition interferes with the activity of one of the p53 gene or one of its expression products and a MutS homolog gene or one of its expression products. According to this method, non-human mammals such as mice are generated which are nullizygous for one of the p53 gene and the gene encoding the MutS homolog. These nullizygous animals are crossed to generate embryos which are also nullizygous for the same gene. The embryos are contacted with the composition, either in vitro or in utero, and the effects of contacting the embryos with the composition are observed. Increased mortality among the embryos, particularly among the female embryos, is an indication that the composition is able to interfere with the activity of the other of the p53 gene or one of its expression products and a MutS homolog gene or one of its expression products. Thus, the ability of a composition to increase female embryonic lethality in mouse embryos which are nullizygous for the p53 gene is an indication that the composition interferes with the activity of a MutS homolog gene or one of its expression products. Similarly, the ability of a composition to increase female embryonic lethality in mouse embryos which are nullizygous for a MutS homolog gene is an indication that the composition interferes with the activity of the p53 gene or one of its expression products. Preferably, female embryos are selected and used. Also preferably, female embryonic lethality is observed at about 9.5 days gestation. Methods of generating both nullizygous p53 animals such as mice and nullizygous msh gene animals such as mice have been described in the art.

The invention further includes a composition comprising a human MutS homolog fragment, wherein the fragment comprises a MutS homolog interaction region. The fragment may be a polypeptide having as many as all but one amino acid residues of the corresponding MutS homolog. The interaction region may be any of the MutS homolog interaction regions described herein or a MutS homolog interaction region having significant homology thereto. By way of example, a MutS homolog interaction region having significant homology to a MutS homolog interaction region described herein may exhibit at least about 50%, and preferably at least about 70%, 85%, 95%, or 99% homology with a MutS homolog interaction region described herein. Thus, by way of example, the interaction region may be completely or significantly homologous to amino acid residues 378–625 of hMSH2, amino acid residues 875–934 of hMSH2, amino acid residues 126–250 of hMSH3, amino acid residues 1050–1128 of hMSH3, amino acid residues 326–575 of hMSH6, or amino acid residues 1302–1360 of hMSH6.

The composition comprising a human MutS homolog fragment of the invention is useful in a method of inhibiting association of a first human MutS homolog and a second human MutS homolog. This method comprises contacting at least one of the first human MutS homolog and the second human MutS homolog with the human MutS homolog fragment of the invention. Without wishing to be bound by any particular theory of operation, it is believed that the fragment will interact with at least one interaction region of one human MutS homolog, thereby preventing that homolog from associating with the other MutS homolog. Such compounds would have utility for inducing apoptosis in animal cells (e.g. human tumor cells) which harbor one or more mutations in their p53 genes. Such compounds would also be useful for sensitizing animal cells which harbor one or more mutations in their p53 genes for further treatment using, for example, DNA-damaging agents.

As described herein in Example 5, cDNA encoding hMSH5 has been discovered, and a protein encoded by that cDNA has also been discovered. hMSH5 may be purified in a manner directly analogous to the methods described herein (e.g. by his-tagging) or by other methods well known in the art. The invention thus includes substantially purified hMSH5 and an isolated nucleic acid encoding hMSH5.

The invention is now described with reference to the following Examples. These Examples are provided for the purpose of illustration only and the invention should in no way be construed as being limited to these examples, but rather should be construed to encompass any and all variations which become evident as a result of the teaching provided herein.

EXAMPLE 1

The Human Mismatch Recognition Complex hMSH2:hMSH6 Functions as a Molecular Switch Adenine nucleotide binding by the human hMSH2:hMSH6 mismatch recognition complex functions as a novel molecular switch. The hMSH2:hMSH6 heterodimer is “ON” (i.e. it associates with mismatched DNA) in the ADP-bound form, and “OFF” (i.e. it is not capable of associating with mismatched DNA with which it is not already associated) in the ATP-bound form. The data presented herein establish that the switch is ‘turned OFF’ by displacement of complex-bound ADP by ATP. ATP-bound complex is recycled to the ADP-bound form, which is capable of binding to mismatched DNA, by intrinsic ATPase activity of the complex.

The materials and methods used in the experiments presented in this Example are now described.

Overexpression and Purification of hMSH2:hMSH6

Clones encoding hMSH2 and those encoding hMSH6 have been described (Acharya et al., 1996, Proc. Natl. Acad. Sci. USA 93:13629–13634; Fishel et al., 1993, Cell 75:1027–1038). In the experiments described herein, the clone encoding hMSH6 was modified to further encode six histidine residues at the amino terminus of the hMSH6 protein molecule. hMSH3 can be similarly modified and isolated.

hMSH2 and hMSH6 were overexpressed in SF9 insect cells using the pFastBac™ dual expression vector (Gibco BRL, Grand Island, N.Y.) as described in the Bac-to-Bac™ baculovirus expression systems protocol (Gibco BRL, Grand Island, N.Y.). Briefly, SF9 cells suspended in approximately 400 milliliters culture medium were infected using the vector, and were then cultured for 48 hours to achieve a cell density of approximately $10^6$ SF9 cells per milliliter. The cells contained in 200 milliliter aliquots of SF9 cells were harvested by centrifugation at 200×g, resuspended in 10 milliliters of buffer A, and frozen at −80° C. Buffer A comprised 300 millimolar NaCl, 20 millimolar imidazole, 25 millimolar HEPES buffer adjusted to pH 7.8 using NaOH, 10% (v/v) glycerol, 0.5 millimolar phenylmethylsulfonylfluoride (PMSF), 0.8 micrograms per milliliter pepstatin, and 0.8 micrograms per milliliter leupeptin.

Cell extracts were prepared by thawing the cells, passing the cells through a 25 gauge needle, and then ultracentrifuging the extract at 40,000 rotations per minute in a Beckman Ti60 rotor for 70 minutes, according to known methods. About 100 milliliters of infected cells yielded approximately 2 milligrams of hMSH2:hMSH6 protein complex. All of the following protein purification procedures in this Example were carried out at 4° C.

The supernatant was applied to a 2 milliliter nickel-NTA Superflow™ column (Qiagen, Chatsworth, Calif.) at a flow rate of 0.15 milliliters per minute using a Pharmacia FPLC system. The column was washed by passing 35 milliliters of buffer A through the column. After washing the column, the hMSH2:hMSH6 heterodimer was eluted by applying 30 milliliters of buffer A comprising a linear gradient of imidazole to the column and collecting the eluent from the column in fractions, wherein the concentration of imidizole was varied from 20 millimolar to 200 millimolar. The hMSH2:hMSH6 heterodimer eluted in fractions containing approximately 70 millimolar imidizole.

Fractions from the nickel-NTA column which contained peak amounts of the heterodimer were loaded at a flow rate of 0.2 milliliters per minute directly onto a 1 milliliter PBE 94 column (a polybuffer exchange column obtained from Pharmacia, Upsala Sweden) which had been equilibrated with buffer B. Buffer B comprised 300 millimolar NaCl, 25 millimolar HEPES buffer adjusted to pH 7.8 using NaOH, 1 millimolar dithiothreitol (DTT), 0.1 millimolar ethylenediaminetetraacetic acid (EDTA), 10% (v/v) glycerol, 0.5 millimolar PMSF, 0.8 micrograms per milliliter pepstatin, and 0.8 micrograms per milliliter leupeptin. The PBE 94 column was washed by passing 10 milliliters of buffer B through the column. After washing the column, the hMSH2/hMSH6 complex was eluted by applying 20 milliliters of buffer B comprising a linear gradient of NaCl to the column and collecting the eluent from the column in fractions, wherein the concentration of NaCl was varied from 300 millimolar to 1 molar. The hMSH2:hMSH6 heterodimer eluted from the PBE 94 column in fractions containing approximately 575 millimolar NaCl.

Fractions collected from the PBE 94 column which contained peak amounts of the heterodimer were dialyzed twice for two hours against 2 liters of a solution comprising 100 millimolar NaCl, 25 millimolar HEPES buffer adjusted to pH 7.8 using NaOH, 1 millimolar DTT, 0.1 millimolar EDTA, and 20% (v/v) glycerol. Aliquots of the dialyzed solution containing the heterodimer were frozen using liquid nitrogen and stored at −80° C. for several months without detectable loss of activity.

hMSH2, hMSH6, and bovine serum albumin (BSA) contain nearly identical percentages (12%, 14%, and 13%, respectively) of arginine and heterocyclic amino acids, the amino acids known to interact with the Coomassie Brilliant Blue stain. Protein concentration in an aliquot comprising the hMSH2:hMSH6 heterodimer was determined by subjecting a portion of the aliquot to SDS-PAGE using a 6% (w/v) acrylamide gel, subjecting a known amount of BSA (Boehringer Mannheim, Indianapolis, Ind.) to SDS-PAGE using a 6% (w/v) acrylamide gel, staining the SDS-PAGE gels with Coomassie Brilliant Blue, and comparing the intensities of the protein bands in the gels to a BSA standard on a Coomassie stained 6% SDS PAGE to calculate protein concentration. The intensities of stained protein bands were measured using BioRad Gel Doc and Molecular Analyst™ software. This protein quantitation method revealed the hMSH2 and hMSH6 proteins to be in near exact equimolar proportion in the heterodimer.

Preparation of 39- and 81-base Pair Oligonucleotide Probes

The sequence of the 39-base pair oligonucleotide used in the experiments presented in this Example was: 5'-CGGCGAATTC CACCAAGCTT GATCGCTCGA GGTACCAGG-3' (SEQ ID NO: 1). The homologous 39-base pair DNA substrate used in the experiments presented in this Example was made by annealing the 39-base pair oligonucleotide with an oligonucleotide (SEQ ID NO: 2) which was completely complementary thereto. The G/T mismatched 39-base pair DNA substrate used in the experiments presented in this Example was made by annealing the 39-base pair oligonucleotide with an oligonucleotide (SEQ ID NO: 3) which was completely complementary thereto, except that the oligonucleotide contained a G residue at the nucleotide position complementary to the T residue at position 20 (numbered in the direction extending from the 5' end to the 3' end) of the 39-base pair oligonucleotide. SEQ ID NO: 2 and SEQ ID NO: 3 are listed in FIG. 8.

The nucleotide sequence of the 81-base pair oligonucleotide used in the experiments described in this Example was: 5'-AAAGCTGGAG CTGAAGCTTA GCTTAGGATC ATCGAGGATC GAGCTCGGTG CAATTCAGCG GTAC-CCAATT CGCCCTATAG T-3' (SEQ ID NO: 4). The homologous 81-base pair DNA substrate used in the experiments presented in this Example was made by annealing the 81-base pair oligonucleotide with an oligonucleotide (SEQ ID NO: 5) which was completely complementary thereto. The G/T mismatched 81-base pair DNA substrate used in the experiments presented in this Example was made by annealing the 81-base pair oligonucleotide with an oligonucleotide (having the nucleotide sequence listed in SEQ ID NO: 6) which was completely complementary thereto, except that the oligonucleotide contained a T residue at the nucleotide position complementary to the G residue at position 41 (numbered in the direction extending from the 5' end to the 3' end) of the 81-base pair oligonucleotide. SEQ ID NO: 5 and SEQ ID NO: 6 are listed in FIG. 8.

$^{32}$P-end-labeled DNA substrates were prepared by incubating single stranded oligonucleotides in the presence of T4 polynucleotide kinase (Promega Corp., Madison, Wis.) and [$^{32}$P]γ-ATP (NEN Dupont, Wilmington, Del.). Excess label was separated from the labeled DNA substrates using a Centrisep™ column (Princeton Separations, Princeton, N.J.) per the manufacturer's instructions.

Labeled DNA substrate was annealed with a single-stranded DNA molecule which was either completely complementary thereto or contained a single G/T mismatch. To anneal the labeled DNA substrate with the single-stranded DNA molecule, the labeled molecule was suspended in a solution comprising a 10-fold excess of the single-stranded DNA molecule, 10 millimolar Tris buffer which had been adjusted to pH 7.5 using HCl, 100 millimolar NaCl, and 1 millimolar EDTA. The suspension was heated to 95° C. and then slowly cooled to 55° C. and was maintained at this temperature for twelve hours. Single-stranded DNA was removed from the suspension by incubating the suspension with benzoylated naphthoylated DEAE cellulose (BND cellulose, Sigma Chemical Co., St. Louis, Mo.) for twenty minutes in the presence of a solution comprising 1.5 molar NaCl, 20 millimolar Tris buffer which had been adjusted to pH 7.5 using HCl, and 0.5 millimolar EDTA. BND cellulose was then pelleted by centrifuging the suspension for about five minutes using an Eppendorf bench-top centrifuge. Double-stranded DNA, which remained in the supernatant, was separated from the BND cellulose by filtration and was then precipitated by adding ethanol to the supernatant. The double-stranded labeled DNA substrate was resuspended in a solution comprising 10 millimolar Tris buffer which had been adjusted to pH 7.5 using HCl, 100 millimolar NaCl, and 1 millimolar EDTA. Single-stranded DNA could not be detected in the solution, as assessed by 4% (w/v) native PAGE separation of the nucleotides in the solution. Non-$^{32}$P-labeled oligonucleotides were prepared using analogous methods.

Gel mobility Shift Assays

Gel mobility shift assays were performed by incubating a hMSH2:hMSH6 heterodimer and 9 femtomoles of either the $^{32}$P-labeled homologous 81-base pair DNA substrate or the $^{32}$P-labeled G/T-mismatched 81-base pair DNA substrate in a buffer comprising 50 millimolar NaCl, 25 millimolar HEPES buffer which had been adjusted to pH 7.5 using NaOH, 1 millimolar DTT, 0.01 millimolar EDTA, and 15% (v/v) glycerol. The buffer included 10 nanograms per microliter of poly dI-dC (Pharmacia LKB Biotechnology Inc., Piscataway, N.J.). Poly dI-dC is an alternating nucleic acid polymer which does not interfere with binding of the hMSH2:hMSH6 heterodimer to DNA. In certain experiments described herein, the incubation mixture further comprised selected concentrations of nucleotides or non-labeled DNA. In other experiments described herein, the incubation mixture further comprised 1 millimolar $MgCl_2$ or 5 millimolar EDTA. Except as otherwise described herein, each incubation mixture had a volume of 20 microliters and was incubated for fifteen minutes at 37° C. and then immediately placed on ice. Each incubation mixture was applied to a gel comprising 4% (w/v) polyacrylamide (29:1 ratio of acrylamide:bis-acrylamide) 4% (v/v) glycerol, 40 millimolar Tris acetate buffer (pH 7.8), and 1 millimolar EDTA. Electrophoresis was performed by applying 200 volts to the gel for two hours. Following electrophoresis, each gel was dried and quantitated using a phosphoimaging device obtained from Molecular Dynamics.

Footprint Assays

Incubation of the hMSH2:hMSH6 heterodimer with $^{32}P$-labeled DNA substrates was performed as described for gel mobility shift assays, except that 18 femtomoles of $^{32}P$-labeled DNA substrate was used in each assay. Following incubation, 80 microliters of a buffer comprising 50 millimolar NaCl, 25 millimolar HEPES buffer which had been adjusted to pH 7.8 using NaOH, 1 millimolar DTT, 10 nanograms per microliter poly dI-dC, 1.25 millimolar $CaCl_2$, 3.1 millimolar $MgCl_2$, 10% (v/v) glycerol, and 33 picograms per microliter DNase (Boehringer Mannheim, Indianapolis, Ind.) was added to each incubation mixture. The mixtures were incubated at 37° C. for an additional three minutes, and then 0.7 milliliters of a solution having a pH of 5.2 and comprising 95% (v/v) ethanol and 180 millimolar sodium acetate was added to each mixture to halt the DNase reaction and to precipitate the nucleic acids present in the mixture.

DNase-treated nucleic acids were resuspended in 4 microliters of a solution comprising 80% (v/v) formamide, 10 millimolar NaOH, 1 millimolar EDTA, and 0.1% (w/v) bromophenol blue. The suspension was heated at 90° C. for five minutes and was applied to a gel comprising 8% (w/v) polyacrylamide (29:1 ratio of acrylamide:bis-acrylamide), 90 millimolar tris-borate buffer (pH 8), and 2 millimolar EDTA. Following electrophoresis for 2 hours at 200 volts, each gel was dried and imaged on a phosphoimaging device. Individual bases of the 81-base pair DNA substrates were identified by Maxam-Gilbert sequencing reactions performed as described (Ausubel et al., 1994, Current Protocols in Molecular Biology, 8th Ed., Janssen, ed., John Wiley & Sons, Inc., Boston).

ATPase Assays

ATPase activity was measured in a reaction mixture comprising 20 microliters of Buffer P, 500 micromolar non-labeled ATP (except where indicated), and 16.5 nanomolar [$^{32}P$]γ-ATP. Buffer P comprised 40 millimolar HEPES which had been adjusted to pH 7.8 using NaOH, 75 millimolar NaCl, 10 millimolar $MgCl_2$, 1.75 millimolar DTT, and 0.075 millimolar EDTA, and 15% (v/v) glycerol. Steady state reaction measurements were made using 60 nanomolar hMSH2:hMSH6 heterodimer and either 240 nanomolar homoduplex 39-base pair DNA substrate or 240 nanomolar G/T mismatched 39-base pair DNA substrate. Reaction mixtures were incubated at 37° C. for thirty minutes, and the reaction was stopped by addition of 400 microliters of a solution comprising 10% (w/v) activated charcoal (Sigma Chemical Co., St. Louis, Mo.) and 1 millimolar EDTA. Charcoal was pelleted by centrifuging the mixture at 10,000 rotations per minute for ten minutes. The $^{32}P$ content of duplicate 100 microliter aliquots of the supernatant was assessed by liquid scintillation.

Initial velocity measurements were made by incubating the hMSH2:hMSH6 heterodimer for ten minutes at 25° C. in a reaction mixture comprising one volume Buffer P containing no $MgCl'_2$, 200 nanomolar non-labeled ATP, and 16.5 nanomolar [$^{32}P$]γ-ATP. To start the reaction, an equal volume of buffer P comprising 20 millimolar $MgCl_2$ and 1 millimolar non-labeled ATP was mixed with the reaction mixture, which raised the $MgCl_2$ and ATP concentrations to 10 millimolar and 500 micromolar, respectively. Aliquots were removed at selected times and electrophoresed as described herein. A control aliquot was removed and prepared for electrophoresis prior to addition of the $MgCl_2$-containing Buffer P to the reaction mixture.

ADP Exchange Assays

The ADP-ATP exchange rate was determined in a reaction mixture which comprised Buffer Q, 2.3 micromolar [$^3H$]-ADP, and 60 nanomolar hMSH2:hMSH6 heterodimer. Buffer Q comprised 25 millimolar HEPES which had been adjusted to pH 7.8 using NaOH, 75 millimolar NaCl, 10 millimolar $MgCl_2$, 1 millimolar DTT, and 15% (v/v) glycerol. This reaction mixture was incubated for ten minutes at room temperature. 240 nanomolar G/T-mismatched 39-base pair DNA substrate was added to the reaction mixture, and the incubation was continued for an additional ten minutes. The final volume of the reaction mixture was 10 microliters. The order of addition of DNA and ADP did not affect the kinetic results obtained using this assay. An equal volume Buffer Q comprising 1 millimolar non-labeled ATP was then added to the reaction mixture. Reactions were incubated at 25° C. for a selected time and then halted by diluting the reaction mixture with 4 milliliters of an ice-cold stop buffer comprising 25 millimolar HEPES which had been adjusted to pH 7.8 using NaOH, 100 millimolar NaCl, and 10 millimolar $MgCl_2$.

Each halted reaction mixture was immediately filtered on a HAWP nitrocellulose membrane (Millipore, Bedford, Mass.) and washed thrice with 4 milliliters of the ice-cold stop buffer. Each filter was air dried and incubated overnight in a standard scintillation cocktail. Radioactivity retained on the filters was quantified using a Beckman scintillation counter. A control reaction mixture was prepared by not adding the Buffer Q comprising 1 millimolar non-labeled ATP to the reaction mixture. The amount of [$^3H$]-ADP retained on the membrane to which the control reaction mixture was applied was considered to correspond to the amount of radioactivity retained when 100% of the complex had [$^3H$]-ADP bound thereto.

Thin Layer Chromatography (TLC) Analysis

TLC was used to determine the composition of an ATPase reaction mixture which was prepared as described herein in the presence of the G/T-mismatched 39-base pair DNA substrate, 15 micromolar ATP, and 0.01 micromolar [$^{32}P$] α-ATP and which was permitted to react for twenty minutes at 37° C. TLC was performed as previously described (Fishel et al., 1988, Proc. Natl. Acad. Sci. USA 85:36–40).

The results of the experiments presented in this Example are now described.

Overexpression and Purification of the hMSH2-hMSH6 Protein Complex hMSH2 and hMSH6 proteins were overexpressed in insect cells using a dual expression baculovirus vector, as assessed by the SDS-PAGE analysis of proteins obtained from cell extract. Co-expression of hMSH2 and hMSH6 proteins resulted in formation of a completely soluble hMSH2:hMSH6 heterodimer. Independent expression of either protein alone resulted in formation of a substantial amount of insoluble protein product. hMSH2 and hMSH6 likely exist together as a highly stable complex in vivo, as judged by the results obtained in the experiments described in this Example, the ability of investigators to co-purify these two proteins from human cells (Drummond et al., 1995, Science 268:1909–1912), and the ability of these two proteins to interact in vitro (Acharya et al., 1996, Proc. Natl. Acad. Sci. USA 93:13629–13634).

Purification of hMSH2 and hMSH6 from insect cells indicated that a stable heterodimer of the two proteins had been formed. Quantitative densitometry of Coomassie-stained products consistently revealed that the hMSH2 and hMSH6 subunits were present in an equimolar ratio, as was observed with the yeast MSH2:MSH6 protein complex (Alani et al., 1997, Mol. Cell Biol. 17:2436–2447). The purification methodology described herein yielded a protein preparation which was more than 95% homogeneous, which exhibited high MSH2/MSH6 activity, and which appeared to be free of any contaminating nucleic acid or nucleotide.

G/T Mismatch Binding by hMSH2:hMSH6 is a Model for Mismatch Recognition

The hMSH2:hMSH6 heterodimer has been demonstrated herein and by others to bind to the eight possible mismatched nucleotide combinations, as well as to a subset of single nucleotide insertion/deletion mismatches (Acharya et al., 1996, Proc. Natl. Acad. Sci. USA 93:13629–13634; Drummond et al., 1995, Science 268:1909– 1912; Hughes et al., 1992, J. Biol. Chem. 267:23876–23882). The G/T mismatch was chosen as a model for quantitative analysis of hMSH2:hMSH6 mismatch binding because of its apparently intermediate-to-high recognition specificity, as indicated, for example, by the data presented in FIGS. 1A–1D.

Figure 1A:
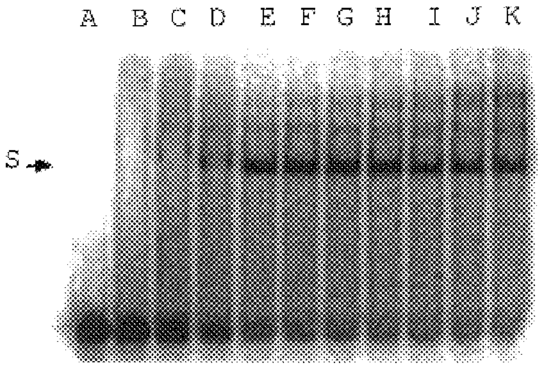
FIG. 1A is an image of the results of a gel mobility shift assay performed using the G/T-mismatched 81-base pair duplex DNA substrate described herein. The concentrations of heterodimer used in the assay were, in nanomolar, 0 in A, 6 in B, 19 in C, 32 in D, 64 in E, 97 in F, 129 in G, 161 in H, 193 in I, 257 in J, and 322 in K. The position of the S-shifted electrophoretic band is indicated by "S".

The apparent dissociation constant ($K_d$) was determined in a simple buffer system comprising neither an adenine nucleotide nor magnesium using the homologous 81-base pair DNA substrate and the G/T-mismatched 81-base pair DNA substrate described herein. Results obtained using both gel shift assays, as depicted in FIG. 1A, and DNase footprint assays, as depicted in FIG. 1C, indicated that $K_d$ of the hMSH2:hMSH6 heterodimer for G/T mismatches was 20±5 nanomolar. Binding of non-mismatched DNA to the heterodimer was not saturable, even at homoduplex concentrations greater than 400 nanomolar.

The binding of the hMSH2:hMSH6 heterodimer to a G/T mismatch is at least ten times more efficient than binding of hMSH2 alone to the G/T mismatch (Fishel et al., 1994, Science 266:1403–1405; Fishel et al., 1994, Cancer Res. 54:5539–5542; Mello et al., 1996, Chemistry & Biology 3:579–589). This observation indicates that formation of the hMSH2:hMSH6 heterodimer enhances both the affinity and the specificity of hMSH2-binding to mismatched DNA (Acharya et al., 1996, Proc. Natl. Acad. Sci. USA 93:13629–13634).

Gel mobility shift assays performed using the G/T-mismatched 39-base pair DNA substrate described herein or using the G/T-mismatched 81-base pair DNA substrate and a buffer comprising 2 millimolar $MgCl_2$ yielded results similar to those shown in FIG. 1A. The hMSH2:hMSH6 heterodimer appears to bind G/T mismatched DNA in multiple forms which are differentiable by gel mobility shift assay.

DNase footprint analysis of hMSH2:hMSH6 heterodimer binding to the G/T-mismatched 81-base pair DNA substrate indicated that the complex asymmetrically protects about 25 nucleotides on both strands of the substrate. As shown in FIG. 1C, there appeared to be two domains protected by the complex from cleavage by DNase. One domain appeared to be centered on the G/T mismatch in the substrate. The other domain was adjacent the domain centered on the G/T mismatch and was separated from that domain by a single DNase-sensitive nucleotide. These data are qualitatively similar to those observed in similar experiments using the *E. coli* and *T. aquaticus* MutS proteins (Su et al., 1986, Proc. Natl. Acad. Sci., USA 83:5057–5061; Su et al., 1988, J. Biol. Chem. 263:6829–6835; Biswas et al., 1997, J. Biol. Chem. 272:13355–13364).

Figure 1B:
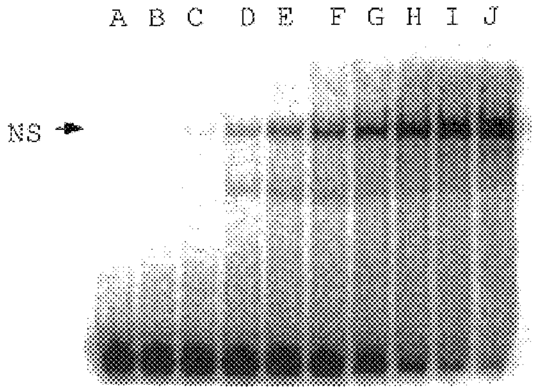
FIG. 1B is an image of the results of a gel mobility shift assay performed using the homologous 81-base pair duplex DNA substrate described herein. The concentrations of heterodimer used in the assay were, in nanomolar, 0 in A, 6 in B, 19 in C, 32 in D, 64 in E, 129 in F, 225 in G, 322 in H, 386 in I, and 482 in J. The position of the NS-shifted electrophoretic band is indicated by "NS".
Figure 1C:
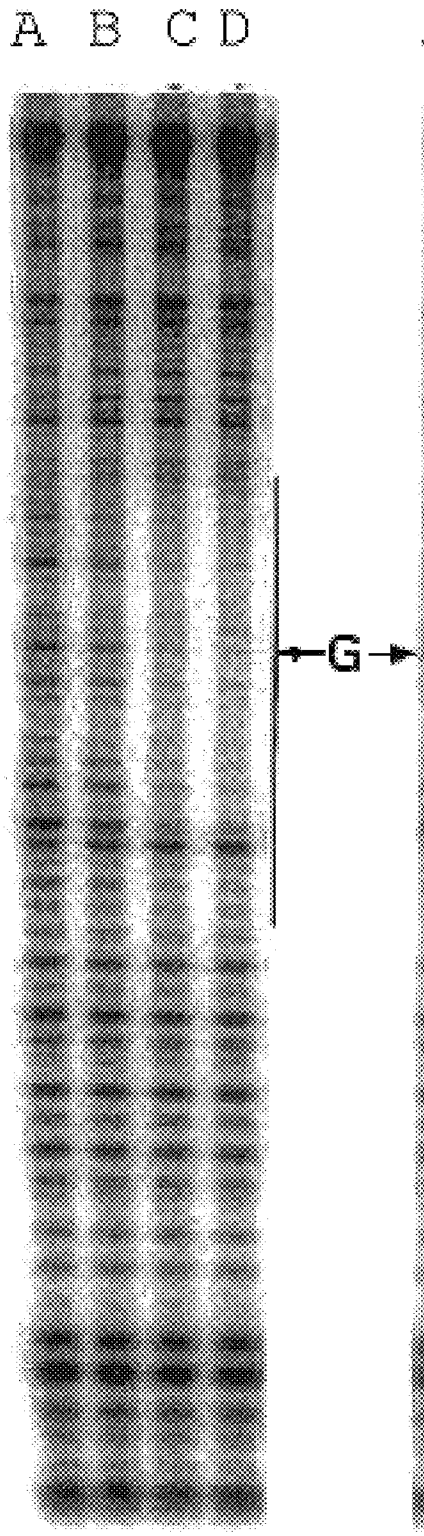
FIG. 1C is an image which depicts the results of a DNase footprint assay performed using the 81-base pair G/T-mismatched duplex DNA substrate described herein. The concentrations of 81-base pair were, in nanomolar, 0 in A, 13 in B, 32 in C, and 97 in D. The position of the G residue of the G/T-mismatched substrate is indicated by "G", and the approximate region of the substrate protected from DNase cleavage by the heterodimer is indicated by a vertical line.
Figure 1D:
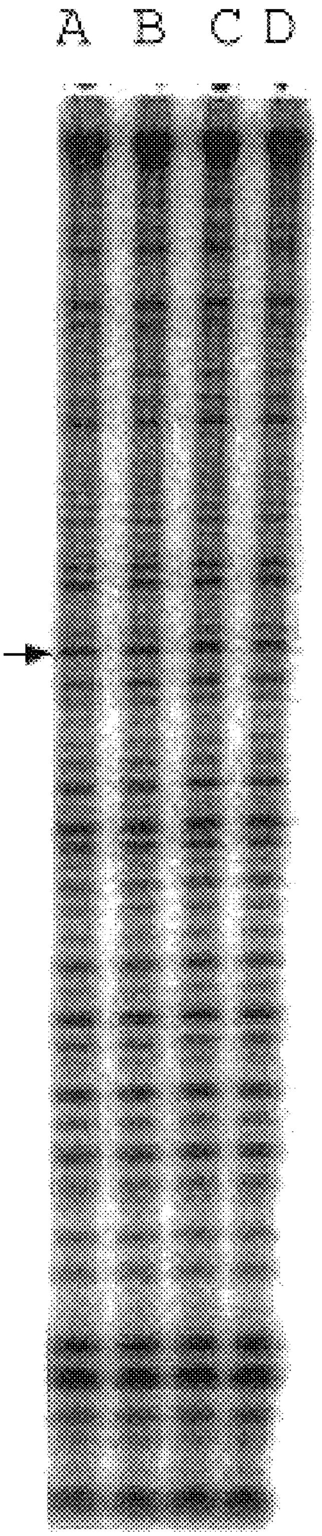
FIG. 1D is an image which depicts the results of a DNase footprint assay performed using the homologous 81-base pair duplex DNA substrate described herein. The concentrations of heterodimer used in the assay were, in nanomolar, 0 in A, 161 in B, 322 in C, and 482 in D. The position of the G/C base pair corresponding to the G/T-mismatched base pair of the mismatched substrate is indicated by "G".
Figure 1E:
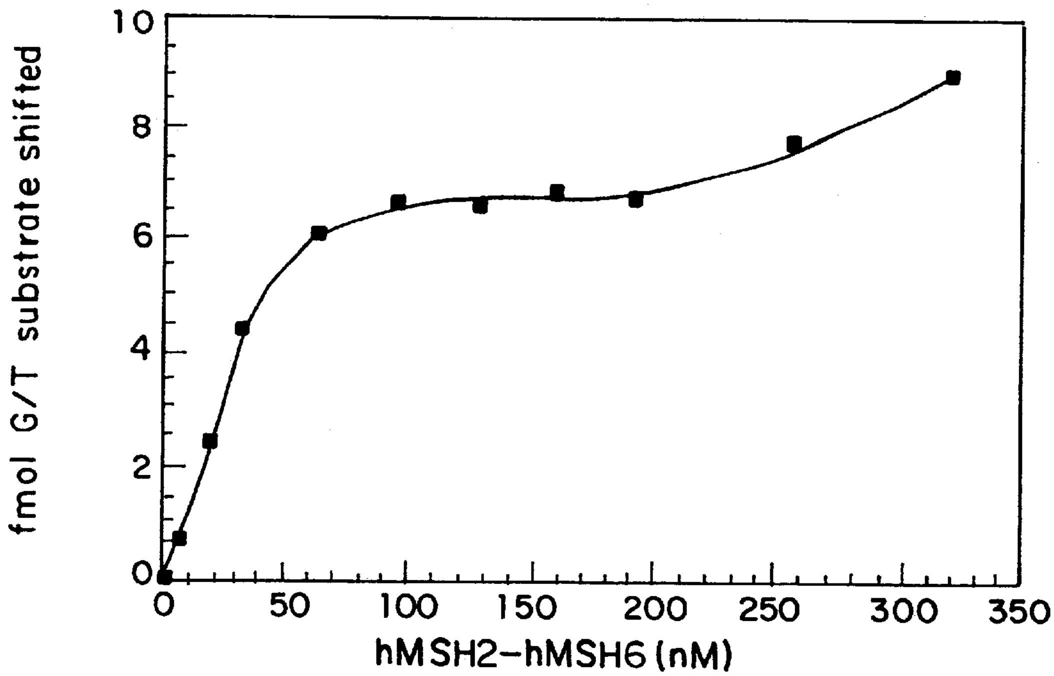
FIG. 1E is a graph which depicts the relationship between the concentration of heterodimer and the amount of product corresponding to the S-shifted electrophoretic band in FIG. 1A, as assessed using a phosphoimaging device.
Figure 1F:
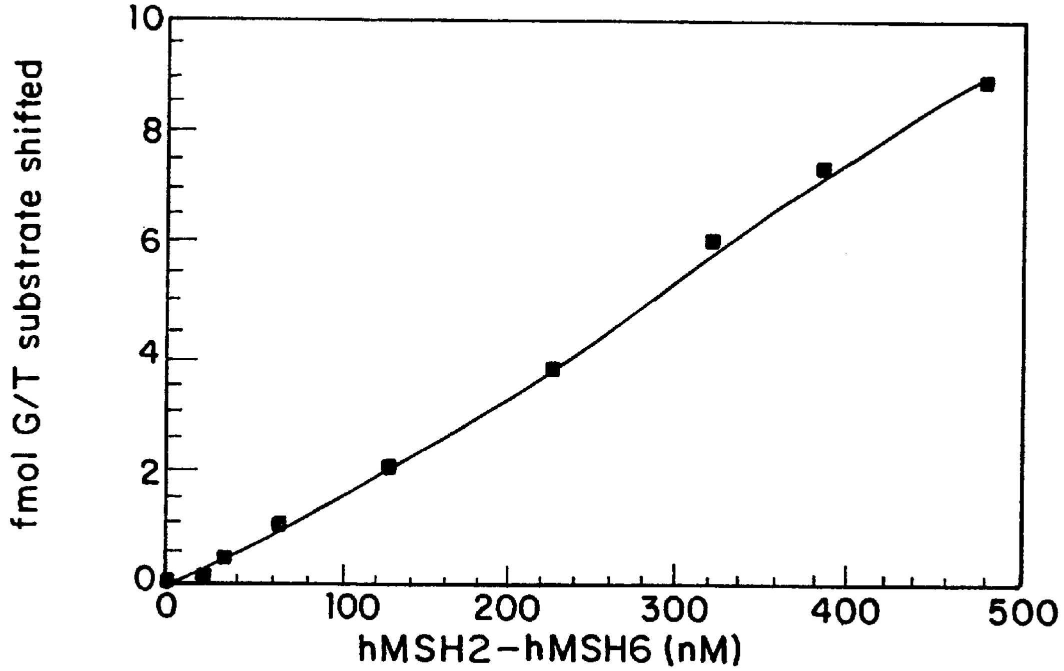
FIG. 1F is a graph which depicts the relationship between the concentration of heterodimer and the amount of product corresponding to the NS-shifted electrophoretic band in FIG. 1B, as assessed using a phosphoimaging device.

Although a shifted complex could be detected by gel mobility shift assay using homoduplex DNA, no specific DNase footprint could be identified, as indicated by the data presented in FIG. 1D. Lack of saturatability and lack of a specific footprint are consistent with the ability of the hMSH2:hMSH6 heterodimer to weakly and non-specifically associate with homoduplex DNA.

Shifted complexes formed between the heterodimer and homoduplex DNA and those formed between the heterodimer and G/T-mismatched DNA migrated differently in gel mobility shift assays, as shown in FIGS. 1A and 1B. Homoduplex DNA-bound heterodimer (designated 'NS' for 'non-specific' in FIG. 1B) migrated more slowly than G/T-mismatched DNA-bound heterodimer (designated 'S' for 'specific' in FIG. 1A). These results suggest that homoduplex DNA-bound heterodimer adopts a different conformation than mismatched DNA-bound heterodimer. Alternatively, there may have been a greater quantity of the heterodimer bound to homoduplex DNA than to mismatched DNA.

When the homoduplex 39-base pair DNA substrate described herein was contacted with the heterodimer, no NS product was observed in the gel mobility shift assay. The DNA length dependence of NS product formation may result if a minimum number of base pairs were necessary to assume an alternative DNA and/or hMSH2- or hMSH6-protein conformation or to bind multiple hMSH2:hMSH6 heterodimers.

These results demonstrate the high specificity of heterodimer binding to the G/T-mismatched 81-base pair DNA substrate. The binding was found to be quantitatively similar by both gel mobility shift and footprint analysis. In addition, a low level non-specific binding to duplex DNA was observed and found to be easily distinguished via its altered mobility using gel mobility shift analysis.

The hMSH2:hMSH6 Heterodimer Converts ATP to ADP in the Presence of Mismatched DNA Both bacterial and yeast MutS homologs have been shown to possess intrinsic low-level ATPase activity (Alani et al., 1997, Mol. Cell Biol. 17:2436–2447; Chi et al., 1994, J. Biol. Chem. 269:29993–29997; Chi et al., 1994, J. Biol. Chem. 269:29984–29992; Habe et al., 1988, J. Bacteriol. 170:197–202). There are conflicting reports regarding the capacity of mismatched heteroduplex and/or homoduplex DNA to stimulate this intrinsic ATPase activity (Alani et al., 1997, Mol. Cell Biol. 17:2436–2447; Chi et al., 1994, J. Biol. Chem. 269:29993–29997; Chi et al., 1994, J. Biol. Chem. 269:29984–29992).

It was demonstrated in the experiments described in this Example that the hMSH2:hMSH6 heterodimer possesses intrinsic DNA-dependent ATPase activity that is dependent upon the presence of magnesium as a cofactor. Saturation of the ATPase activity by hMSH2:hMSH6 heterodimer which was observed at protein concentrations above 0.6 micromolar was likely the result of a limiting amount of DNA, which was use at a fixed concentration of 240 nanomolar in the assay.

Thin layer chromatography revealed that hMSH2:hMSH6 heterodimer ATPase activity uniformly converts ATP to ADP and inorganic phosphate. Using Lineweaver-Burk analysis and Eadie-Hofstee analysis, it was determined that hMSH2:hMSH6 heterodimer ATPase is most active in the presence of a G/T mismatch. The value of $k_{cat}$ using ATP and G/T-mismatched DNA as substrates was about 26 minute$^{-1}$. The value of $K_m$ using ATP and G/T-mismatched DNA as substrates was about 46 micromolar. hMSH2:hMSH6 heterodimer ATPase is substantially less active in the presence of homoduplex DNA. The value of $k_{cat}$ using ATP and G/C-mismatched DNA as substrates was about 7.4 minute$^{-1}$. The value of $K_m$ using ATP and G/C-mismatched DNA as substrates was about 23 micromolar. hMSH2:hMSH6 heterodimer ATPase is substantially inactive in the absence of DNA. The value of $k_{cat}$ using ATP alone as a substrate was about 0.9 minute$^{-1}$. The value of $K_m$ using ATP alone as a substrate was about 10 micromolar.

ATPase activity stimulation was the same regardless of whether the homoduplex DNA had a length of 39 base pairs, 81 base pairs or 2,900 base pairs, and was also the same regardless of whether the mismatched DNA had a length of 39 base pairs or 81 base pairs. These results indicated that hMSH2:hMSH6 heterodimer ATPase activity is not dependent upon DNA length.

It was observed that $k_{cat}$ using ATP alone as a substrate was lower than $k_{cat}$ using ATP and homoduplex DNA as a substrate and this value was lower than $k_{cat}$ using ATP and mismatched DNA as substrates. However, $K_m$ for ATP in the absence of DNA was lower than $K_m$ for ATP in the presence of homoduplex DNA, and this value was lower than $K_m$ for ATP in the presence of mismatched DNA. These observations indicated that although the rate of hydrolysis is increased in the presence of a mismatch, the affinity for ATP is decreased. These results are qualitatively similar to the phenomenon of uncompetitive inhibition which may be ascribed to the presence of independent and separate binding sites as well as a ping-pong binding mechanism (Dixon et al., 1979, Enzymes, 3rd Ed., Academic Press, New York).

Single-stranded DNA (ssDNA) was determined to be the most potent stimulator of hMSH2:hMSH6 heterodimer ATPase activity. Thus, the conflicting reports in the prior art regarding ATPase activities of related MutS homologues may have resulted from contamination by ssDNA leached from columns used to purify the homologues and/or by non-annealed ssDNA that remained following preparation of oligonucleotide substrates.

hMSH2:hMSH6 Heterodimer Mismatch Binding is Abolished in the Presence of ATP in the Absence of Hydrolysis of ATP Both bacterial and eukaryotic MutS homologs have been reported to fail to form a specific complex with a mismatched oligonucleotide in the presence of ATP (Drummond et al., 1995, Science 268:1909–1912; Haber et al., 1991, EMBO. J. 10:2707–2715; Alani et al., 1997, Mol. Cell Biol. 17:2436–2447; Grilley et al., 1989, J. Biol. Chem. 264:1000–1004). Before the present invention, it was believed that ATP hydrolysis catalyzed by MutS protein drove translocation of the protein along a duplex DNA strand, causing dissociation of the protein from any mismatch with which it might be associated (Grilley et al., 1989, J. Biol. Chem. 264:1000–1004; Modrich, 1989, J. Biol. Chem. 264:6597–6600; Modrich, 1991, Annu. Rev. Genet. 25:229–253; Modrich et al., 1996, Annu. Rev. Biochem. 65:101–133; Allen et al., 1997, EMBO J. 16:4467–4476). The suggestion that ATP hydrolysis was required for the mismatch release was based on the observation by others that adenylyl-imidodiphosphate (AMP-PNP), a non-hydrolyzable analog of ATP, does not alter mismatch binding (Alani et al., 1997, Mol. Cell. Biol. 17:2436–2447; Drummond et al., 1995, Science 268:1909–1912).

Figure 2A:
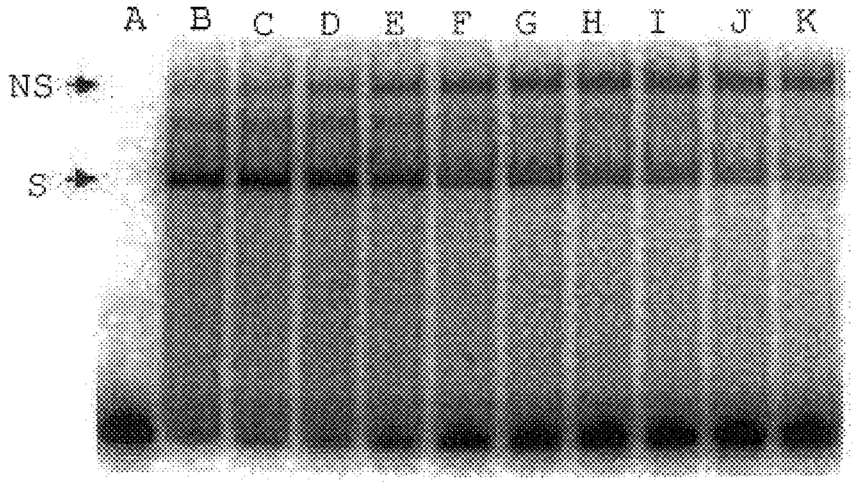
FIGS. 2A, 2B, 2C, and 2D, depicts the results of gel mobility shift assays used to assess the ability of various adenine nucleotides to dissociate MSH dimer from the mismatch site, corresponding to the S-shifted electrophoretic band, such that the MSH dimer, corresponding to the NS-shifted electrophoretic band, exhibited DNA-associated diffusion.
Figure 2B:
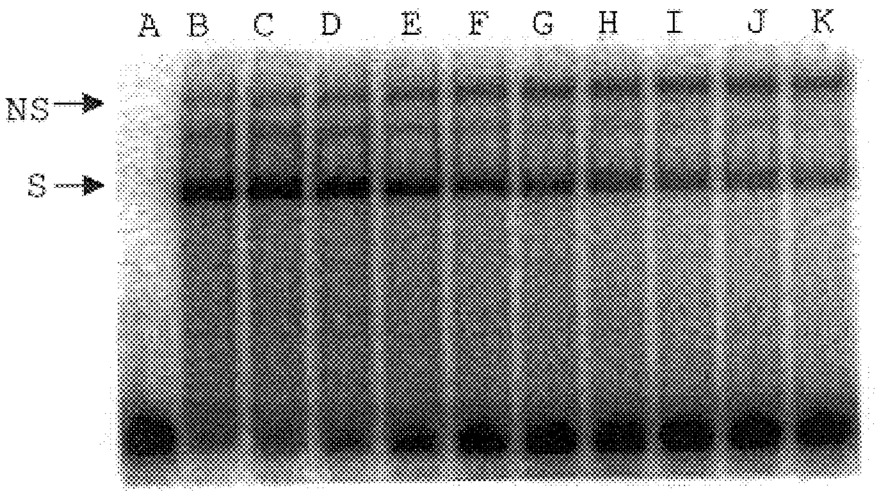
Figure 2C:
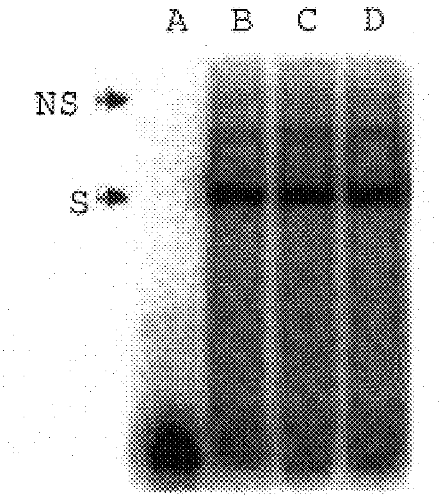
Figure 2D:
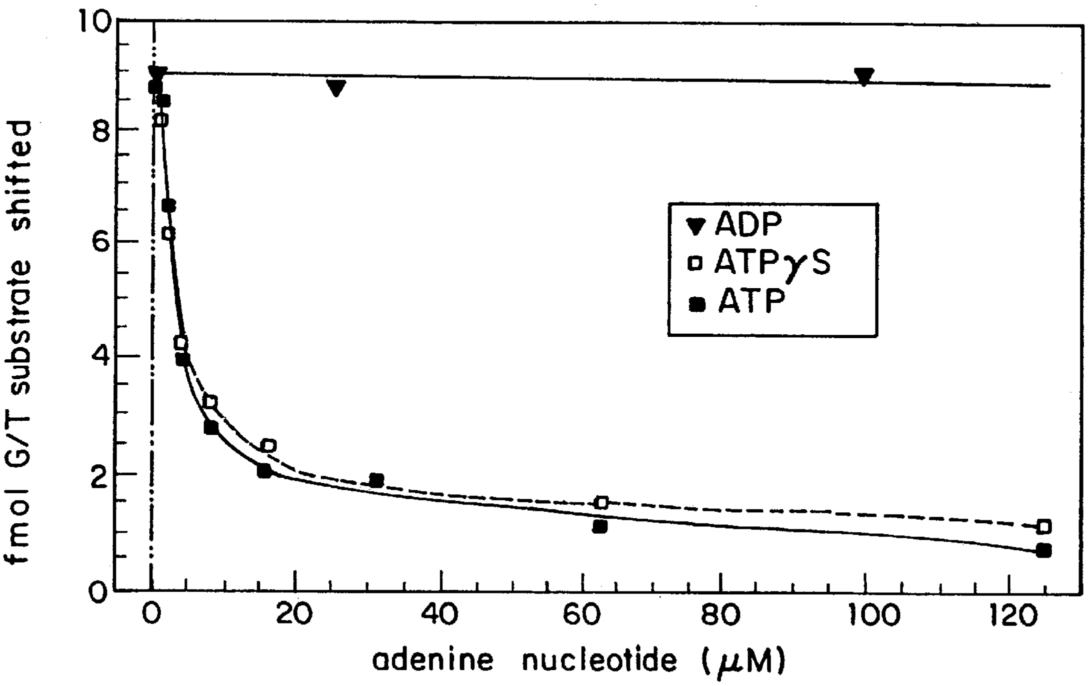

The experiments described in this Example establish that the hMSH2:hMSH6 heterodimer is released from a G/T-mismatched DNA substrate in the presence of ATP, as indicated in FIGS. 2A and D. The value of $IC_{50}$ (the concentration of ATP required to cause release of 50% of a population of heterodimers from a G/T-mismatched DNA substrate) was determined to be approximately 3 micromolar. Adenosine-5'-O-3-thiotriphosphate (ATP-γ-S), a poorly-hydrolyzable ATP analog (Sekimizu et al., 1987, Cell 50:259–265; Yu et al., 1992, J. Mol. Biol. 225:193–216), caused a similar release of the hMSH2:hMSH6 heterodimer from a G/T-mismatched DNA substrate, the value of $IC_{50}$ for ATP-γ-S being 3 micromolar, as indicated in FIGS. 2B and 2D. Addition of ADP to the mismatch binding reaction mixture resulted increased binding affinity of the heterodimer for the G/T-mismatched DNA substrate, as indicated in FIGS. 2C and 2D.

The results presented in this Example demonstrate that release of the hMSH2:hMSH6 heterodimer from a G/T-mismatched DNA substrate with which it is associated is not dependent upon ATP hydrolysis. This conclusion follows from the observations that release of the complex occurs in the absence of exogenous magnesium and that release of the complex from the substrate is effected by the presence of ATP-γ-S regardless of the presence or absence of magnesium. The presence of magnesium is absolutely required for hMSH2:hMSH6 heterodimer-dependent ATP hydrolysis. Furthermore, NS binding of hMSH2 to homoduplex DNA is insensitive to the addition of exogenous ATP. Thus, the presence of ATP affects only the ability of the hMSH2:hMSH6 heterodimer to bind to mismatched DNA substrates. Binding of the heterodimer to homoduplex DNA is not affected by ATP.

Figure 3:
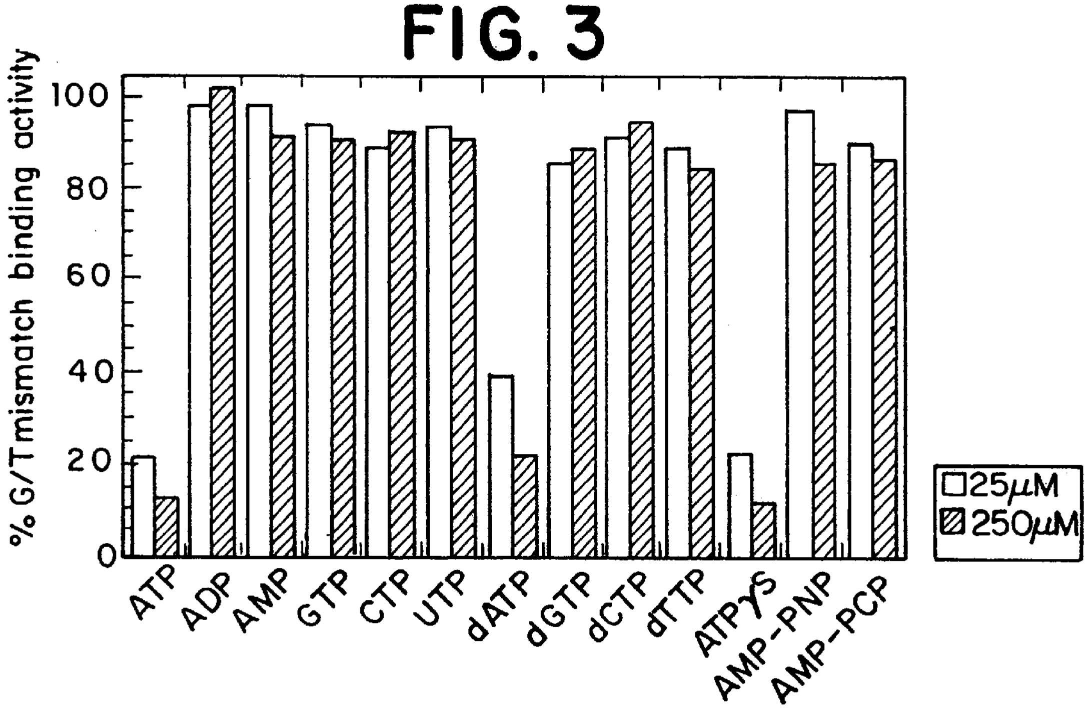
FIG. 3 is a bar graph which depicts the effect of selected nucleotides, deoxynucleotides, and nucleotide analogs on G/T mismatch binding by the heterodimer, relative to the degree of binding observed in the absence of a (deoxy) nucleotide or analog. The effect of each indicated (deoxy) nucleotide or analog was assessed at 25 micromolar (left bar of each pair) and at 250 micromolar (right bar of each pair).

The presence of 2'-deoxy adenosine triphosphate (DATP) to the mismatch binding reaction mixture caused release of a G/T-mismatched DNA substrate from the hMSH2:hMSH6 heterodimer, similarly to the release caused by the presence of ATP or ATP-γ-S in the mixture, as illustrated in FIG. 3. No other nucleotide was found to stimulate the release of the G/T-mismatched DNA substrate from the heterodimer.

Neither of two other non-hydrolyzable analogs of ATP, namely AMP-PNP and adenyl-(β-, γ-methylene)-diphosphonate (AMP-PCP), caused release of the heterodimer from the substrate. Equilibrium competition between each of these two analogs and ATP suggested that they bind to the heterodimer and caused effects similar to those caused by ADP. Failure of AMP-PNP and AMP-PCP to stimulate release of mismatched DNA from the heterodimer demonstrated that the interaction between the β-γ bridging oxygen atom of ATP and either the heterodimer or the mismatched DNA substrate bound to the heterodimer are for release of the substrate from the heterodimer. Enzyme-nucleotide triphosphate complexes in which the β, γ oxygen atom interacts with either the enzyme or its substrate are not unknown. For example, the Ras GTPase binds GTP, and donation of a hydrogen bond to the β-γ bridging oxygen of GTP is thought to contribute to catalysis by the enzyme (Maegley et al., 1996, Proc. Natl. Acad. Sci. USA 93:8160–8166).

The results presented in this example demonstrate that the hMSH2:hMSH6 heterodimer binds to a mismatched DNA substrate in the presence of ADP, and that the substrate is released from the heterodimer in the presence of ATP or dATP. Because ATP-induced release of the substrate from the heterodimer does not require magnesium and is similarly induced by ATP-γ-S, ATP hydrolysis is not implicated in substrate release. As increasing amounts of ATP or ATP-γ-S were added to the mismatch binding reaction mixture, approximately 15% of S-shifted material gradually became re-associated with the DNA in the form of a NS-shifted heterodimer, as indicated in FIGS. 2A and 2B. This fraction was consistent with the amount of NS binding observed for homoduplex DNA at this concentration of the heterodimer, as indicated in FIG. 2B. These results indicated that hMSH2:hMSH6 heterodimers which dissociated from mismatched substrate could re-associate with either the duplex arms or the ends of the substrate.

Figure 4A:
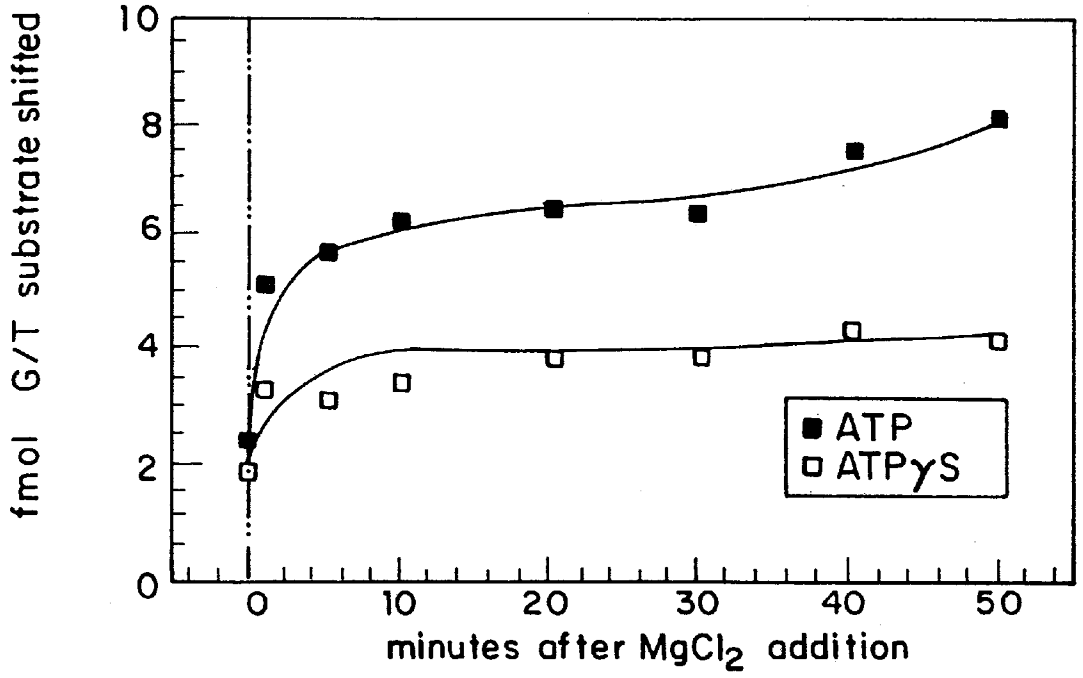
FIGS. 4A and 4B depicts the effects of ATP hydrolysis or ADP binding by the hMSH2/hMSH6 heterodimer on mismatched DNA binding.

ATP Hydrolysis Catalyzed by the hMSH2:hMSH6 Heterodimer Results in Recovery of Mismatch Binding Activity of the Heterodimer To determine the role of ATP hydrolysis in mismatch recognition, ATP or ATP-γ-S was introduced into a mismatch binding reaction mixture in the absence of magnesium. As illustrated in FIGS. 2A, 2B, 2D, and 3, introduction of either compound resulted in release of the hMSH2:hMSH6 heterodimer from the mismatched DNA substrate in the absence of hydrolysis of the compound. In experiments presented in FIG. 4A, magnesium was added to each reaction mixture, which was maintained at 37° C., and the G/T mismatch binding activity of hMSH2:hMSH6 heterodimer was followed over time, with time zero corresponding to the time at which magnesium was added. In the reaction mixture comprising ATP, mismatched DNA substrate binding activity of the heterodimer was initially low, nearly 70% of this activity was recovered after ten minutes of incubation at 37° C., and more than 95% of the activity was recovered fifty minutes after magnesium addition. Substantially less (about 22%) of mismatched DNA substrate binding activity was recovered in the reaction mixture to which ATP-γ-S was added. These results demonstrated that efficient hydrolysis by the heterodimer is essential for recovery of the heterodimer's mismatch binding activity. Substitution of ATP with dATP produced quantitatively similar recovery of mismatch binding activity (i.e. >95% recovery) following incubation at 37° C. Taken together, these results demonstrated that the intrinsic ATPase activity associated with the human hMSH2:hMSH6 heterodimer is required for recovery from mismatch-release induced by binding to and/or exchange with, ATP or dATP.

Figure 4B:
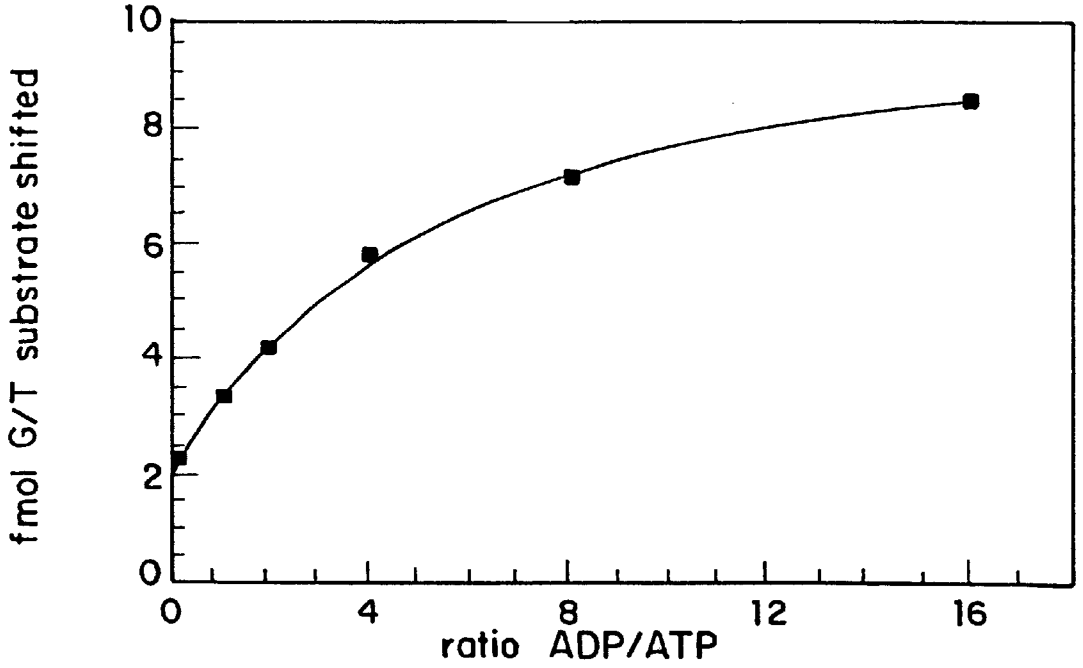

Complete recovery of mismatched DNA substrate binding activity of the hMSH2:hMSH6 heterodimer, which activity was abolished by exposing the heterodimer to ATP, was achieved by increasing the ratio of the concentration of ADP to the ratio of ATP in the solution in which the heterodimer was suspended, as indicated in FIG. 4B In this competition experiment, mismatch binding reaction mixtures comprised 0.2 millimolar ATP, 1 millimolar $MgCl_2$, and a selected concentration of ADP from 0 to 3.2 millimolar. It was determined that a 2- to 3-fold excess of ADP to ATP resulted in reversal of approximately half of the release of substrate by the heterodimer caused by the presence of ATP. Approximately complete reversal of substrate release caused by the presence of ATP was achieved by providing a 16-fold excess of ADP to the mixture. A qualitatively similar, though functionally opposite, result was obtained when the competition was performed by including a fixed concentration of ADP in the reaction mixture and adding various concentrations of ATP. Thus, ADP and ATP are nearly equivalent in their ability to associate with the hMSH2:hMSH6 heterodimer, but the two nucleotides elicited opposite functional effects on mismatch binding. ATP caused release of substrate bound to the heterodimer, and ADP induced binding of the substrate to the heterodimer. Therefore, ADP is responsible for mismatch binding recovery.

Taken together, these observations support the conclusion that the hMSH2:hMSH6 heterodimer functions as a molecular switch, wherein the ATP- (or dATP-) bound heterodimer is "OFF" (i.e. unable to associate with a mismatched DNA substrate with which it is not already associated) and the ADP-bound heterodimer is "ON" (i.e. able to associate with a mismatched DNA substrate with which it is not already associated). A model of the role of the hMSH2:hMSH6 heterodimer is illustrated in FIG. 7.

ATP Hydrolysis and ADP-ATP Exchange Determine Mismatch Binding Functions of the hMSH2:hMSH6 Heterodimer Steady-state analysis of an enzyme having ATPase activity reflects the rate-limiting step of the reaction, which can be either γ-phosphate hydrolysis or adenine nucleotide exchange. To understand the mechanism of the ATPase activity exhibited by the hMSH2:hMSH6 heterodimer and to further define the rate-limiting steps, both hydrolysis and nucleotide exchange steps were directly examined.

Initial rate (i.e. single-turnover) analysis of an enzyme which exhibits ATPase activity involves direct examination of the rate of γ-phosphate hydrolysis, and was performed using a method which is similar to that used for the examination of regulators of G-protein signaling (R G S; Dohlman et al., 1997, J. Biol. Chem. 272:3871–3874). In these experiments, 0.2 micromolar $[^{32}P]$γ-ATP was contacted with hMSH2:hMSH6 heterodimer in the absence of magnesium, yielding a heterodimer having a $[^{32}P]$γ-ATP molecule bound thereto. At a selected time, magnesium and an excess of non-labeled ATP were added to the reaction mixture, and the rate of a single-round of γ-phosphate hydrolysis was assessed. Subsequent rounds of hydrolysis were undetectable because the ATP hydrolyzed during those rounds was not labeled. Because the calculated $K_{cat}$ for ATP at 37° C. was in excess of 20 $minute^{-1}$, and because this rate was above the limit of detection of this methodology, these initial rate experiments were performed at 20° C. It was determined that the hMSH2:hMSH6 heterodimer rapidly hydrolyzed ATP in either the presence or the absence of DNA. These results indicated that γ-phosphate hydrolysis was not the rate limiting step in the steady-state ATP hydrolysis by the heterodimer.

Figure 5A:
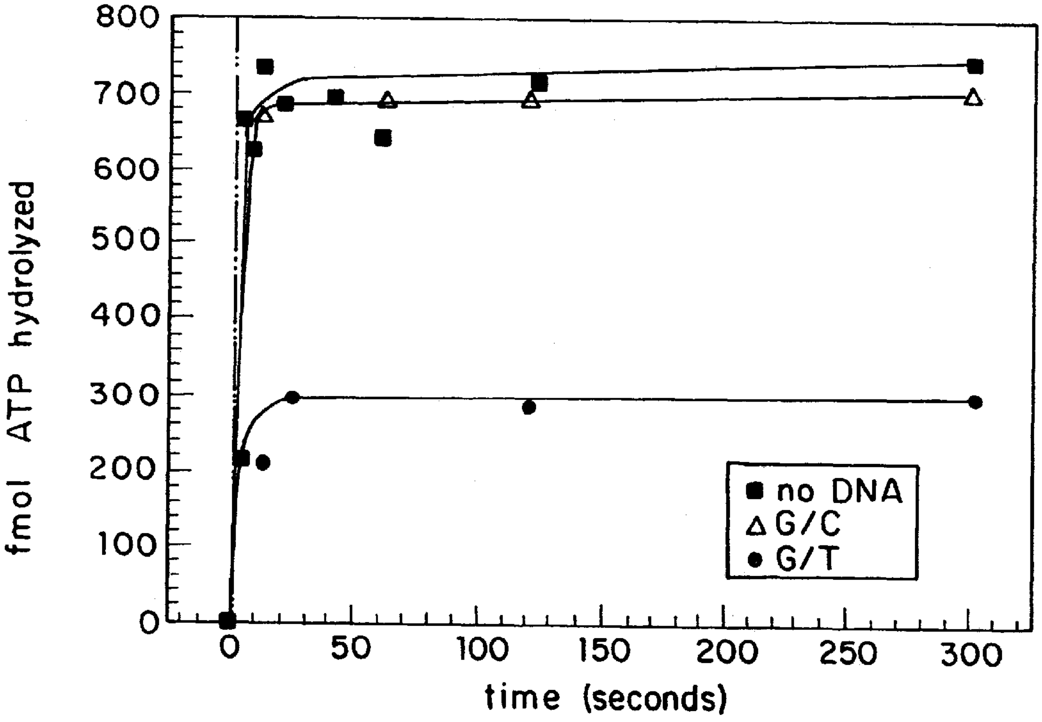
FIG. 5A is a graph which depicts the results obtained in the assays described herein for detecting the rate of a single round of ATP hydrolysis by the complex.
Figure 5B:
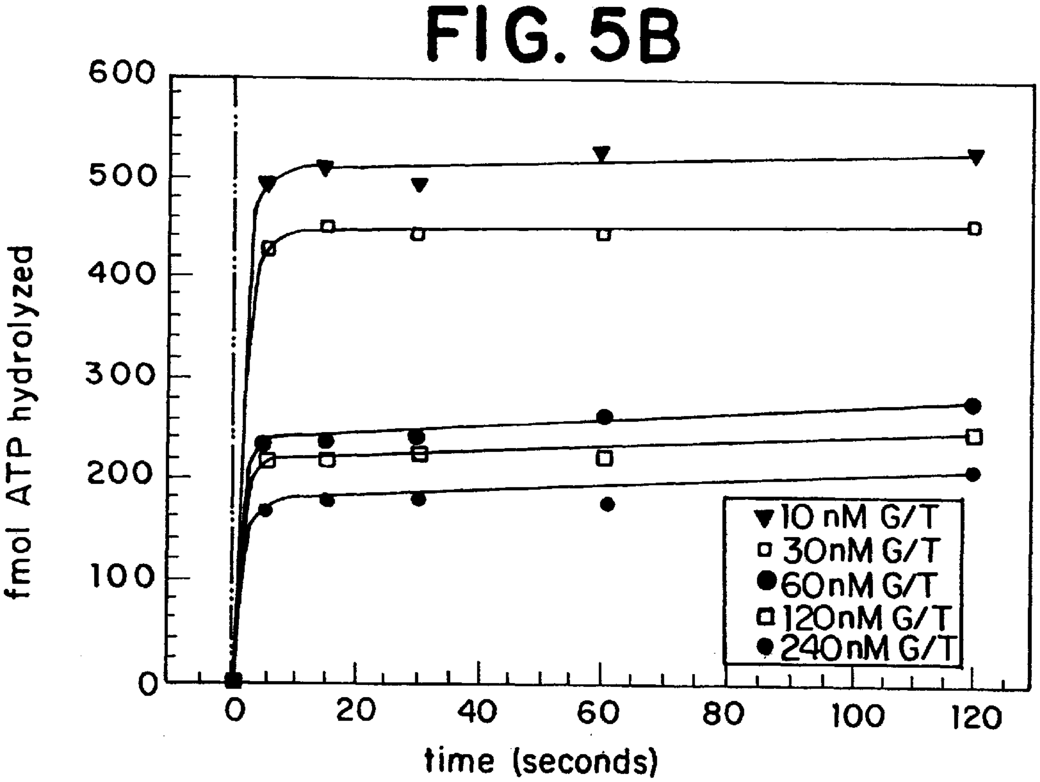
FIG. 5B is a graph which depicts the results obtained in assays described herein for detecting the rate of a single round of ATP hydrolysis by the complex in the presence of selected amounts of mismatched DNA.

The extent of ATP hydrolysis which could be detected was equivalent to the total number of hMSH2:hMSH6 heterodimers which could be bound to $^{32}P$-labeled ATP prior to the addition of magnesium. The maximal extent of detectable ATP hydrolysis was determined to depend on the amount of the G/T-mismatched DNA substrate present in the reaction mixture during binding of labeled ATP to the heterodimer, as indicated in FIGS. 5A and 5B. When the concentration of the G/T-mismatched DNA substrate in to the reaction mixture exceeded the apparent $K_d$ for G/T-mismatched DNA substrate (i.e. about 20 nanomolar), the maximal extent of ATP hydrolysis decreased, as indicated in FIG. 5B. This observation indicated that binding of the hMSH2:hMSH6 heterodimer to a mismatched DNA molecule prior to binding of ATP to the heterodimer inhibits binding of ATP to the mismatched DNA-bound heterodimer. This observation is consistent with the pseudo-uncompetitive behavior deduced in the steady-state ATPase activity experiments described herein (Dixon et al., 1979, Enzymes, 3rd Ed., Academic Press, New York).

Adenine nucleotide exchange was assessed using a method similar to that used for guanine nucleotide exchange experiments involving G proteins. In these studies, [$^3$H]-ADP was contacted with hMSH2:hMSH6 heterodimer in the presence of magnesium, yielding [$^3$H]-ADP-bound heterodimer. At a selected time, an excess of non-labeled ATP was added to the reaction mixture, and the amount of ADP that remained bound to the heterodimer was assessed at selected times.

In the absence of DNA, incomplete ADP nucleotide exchange was observed during a 15 minute reaction period. The half-life of the ADP-bound heterodimer was greater than eight hundred seconds. These results clearly suggest that in the absence of DNA, replacement of ADP by ATP is the rate limiting step for the hMSH2:hMSH6 heterodimer ATPase activity.

In the presence of G/T-mismatched DNA substrate, nucleotide exchange was significantly more rapid, the half-life of the ADP-bound heterodimer being less than two seconds. Thus, it was demonstrated that binding of the heterodimer to a G/T-mismatched DNA substrate stimulated replacement of the labeled ADP molecule originally bound to the heterodimer by a non-labeled ATP molecule.

Taken together with the results obtained from the single turnover hydrolysis experiments described herein, these observations indicated that in the absence of mismatched DNA, the hMSH2:hMSH6 heterodimer is capable of a single ATP hydrolysis reaction that yields an ADP-bound heterodimer. While in the ADP-bound form, the heterodimer does not exchange ADP for ATP until the heterodimer binds to a DNA mismatch. By binding to a mismatch, the ADP-bound heterodimer becomes competent to exchange ADP for ATP. Exchange of ADP for ATP causes release of the heterodimer from the mismatch. ATP-bound heterodimer, when no longer bound to mismatched DNA, is capable of catalyzing ATP hydrolysis, yielding ADP-bound heterodimer, which is competent to bind to a DNA mismatch. These results indicate that the hMSH2:hMSH6 heterodimer is a molecular switch controlled by the phosphorylation state of the adenine nucleotide bound thereto.

Release of the hMSH2:hMSH6 Heterodimer from a G/T-mismatched DNA Substrate May Occur by Dissociation Prior art models of mismatch recognition by MutS homologs implicated ATP-dependent translocation and/or treadmilling along DNA as a mechanism for association and dissociation of the homolog with a DNA mismatch (Modrich, 1989, J. Biol. Chem. 264:6597–6600; Modrich, 1991, Annu. Rev. Genet. 25:229–253; Modrich et al., 1996, Annu. Rev. Biochem. 65:101–133; Allen et al., 1997, EMBO J. 16:4467–4476). Common to all of these prior art models is a postulated time-dependent unidimensional homolog displacement mechanism which occurs whether the homolog is bound to duplex DNA or mismatched DNA. In contrast, a simple dissociation mechanism would exhibit rapid and two-dimensional displacement of the homolog from duplex DNA or mismatched DNA.

The ability to distinguish NS and S electrophoretic bands corresponding to the homologous 81-base pair DNA substrate-bound hMSH2:hMSH6 heterodimer and the G/T-mismatched 81-base pair DNA substrate-bound heterodimer, as illustrated in FIG. 2A, provided an opportunity to examine the dissociation mechanism of the heterodimer from the G/T-mismatched DNA substrate, as well as from homoduplex DNA. In these experiments, the G/T-mismatched DNA substrate was bound to the heterodimer, and an excess of an unlabeled competitor DNA or an excess of ATP, or both, was added to the mixture. If a tracking or sliding mechanism of the prior art were operable for heterodimer dissociation, it would be expected that a time-dependent loss of the S shifted electrophoretic band of G/T-mismatched DNA substrate-bound complex would be observed, and that a coincident gain of the NS electrophoretic band would be observed. If a simple dissociation mechanism were operable for heterodimer dissociation, it would be expected that loss of the S shifted band would be observed without any coincident increase in the intensity of the NS shifted band because the vast excess of unlabeled homoduplex DNA would preclude secondary reassociation of the complex with the arms or ends of the labeled G/T-mismatched DNA substrate. One potential complication would be if the amount of time required for heterodimer enables diffusion of the dimer to a different position on the DNA substrate were nearly the same as the time which would be required for simple dissociation.

Three experiments were performed to determine the mechanism of hMSH2/hMSH6 protein complex dissociation from a labeled 81-base pair G/T-mismatched DNA substrate. The results of these experiments are illustrated in FIG. 6.

Figure 6A:
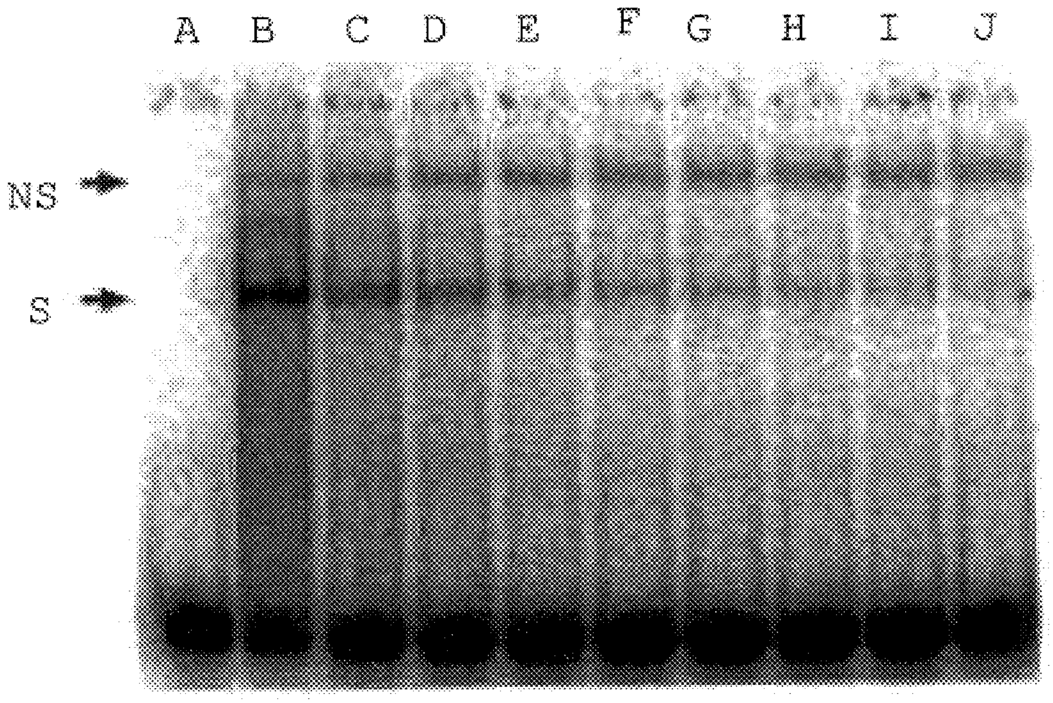
FIGS. 6A, 6B, 6C, and 6D, depicts the results of experiments performed to assess the effects of ATP, homologous DNA, or both, on the dissociation of the hMSH2:hMSH6 heterodimer from DNA.
Figure 6B:
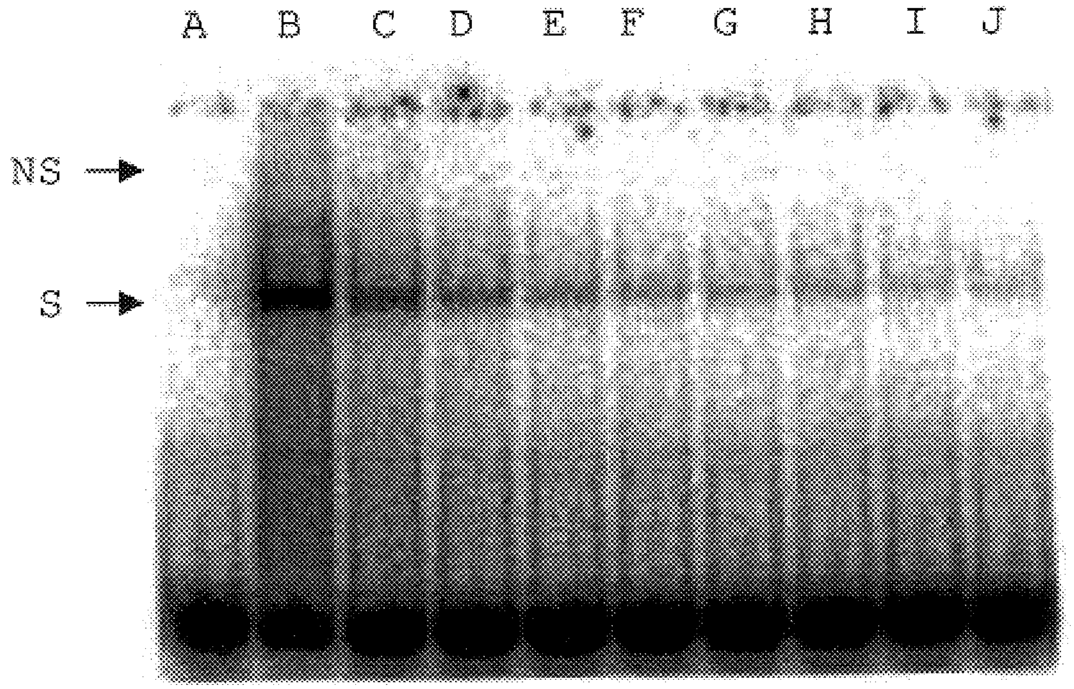
Figure 6C:
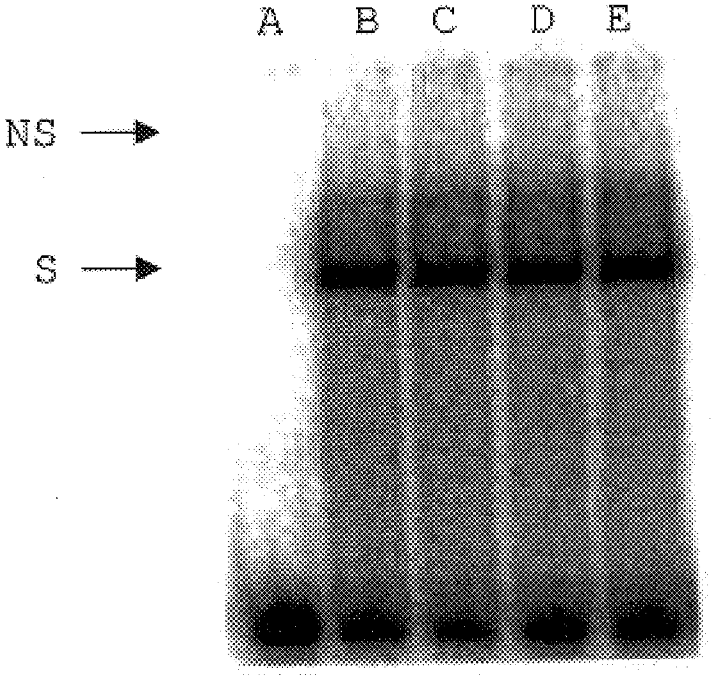

In the first experiment, the stability of G/T-mismatched DNA substrate-bound hMSH2/hMSH6 complex was assessed by exposing the mismatched substrate-bound complex to a 400-fold excess of non-labeled homoduplex DNA and observing the intensities of S shifted and NS shifted electrophoretic bands at selected times, as illustrated in FIG. 6C. Examination of the gel depicted in FIG. 6C indicated that the S-shifted electrophoretic band, and thus the amount of the G/T-mismatched DNA substrate-bound hMSH2:hMSH6 heterodimer in the reaction mixture, was not reduced significantly over the ten minute incubation period. Thus, the half-life of the G/T-mismatched DNA substrate-bound hMSH2:hMSH6 heterodimer was much greater than ten minutes, meaning that the mismatched substrate-bound complex is stable in the presence of a vast excess of homoduplex DNA.

In the second experiment, the stability of G/T-mismatched DNA substrate-bound hMSH2:hMSH6 heterodimer was assessed by exposing the mismatched substrate-bound heterodimer to ATP and observing the intensities of S shifted and NS shifted electrophoretic bands at selected times, as illustrated in FIG. 6A. A gradual decrease in the intensity of the S shifted electrophoretic band was observed, the band having a half life of about twenty seconds. Concurrently with the decrease in the intensity of the S shifted electrophoretic band, a gradual but not quantitative increase in the intensity of the NS-shifted electrophoretic band was observed. This observation indicated that ATP induced a time-dependent reduction of specific binding of the hMSH2:hMSH6 heterodimer to the mismatched DNA substrate and that at least a portion of the heterodimer reassociated with the mismatched DNA substrate in a non-specific manner. However, this experiment did not distinguish between the tracking/sliding or simple dissociation and reassociation mechanisms.

In order to attempt to distinguish between translocation and simple dissociation and reassociation, a third experiment was performed. In this experiment, the stability of G/T-mismatched DNA substrate-bound hMSH2:hMSH6 heterodimer was assessed by exposing the mismatched substrate-bound heterodimer to both ATP and a 400-fold excess of non-labeled homoduplex DNA and observing the intensities of S shifted and NS shifted electrophoretic bands at selected times (FIG. 6B). As in the second experiment, a gradual decrease in the intensity of the S shifted electrophoretic band was observed, the half-life of the band again being about twenty seconds. This observation was consistent with ATP induction of dissociation of the heterodimer from the mismatched DNA substrate. However, under these conditions, no increase in the intensity of the NS electrophoretic band was observed. Together, these observations suggest that in the presence of excess non-labeled homoduplex DNA, the dissociation of the heterodimer from mismatched DNA might not proceed through the product corresponding to the NS electrophoretic band, but instead may be instantaneous and irreversible.

Figure 6D:
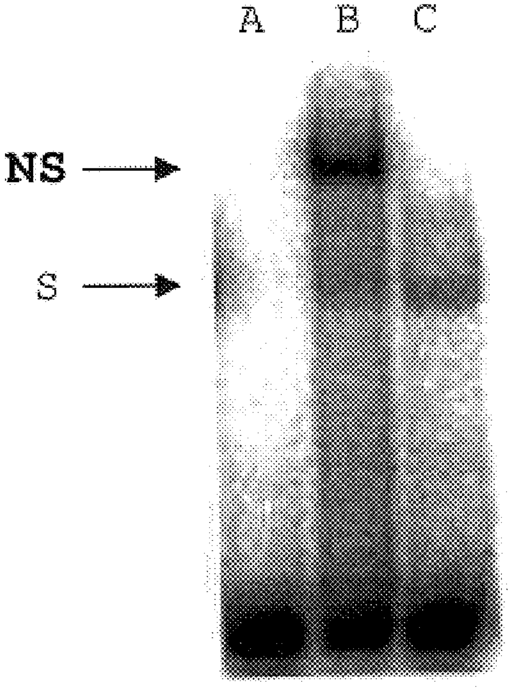

When excess non-labeled homoduplex DNA was added to the homologous 81-base pair DNA substrate, the NS electrophoretic band associated with the product formed by contacting the heterodimer with DNA substrate, as indicated in FIG. 1B, for example, could be detected, as indicated in FIG. 6D. This observation indicated that, even at 4° C., the product corresponding to the NS band was exceedingly unstable and that the level of hMSH2:hMSH6 heterodimer which remained associated with the DNA substrate was less than the lower limit of accurate quantitation using gel shift analysis.

The hMSH2:hMSH6 Heterodimer Acts as a Molecular Switch in Mismatch Recognition

The discovery that the hMSH2:hMSH6 heterodimer is a novel molecular switch which is activatable by ADP was made by reconciling numerous observations described herein. These observations are summarized as follows. ADP and ATP have opposing effects on the role of the hMSH2:hMSH6 heterodimer in mismatched DNA binding. Dissociation of mismatched DNA from the hMSH2:hMSH6 heterodimer is not dependent upon ATP hydrolysis. Hydrolysis of ATP by the hMSH2:hMSH6 heterodimer results in recovery of the ability of the heterodimer to associate with mismatched duplex DNA. γ-Phosphate hydrolysis is not the rate limiting step of ATPase activity catalyzed by the of the heterodimer. Displacement of ADP by ATP is the rate limiting step of ATPase activity catalyzed by the hMSH2:hMSH6 heterodimer. Displacement of ADP from the of the heterodimer by ATP is accelerated in the presence of mismatched duplex DNA, but hydrolysis of the γ-phosphate bond is not accelerated. ATP-dependent release of mismatched DNA from the hMSH2:hMSH6 heterodimer occurs rapidly, possibly by simple dissociation or by rapid ATP-hydrolysis-independent diffusion to a free end of the DNA. These observations indicate that γ-phosphate hydrolysis and displacement of ADP by ATP determine whether the hMSH2:hMSH6 heterodimer binds to or is released from mismatched duplex DNA, as illustrated in FIG. 7. Recognition of the hMSH2:hMSH6 heterodimer as a molecular switch supports the conclusion that it is a trigger for determining the timing of subsequent excision repair-related events.

Implications for Mismatch Repair

The number of hMSH2:hMSH6 heterodimers in the nucleus of a proliferating cell has been estimated to exceed one thousand (Drummond et al., 1995, Science 268:1909–1912; Wilson et al., 1995, Cancer Res. 55:5146–5150; Meyers et al., 1997, Cancer Res. 57:206–208). The calculated $K_d$ of the heterodimer for mismatched DNA (i.e. about 20 nanomolar) implies that a single mismatched nucleotide in a human cell is likely to be efficiently recognized and bound with high affinity by an hMSH2:hMSH6 heterodimer. In the presence of ATP, this high affinity binding is nearly irreversible. Thus, dissociating the heterodimer from mismatched DNA in order to allow a subsequent excision repair event to proceed may be more difficult than binding the heterodimer to the mismatch.

Generality of MutS Function

The studies described in this Example, which involved the human mismatch binding reaction catalyzed by the hMSH2:hMSH6 heterodimer, are consistent with genetic studies performed in both bacteria and yeast. In those studies, mutation of the adenine nucleotide binding and hydrolysis domain(s) resulted in a dominant mutator phenotype (Haber et al., 1991, EMBO. J. 10:2707–2715; Wu et al., 1994, J. Bacteriol. 176:5393–5400; Alani et al., 1997, Mol. Cell. Biol. 17:2436–2447). Those studies, combined with the studies described in this Example, indicate that there may be two opposing functional alterations of MutS homologs that can cause such a dominant mutator phenotype. First, alteration of the ability of the homolog to bind and/or exchange ADP for ATP can cause a dominant mutator phenotype. Second, alteration of the ability of the homolog to hydrolyze ATP can similarly cause such a phenotype. Inability of the homolog to bind to ADP or to exchange ADP for ATP would result in a permanently mismatched DNA-bound form of the MutS homolog. This form of the homolog would exclude the repair machinery from the mismatch site. Inability of the MutS homolog to hydrolyze ATP would result in a form of the homolog that would be unable to bind to mismatched DNA and which, therefore, would be unable to recruit the cellular mismatch repair proteins and factors to the site of the mismatch. Each these conditions would cause an increased mutation rate in the organism containing the homolog, as a consequence of the organism's depressed ability to repair mismatched DNA (Wu et al., 1994, J. Bacteriol. 176:5393–5400).

Preliminary studies performed using the methods described herein and using purified *Escherichia coli* MutS protein suggest that *E. coli* MutS also functions as a molecular switch, albeit with a more stringent requirement for mismatch-induced nucleotide exchange. Therefore, the properties of the MutS homologs hMSH2 and hMSH6, as described herein appear to be properties of all MutS homologs, including, but not limited to, *E. coli* MutS, and the human MutS homologs hMSH2, hMSH3, and hMSH6.

Similarity of the hMSH2:hMSH6 Heterodimer to G-protein Switches

The hMSH2:hMSH6 molecular switch is, in some respects, similar to G-protein switches which have been described (Bokoch et al., 1993, FASEB J. 7:750–759). G-proteins are known to trigger translocation events associated with protein synthesis (Laalami et al., 1996, Biochimie 78:577–589; Parmeggiani et al., 1981, Mol. Cell. Biochem. 35:129–158), cascade events associated with cell signaling (Medema et al., 1993, Crit. Rev. Oncol. 4:615–661; Wiesmuller et al., 1994, Cell Signal. 6:247–267) and physiological responses to ligand-binding by membrane receptors (Spiegel, 1987, Mol. Cell. Endocrinol. 49:1–16). Many G-proteins are associated with regulators that stimulate both the GTPase activity of the G-protein (Tocque et al., 1997, Cell Signal. 9:153–158) and the exchange of G-protein-bound GDP for GTP (Dohlman et al., 1997, J. Biol. Chem. 272:3871–3874; Quilliam et al., 1995, Bioessays 17:395–404). In fact, the Ras G-protein was determined to be unable to catalyze GTP hydrolysis because it is unable to exchange GDP for GTP. The discovery of a GTPase activating protein (GAP) that stimulated GTP γ-phosphate hydrolysis, and a guanine nucleotide exchange factor (GNEF) that stimulated the exchange of GDP for GTP, provided a model for regulation of the Ras G-protein switch (Tocque et al., 1997, Cell Signal. 9:153–158; Dohlman et al., 1997, J. Biol. Chem. 2 72:3871–3874).

It has therefore been discovered that protein regulation of the excision-resynthesis processes associated with mismatch repair occurs by stimulation of the ATPase activity of the hMSH2:hMSH6 heterodimer or of the ability of the heterodimer to exchange ADP for ATP. The latter stimulation can occur either by stabilizing the ADP-bound form of the heterodimer or by stimulating exchange of ADP for ATP to effect release of the heterodimer from mismatched DNA. It is thought by the inventors that MutL homologs, such as the human MutL homologs, hMLH1, hPMS1, and hPMS2, perform these regulatory functions.

EXAMPLE 2

A Mouse Construct Nullizygous for both msh2 and p53 and Methods of Making and Use Thereof Transgenic mice which are nullizygous for both Msh2 and p53 have been made, and are referred to herein as $Msh2^{-/-}$ $p53^{-/-}$ mice. Other transgenic animals which are nullizygous for both Msh2 and p53, and which particularly include mammals, especially including rodents such as mice and rats, may be made using methods analogous to those described herein and are useful in the screening methods described herein.

The development of female $Msh2^{-/-}p53^{-/-}$ mouse embryos is phenotypically arrested at approximately the 9.5 day stage, and apoptosis is induced shortly thereafter in the cells of these embryos. Male $Msh2^{-/-}p53^{-/-}$ mouse embryos are viable, but succumb to tumors significantly earlier than either $Msh2^{-/-}p53^{+/\pm}$ or $Msh2^{+/\pm}p53^{-/-}$ littermates (i.e. nullizygous Msh2 mice or nullizygous p53 mice, respectively). Furthermore, the frequency of microsatellite instability (MSI) in tumor tissue obtained from $Msh2^{-/-}$ $p53^{-/-}$ mice is not significantly different than the frequency in tumor tissue obtained from $Msh2^{-/-}p53^{-/-}$ mice. Synergism in tumorigenesis and independent segregation of the MSI phenotype suggest that Msh2 and p53 are not genetically epistatic.

$Msh2^{-/-}p53^{-/-}$ mice are useful as models of disease or disorder states which cannot be identified in mice nullizygous for only one of Msh2 or p53. Furthermore, $Msh2^{-/-}$ $p53^{-/-}$ mice are useful for identifying compositions which affect the onset or progression of such a disease or disorder state. Thus, a $Msh2^{-/-}p53^{-/-}$ mouse is particularly useful as a model system for studying multistep tumorigenesis, apoptosis, and aging.

The materials and methods used in the experiments presented in this Example are now described.

Generation of $Msh2^{-/-}p53^{-/-}$ Mice

Methods for making heterozygous and nullizygous Msh2 mice and heterozygous and nullizygous p53 mice have been described (de Wind et al., 1995, Cell 82:321–330; Reitmair et al., 1995, Nature Genet. 11:64–70; Donehower et al., 1992, Nature 356:215–221; Jacks et al., 1994, Curr. Biol. 4:1–7; Purdie et al., 1994, Oncogene 9:603–609).

Mice heterozygous for Msh2 (i.e. $Msh2^{+/-}p53^{+/+}$ mice) on a mixed C57BL/6J and 129/Ola background and mice heterozygous for p53 (i.e. $Msh2^{+/+}p53^{+/-}$ mice) on a mixed C57BL/6J and 129/Sv were mated to produce F1 progeny heterozygous for both genes (i.e. $Msh2^{+/-}p53^{+/-}$ mice). Heterozygous sibling F1 progeny were intercrossed to produce progeny nullizygous for both Msh2 and p53 (i.e. $Msh2^{-/-}p53^{-/-}$ mice). Mice were genotyped using Msh2- and p53- specific PCR-based assays, using methods well known in the art.

Isolation of Genomic DNA

Mouse genomic DNA was extracted from ear-notched tissue of mice and from amniotic tissue of mouse embryos at 9.5, 11.5, or 13.5 days of development, using a QIAamp Tissue Kit (Qiagen, Chatsworth, Calif.) according to the manufacturer's instructions.

PCR-based Genotyping of Mice

A three-primer assay specific for Msh2 was carried out as described (Reitmair et al., 1995, Nature Genet. 11:64–70). A four-primer assay specific for p53 was carried out using 50 ng of template DNA in a 50 microliter reaction mixture containing 1 unit of Taq polymerase (Fisher Scientific, Malvern, Pa.) and 100 millimolar each of the following primers, each of which is identified with a five digit number and the sequence of each of which is listed:

10681 (5'-GTGTTTCATT AGTTCCCCAC CTTGAC-3'; SEQ ID NO: 7);

10480 (5'-ATGGGAGGCT GCCAGTCCTA ACCC-3'; SEQ ID NO: 8);

10588 (5'-GTGGGAGGGA CAAAAGTTCG AGGCC-3'; SEQ ID NO: 9); and 10930 (5'-TTTACGGAGC CCTGGCGCTC GATGT-3'; SEQ ID NO: 10). The amplification reaction involved 35 cycles of amplification (94° C., 15 seconds; 56° C., 30 seconds; 72° C., 1 minute) using a Perkin-Elmer GeneAmp 9600 thermal cycler. The wild-type primers, 10681 and 10480, amplified a product of about 320 base pairs length, and the targeted allele (i.e. $p53^-$) primers, 10588 and 10930, amplified a product of about 150 base pairs length.

The gender of embryos was determined using primers specific for the Y-chromosome gene as described (Sah et al., 1995, Nature Genet. 10:175–180). The presence of the X-chromosome was confirmed separately in all cases using the following two X-chromosome specific primers to amplify the locus DXMIT6:

5'-ACCATTCAAATTGGCAAGG-3' (SEQ ID NO: 11); and

5'-GTGGCTCGAGTTGTTTGCAG-3' (SEQ ID NO: 12). PCR cycling conditions were as described above for p53 genotyping, except that the annealing temperature was 53° C., rather than 56° C. The X-chromosome specific primers amplified a product of about 210 base pairs in length. All PCR amplification products were resolved by electrophoresis on a 2% (w/v) agarose gel alongside a 100 base pair polynucleotide ladder standard and were visualized by ethidium bromide staining.

Timed Pregnancies

Male and female mice having a known $Msh2^{+/-}p53^{+/-}$, $Msh2^{+/-}p53^{-/-}$, or $Msh2^{-/-}p53^{+/-}$ genotype were mated and each of the females was examined daily for the presence of a vaginal plug (an indicator of pregnancy which appears at about day 0.5 of embryo development). Pregnant females were sacrificed at 13.5 days, at 11.5 days, or at 9.5 days gestation. Embryos were dissected out from the pregnant females into Hank's Balanced Salt Solution (Gibco BRL, Grand Island, N.Y.) under a dissecting microscope, fixed in 4% (v/v) buffered formalin, and documented by photomicrography. Amnion was retrieved from each embryo, DNA was extracted therefrom, and the sex and genotype of each embryo was determined by PCR.

Histology

Tissue specimens were fixed in 10% (v/v) or 4% (v/v) buffered formalin and embedded in paraffin. Histological analysis was carried out on 3 micrometer-thick sections stained with hematoxylin and eosin (H&E).

TUNEL Assay

Paraffin-embedded tissue sections were de-waxed and rehydrated using a graded alcohol series, using methods well known in the art. Apoptotic cells and appropriate positive and negative control samples were analyzed using the In Situ Cell Detection Kit, AP with NBT/BCIP, manufactured by Boehringer Mamiheim (Indianapolis, Ind.), according to the manufacturer's instructions. TUNEL-stained tissue sections were analyzed both by fluorescence microscopy and light microscopy.

Kaplan-Meier Survival

Kaplan-Meier survival probability was calculated for mice that were found dead or were sacrificed when found to be moribund. The age of the mice was calculated in days. Because no mice died in the control group, confidence limits could not be determined.

Microsatellite Instability in Lymphoid Tumors

Paired ear-notch (i.e. normal) and lymphoid tumor tissues were analyzed for microsatellite instability at five chromosomal loci: D17Mit123, D10Mit2, D6Mit59, D4Mit27, and D3Mit203. Microsatellite primer sequence pairs appropriate for amplification of these loci were obtained from the World Wide Web site of the Whitehead Institute for Genome Research (http://www.genome.wi.mit.edu), and were chosen to amplify fragments containing at least twenty dinucleotide repeat sequences. PCR amplifications were carried out in a total reaction volume of 25 $\mu$l, using 50 ng of DNA as template, 100 millimolar of each primer pair and 1 unit of Taq polymerase (Fisher Scientific, Malvern, Pa.). The amplification reaction involved 35 cycles of amplification (94° C., 15 seconds; 56° C., 30 seconds; 72° C., 1 minute). Amplified products were resolved by electrophoresis on a 6.7% (w/v) denaturing polyacrylamide gel and were visualized by silver nitrate staining of the gel.

The results of the experiments presented in this Example are now described.

Twenty-one $Msh2^{-/-}p53^{-/-}$ mice were generated from $Msh2^{+/-}p53^{+/-}$, $Msh2^{-/-}p53^{+/-}$, or $Msh2^{+/-}p53^{-/-}$ parents. When the gender of each of the twenty $Msh2^{-/-}p53^{-/-}$ mice was examined, all were determined to be male $Msh2^{-/-}p53^{-/-}$ mice. The absence of female $Msh2^{-/-}p53^{-/-}$ offspring is highly significant (p<0.001) and is unlikely to reflect the intrinsic bias for males observed in the colony from which the mice were derived, wherein the normal male:female ratio is 181:138.

The fertility of male $Msh2^{-/-}p53^{-/-}$ mice could not be determined, because they succumbed to tumors before they successfully mated. However, pathological examination of the testes of the male $Msh2^{-/-}p53^{-/-}$ mice did not reveal gross abnormalities upon autopsy, and histology revealed mature spermatogenesis in all twenty-one of the male $Msh2^{-/-}p53^{-/-}$ mice. Taken together, these results suggest that $Msh2^{-/-}p53^{-/-}$ male mice are not sterile.

No gross morphological abnormalities were observed in $Msh2^{-/-}$ animals either in utero or post-natally (de Wind et al., 1995, Cell 82:321–330; Reitmair et al., 1995, Nature Genet. 11:64–70). In addition, the number of male and female $Msh2^{-/-}$ mice in the studies described herein was in accord with the expected 1:1 ratio, which suggests that male and female nullizygous Msh2 mice are equally viable. However, a decrease in the number of live born nullizygous p53 mice from the expected Mendelian ratio was observed, which is qualitatively similar to previous reports, although our limited numbers did not indicate a sex bias (Sah et al., 1995, Nature Genet. 10:175–180; Nicols et al., 1995, Nature Genet. 10:181–187).

No female $Msh2^{-/-}p53^{-/-}$ mice were observed at weaning and none of thirteen one-day-old pups which were found dead in the litters of mating pairs were $Msh2^{-/-}p53^{-/-}$. Thus, all female embryos nullizygous for both Msh2 and p53 died in utero. To determine the point in embryonic development at which these embryos died, numerous timed pregnancies were established. Because $Msh2^{-/-}p53^{-/-}$ males were not available and $Msh2^{-/-}p53^{-/-}$ females were not viable, pairs of mice, each of which mice was a known $Msh2^{+/-}p53^{+/-}$, $Msh2^{+/-}p53^{-/-}$, or $Msh2^{-/-}p53^{+/-}$ mouse, were mated to produce $Msh2^{-/-}p53^{-/-}$ embryos. Pregnant females were sacrificed at 9.5, 11.5, and 13.5 days of gestation, the embryos were pathologically assessed for developmental defects and the genotype and gender of each embryo were determined by PCR. The results of these analyses are presented in Table 1. A total of twenty-one embryos and six resorption sites were recovered from three females at day 13.5 of gestation. Of the twenty-one 13.5 day embryos, two male $Msh2^{-/-}p53^{-/-}$ embryos and no female $Msh2^{-/-}p53^{-/-}$ embryos were recovered, although a total of five $Msh2^{-/-}p53^{-/-}$ embryos were statistically expected. Two 13.5 day embryos (one male $Msh2^{+/-}p53^{-/-}$; one female $Msh2^{-/-}p53^{+/-}$) displayed exencephaly, while all other 13.5 day embryos appeared normal (Sah et al., 1995, Nature Genet. 10:175–180).

TABLE 1

Sex and Morphological Phenotype of Timed Post-Implantation Embryos

| Days Develop-ment | Resorp-tion Sites | # of Em-bryos | Embryos Typed | Female $Msh2^{-/-}p53^{-/-}$ Nor | Female $Msh2^{-/-}p53^{-/-}$ Abnr | Male $Msh2^{-/-}p53^{-/-}$ Nor | Male $Msh2^{-/-}p53^{-/-}$ Abnr |
|---|---|---|---|---|---|---|---|
| e9.5 | 3 | 30 | 28 | 3 | 1 | 2 | 1 |
| e11.5 | 11 | 21 | 17 | 0 | 4 | 2 | 0 |
| e13.5 | 6 | 21 | 21 | 0 | 0 | 2 | 0 |
| *28 | — | *96 | *96 | *0 | *0 | *21 | *0 |

*Refers to live-born animals at twenty-eight days following birth.

In Table 1, embryos that arrested in development, that were in resorption, or that displayed gross abnormalities were classified as abnormal (Abnr), while those embryos which were not arrested in development, were not in resorption, and did not display gross abnormalities were classified as normal (Nor). Thirteen newborn pups that were found dead, none of which were $Msh2^{-/-}p53^{-/-}$, are not represented in this Table.

Figure 9A:
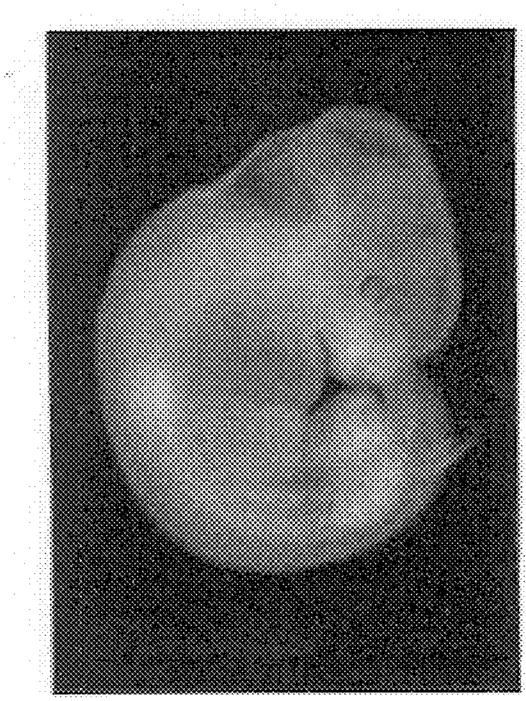
FIGS. 9A, 9B, 9C, and 9D, is a series of images, each of which depicts a whole mount view of an $Msh2^{-/-}p53^{-/-}$ embryo at day 11.5 of development. The embryo depicted in FIG. 9A is a male $Msh2^{-/-}p53^{-/-}$ mouse embryo, and exhibits phenotypically normal embryonic development, relative to mice having the same genotypic background. The embryos depicted in FIGS. 9B, 9C, and 9D are female $Msh2^{-/-}p53^{-/-}$ mouse embryos that are littermates of the male mouse depicted in FIG. 9A. The female mouse embryos depicted in FIGS. 9B, 9C, and 9D exhibit developmental arrest having a phenotype corresponding to that expected at day 9.5 of embryonic development.
Figure 9C:
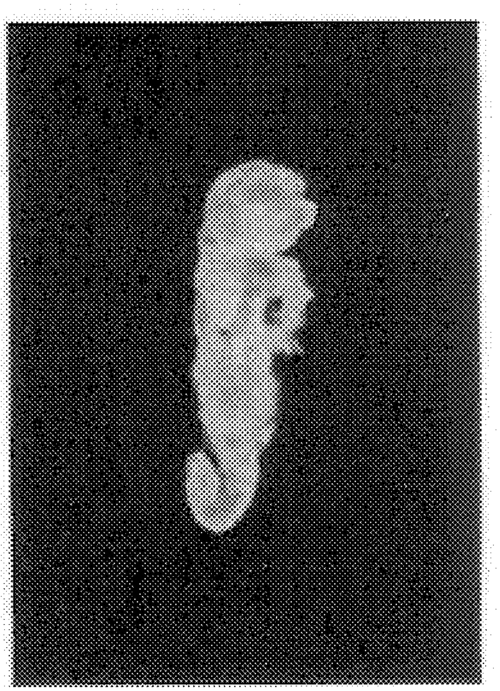
Figure 9D:
Figure 9B:
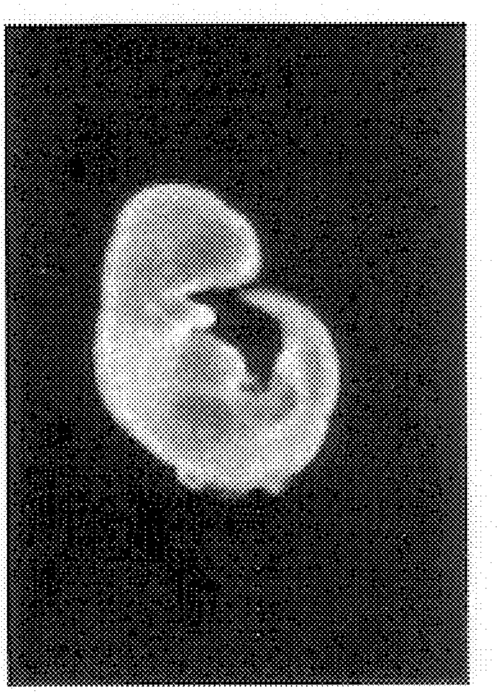
Figure 10A:
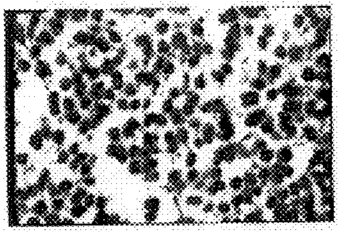
FIG. 10, comprising Panels A, B, C, D, E, and F, is a series of images, each of which depicts a paraffin embedded section obtained from an 11.5 day old female mouse embryo. The images in Panels A, C, and E each depict a section obtained from an 11.5 day old normal embryo. The images in Panels B, D, and F each depict a section obtained from an 11.5 day old $Msh2^{-/-}p53^{-/-}$ mouse embryo. The sections depicted in Panels A and B are at 100× magnification and are stained with hematoxylin and eosin. Magnification of the normal embryo is of the somite region of a sagittal section. The sections depicted in Panels C and D are at 100× magnification and are chromogenically-TUNEL stained. The sections depicted Panels E and F are at 40× magnification and are fluorescently-TUNEL stained. Cells undergoing apoptosis in normal female embryos were rare; chromogenically- and fluorescently-TUNEL stained cells depicted in Panels C and E represent circumscribed apoptotic foci normally found in developing mouse embryos.
Figure 10B:
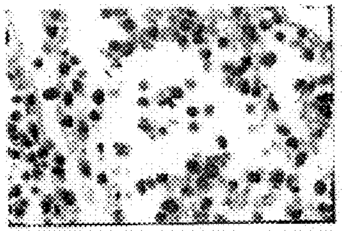
Figure 10C:
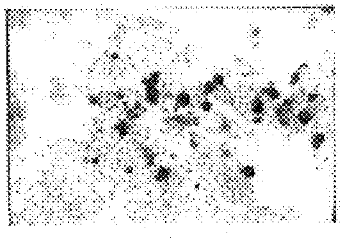
Figure 10D:
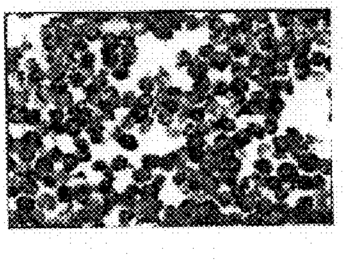
Figure 10E:
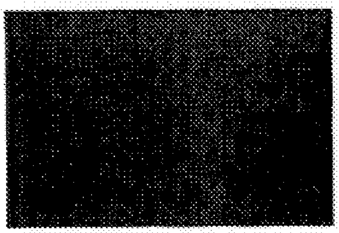
Figure 10F:
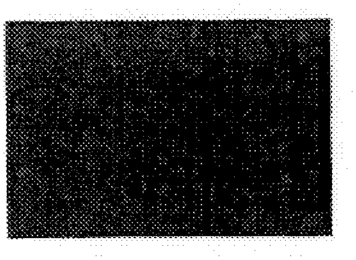

Twenty-one embryos and eleven resorption sites were recovered from three pregnant females at day 11.5 of gestation. Of these, complete PCR typing results were determined for seventeen embryos and one resorption site. Five embryos were determined to be $Msh2^{-/-}p53^{-/-}$, although eight $Msh2^{-/-}p53^{-/-}$ embryos were statistically expected. Two of the five embryos were males that appeared morphologically normal (one is depicted in FIG. 9A), and three of the five embryos were females, all three of which had undergone developmental arrest, and all three of which are depicted in FIGS. 9B, 9C, and 9D. The three female $Msh2^{-/-}p53^{-/-}$ embryos appeared opaque and somites were not visible. Based on the gross morphology of the three female $Msh2^{-/-}p53^{-/-}$ embryos, it was estimated that they died at 9.5 days of development. The tissue from the resorption site was typed as female $Msh2^{-/-}p53^{-/-}$.

Thirty embryos and three resorption sites were recovered from pregnant females at day 9.5 of gestation. Twenty-eight embryos and one resorption site were successfully typed. Two embryos and a resorption site were found to be male $Msh2^{-/-}p53^{-/-}$, and four embryos were typed as female $Msh2^{-/-}p53^{-/-}$. Six $Msh2^{-/-}p53^{-/-}$ embryos were statistically expected. Neither of the male $Msh2^{-/-}p53^{-/-}$ embryos exhibited any gross morphological abnormality. It is likely that the male $Msh2^{-/-}p53^{-/-}$ resorption site represents a spontaneous abortion event. In one of the four female $Msh2^{-/-}p53^{-/-}$ embryos, the anterior neural tube was not closed and the heart was not seen to beat, which should occur around day 9 of development. These observations are consistent with a developmental delay that could result from late fertilization or implantation or alternatively, from a developmental abnormality that is apparent at day 9.5.

Paraffin embedded tissue sections from wildtype and $Msh2^{-/-}p53^{-/-}$ female embryos, as depicted in FIG. 10, from $Msh2^{-/-}$ embryos, and from $p53^{-/-}$ embryos were examined at day 11.5 and at day 13.5. While the wildtype, $Msh2^{-/-}$, and $p53^{-/-}$ embryos had clearly distinguished developmental features at day 11.5, the arrested $Msh2^{-/-}p53^{-/-}$ female embryos contained noncohesive cells without preservation of embryonal tissue structures. In addition, H&E stained $Msh2^{-/-}p53^{-/-}$ female embryonic tissue sections appeared to contain an large number of "blebbed" structures typical of apoptotic cells. Furthermore, loss of nuclear hematoxylin stain typical for necrosis was not observed in H&E stained $Msh2^{-/-}p53^{-/-}$ female embryonic tissue sections (FIG. 10, Panel B).

TUNEL staining was performed on the paraffin embedded tissue sections (FIG. 10, Panels C–F). Although wildtype (FIG. 10, Panels C and E), $Msh2^{-/-}$, and $p_{53}^{-/-}$ embryos displayed circumscribed foci of apoptotic cells characteristic of normal embryonal development, $Msh2^{-/-}p53^{-/-}$ female embryos displayed global catastrophic apoptosis (FIG. 10, Panels D and F). Furthermore, fluorescence TUNEL staining of $Msh2^{-/-}p53^{-/-}$ female embryos revealed a speckled intracellular patterning characteristic of fragmented chromatin (FIG. 10, Panel F). It was estimated that between about 60% and about 90% of cells in $Msh2^{-/-}p53^{-/-}$ female embryos were undergoing visible apoptosis, as assessed by H&E and TUNEL staining.

Figure 11:
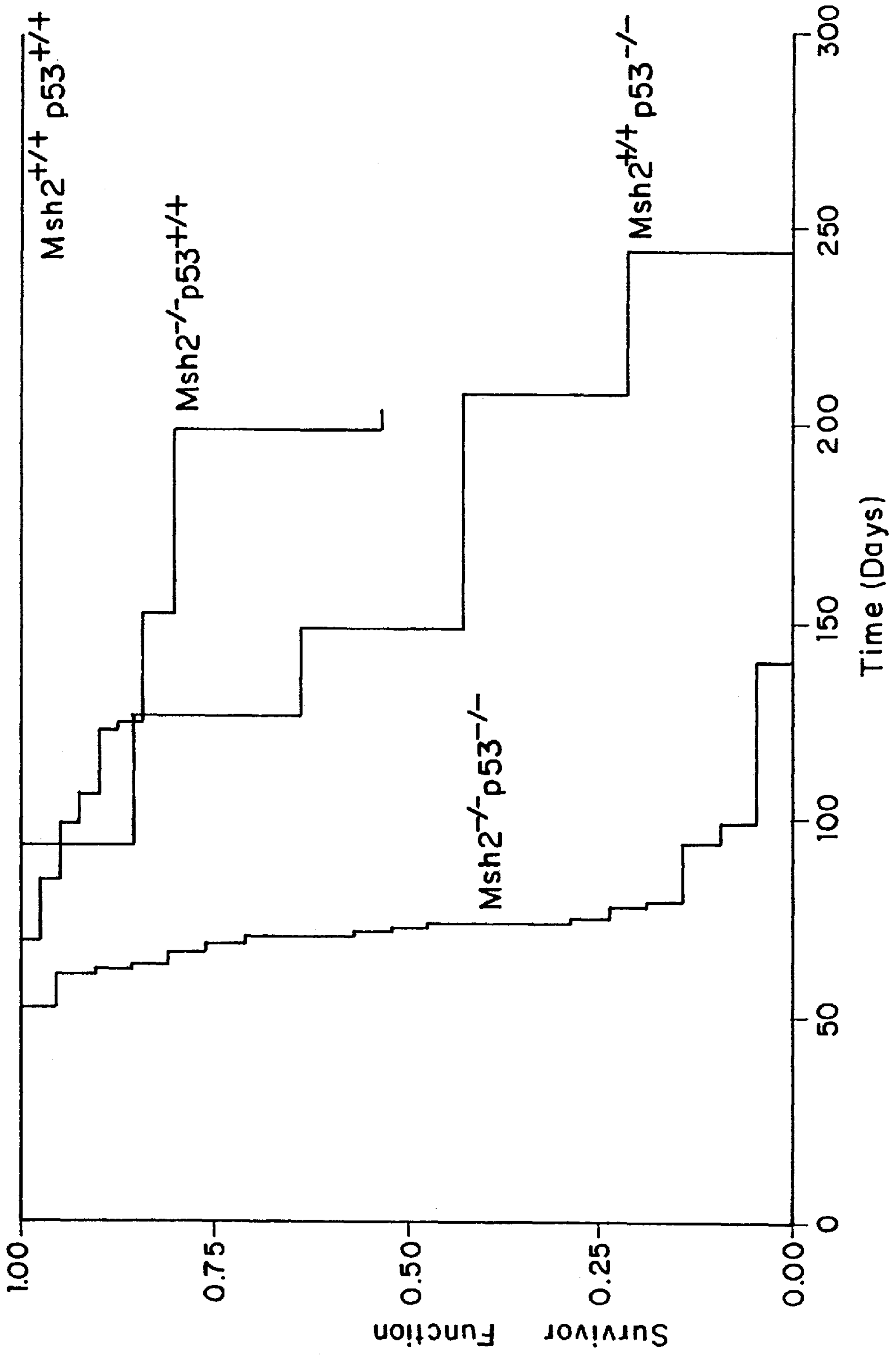
FIG. 11 is a graph which depicts Kaplan-Meier survival probabilities of $Msh2^{-/-}$, $p53^{-/-}$, and $Msh2^{-/-}p53^{-/-}$ mice.

Kaplan-Meier survival analysis was performed on a cohort of ninety-six mice, the data for which analysis are graphically presented in FIG. 11. $Msh2^{-/-}p53^{-/-}$ mice began to die of generalized lymphomas at day 53 after birth and all twenty-one $Msh2^{-/-}p53^{-/-}$ mice were dead within four months of birth. In contrast, only 18% (eight of forty-four) of $Msh2^{-/-}$ littermates and 71% (five of seven) of $p53^{-/-}$ littermates were dead at the time the mice were analyzed. Thus, $Msh2^{-/-}p53^{-/-}$ mice had a significantly ($p<0.001$) reduced median survival time of 73 days compared with the median survival time of either $Msh2^{-/-}$ mice (i.e. 200 days) or $p53^{-/-}$ mice (i.e. 149 days). Furthermore, all twenty-four wild-type (i.e. $Msh2^{+/\pm}p53^{+/\pm}$) littermates were alive after approximately ten months. These results indicate that Msh2 and p53 null mutations cooperatively promote tumorigenesis. p53 has also been shown to cooperate with a variety of other genes in mouse tumorigenesis models (Blyth et al., 1995, Oncogene 10:1717–1723; Williams et al., 1994, Cold Spring Harbor Symp. Quant. Biol. 59:449–457; Williams et al., 1994, Cell 79:329–339; Donehower et al., 1995, Genes Dev. 9:882–895; Nacht et al., 1996, Genes Dev. 10:2055–2066). However, as is apparent from FIG. 11, the effect on tumor-related death of having dual null mutations of Msh2 and p53 is greater than the sum of the effects of having a single null mutation in Msh2 or p53 alone. Thus, the $Msh2^{-/-}p53^{-/-}$ mouse described herein has a phenotype which is significantly different from a mere combination of the phenotype of a $Msh2^{-/-}$ mouse and the phenotype of a $p53^{-/-}$ mouse.

Pathological examination of tumors showed that all twenty-one $Msh2^{-/-}p53^{-/-}$ mice developed highly aggressive generalized lymphomas involving major organs. In addition, a pleomorphic sarcoma in the flank, a malignant fibrous histiocytoma of the neck, and a tubular adenoma of the small intestine were observed, while other epithelial neoplasms were not detected. The tumor spectrum of $Msh2^{-/-}$ and $p_{53}^{-/-}$ mice appeared similar to previous observations (de Wind et al., 1995, Cell 82:321–330; Reitmair et al., 1995, Nature Genet. 11:64–70; Donehower et al., 1992, Nature 356:215–221; Jacks et al., 1994, Curr. Biol. 4:1–7; Purdie et al., 1994, Oncogene 9:603–609). The tumor spectrum of $Msh2^{-/-}p53^{-/-}$ mice differs significantly from the tumor spectrum of either $Msh2^{-/-}$ mice or $p53^{-/-}$ mice. Thus, $Msh2^{-/-}p53^{-/-}$ mice have utility different from that of either $Msh2^{-/-}$ mice or $p53^{-/-}$ mice.

Normal and tumor tissues obtained from individual $Msh2^{-/-}p53^{-/-}$ mice were examined for microsatellite instability at five loci: D17Mit123, D10Mit2, D6Mit59, D4Mit27, and D3Mit203. The results of these MSI studies are presented in Table 2. The frequency of MSI in tumor tissues obtained from $Msh2^{-/-}$ mice was not significantly different ($p>0.05$) from the frequency of MSI in tumor tissues obtained from $Msh2^{-/-}p53^{-/-}$ mice. Microsatellite instability was not observed in lymphomatous tumor tissue obtained from the seven $p53^{-/-}$ mice examined. The observation that $Msh2^{-/-}p53^{-/-}$ mice developed earlier onset of tumor-related disease, combined with the observed separate segregation of the MSI phenotype with the Msh2 allele, suggests that Msh2 and p53 are not genetically epistatic.

TABLE 2

The Frequency of Microsatellite Instability in $p53^{-/-}$, $Msh2^{-/-}$, and $Msh2^{-/-}p53^{-/-}$ Mice

| Genotype Tumor/Normal Pairs | Tumors Examined (n) | MSI at ≧1 Locus | MSI at ≧2 Loci | MSI at ≧3 Loci |
|---|---|---|---|---|
| $p53^{-/-}$ | 7 | 0 (0%) | 0 (0%) | 0 (0%) |
| $Msh2^{-/-}$ | 8 | 6 (75%) | 4 (50%) | 3 (38%) |
| *$Msh2^{-/-}p53^{-/-}$ | 21 | 17 (81%) | 14 (67%) | 12 (57%) |

*Because female $Msh2^{-/-}p53^{-/-}$ mice died during embryonic development, this refers to only male $Msh2^{-/-}p53^{-/-}$ mice.

It is remarkable that female $Msh2^{-/-}p53^{-/-}$ mouse embryos underwent global developmental arrest and that widespread apoptosis of the cells of such embryos occurred around day 9.5 of development. That these embryos underwent implantation and gastrulation strongly suggests that they are capable of executing the earlier stages of embryogenesis. The arrested phenotype is reminiscent of that described for a small proportion of female $p53^{-/-}$ mice (Sah et al., 1995, Nature Genet. 10:175–180). However, unlike $p53^{-/-}$ mice, no normal female $Msh2^{-/-}p53^{-/-}$ mice or embryos were observed beyond 9.5 days of embryonic development. This observation supports the conclusion that the female embryonic lethality of $Msh2^{-/-}p53^{-/-}$ mice is highly penetrant. In addition, none of the female $Msh2^{-/-}p53^{-/-}$ embryos displayed the exencephaly that characterized the $p53^{-/-}$ mice (Sah et al., 1995, Nature Genet. 10:175–180). Furthermore, while there was no difference in apoptosis observed in developing $p53^{-/-}$ mouse embryos, global catastrophic apoptosis was clearly observed in all the $Msh2^{-/-}p53^{-/-}$ female mouse embryos examined at day 9.5 of development. These results suggest that female $Msh2^{-/-}p53^{-/-}$ mice succumb at an earlier stage and by an entirely different pathology than $p53^{-/-}$ mice.

Without being bound to any particular theory, the lethality observed in female $Msh2^{-/-}p53^{-/-}$ mouse embryos is consistent with the following explanation. In the female embryonic lineage, dosage compensation is achieved by random X chromosome inactivation around the time of gastrulation, at which time intense embryonic cellular proliferation and apoptosis promote embryonic differentiation (Lyon, 1961, Nature 190:372–373; Rastan, 1994, Curr. Opin. Genet. Dev. 4:292–297; Theiler, 1972, In: *The House Mouse Development and Normal Stages from Fertilization to* 4 *Weeks of Age*, Springer-Verlag, New York, p. 168). The global apoptotic effect need not occur coincidentally with X chromosome inactivation. The full effect of dysregulation may only become apparent after a number of cell divisions when the embryo undergoes a further burst of proliferation during embryonic 'turning' between 8 and 9.5 days.

It has been shown that the inactivated X chromosome replicates late in S phase (Taylor, 1960, J. Biophys. Biochem. Cytol. 7:455–464; Tagaki, 1974, Exp. Cell. Res. 86:127–135). In addition, cells deficient inp53 have been shown to be defective for damage-induced $G_1$/S checkpoint arrest, and cells that are deficient in MMR have been shown to be deficient for damage-induced $G_2$/M checkpoint arrest (Baker et al., 1990, Science 249:912–915; Diller et al., 1990, Mol. Cell. Biol. 10:5772–5781; Lin et al., 1992, Proc. Natl. Acad. Sci. USA 89:9210–9214; Hawn et al., 1995, Cancer Res. 55:3721–3725; Marra et al., 1996, Oncogene 13:2189–2196). Thus, female-specific $Msh2^{-/-}p53^{-/-}$ embryo lethality may result from dysregulation of damage-induced arrest checkpoint control, wherein such dysregulation is caused by a deficiency of both p53 and Msh2, and whereby such dysregulation results in an inability of $Msh2^{-/-}p53^{-/-}$ cells to arrest cell division and repair damage introduced into the late replicating inactive X chromosome. Such damage could take the form of non-replicated regions or chromosomal fragments that have resulted from inappropriate cell division prior to the completion of inactive X chromosome replication. Fragmented, reactivated, or otherwise altered inactive X chromosomes may then lead to global catastrophic cellular failure, developmental arrest, and apoptosis. Furthermore, the observation that the highest levels of p53 mRNA are detected in wild-type embryos between 9 and 11 days of development suggests an important role for p53 protein within this time frame (Rogel et al., 1985, Mol. Cell. Biol. 5:2851–2855).

EXAMPLE 3

A Discussion of hMSH2:hMSH6 Heterodimers in the Context of Mismatch Repair, Molecular Switches, and Signal Transduction The foundation of molecular switches in biology is grounded in translation elongation and cellular signal transduction. In these systems, guanine nucleotide-bound proteins (G-proteins) produce the ON and OFF signaling states that act as gates for downstream biochemical processes. Experimental results described herein, in view of the results of studies by others, suggest that a similar molecular switch relies on adenine nucleotide-bound forms (A-proteins) to produce an ON and OFF signaling state related to mismatched DNA repair and possibly to other processes. In the field of signal transduction, the concept of a molecular switch is elementary, while the biochemical processes of DNA repair appear foreign. Similarly, the field of DNA repair recognizes the complex machinery required for DNA manipulation events, but regards biochemical signaling processes as essential cellular input which is outside the genome juggernaut.

Genetics of Mismatch Repair

There are at least three ways in which mismatched nucleotides arise in DNA. Physical or chemical damage to the DNA and its precursors, such as de-amination of 5-methyl-cytosine, can give rise to mismatched bases (Friedberg, 1990, DNA Repair W.H. Freeman Co., New York). Misincorporation of nucleotides during DNA replication can yield mismatched base pairs as well as the insertion and deletion of nucleotides (for review see: Kolodner, 1996, Genes Dev. 10:1433–1442; Modrich, 1989, J. Biol. Chem. 264:6597–6600; Modrich, 1997, J. Biol. Chem. 272:24727–24730). Genetic recombination produces regions of heteroduplex DNA which may contain mismatched nucleotides when such heteroduplexes result from the pairing of two different parental DNA sequences (Holliday, 1964, Genet. Res. 5:282–304). Mismatched nucleotides produced by each of these mechanisms are known to be repaired by enzyme systems that are both specific and overlapping (Friedberg, 1990, DNA Repair, W.H. Freeman Co., New York).

The most extensively studied system for mismatch repair (MMR) is the DNA adenine methylation (Dam)-instructed pathway of *Escherichia coli* (Modrich, 1989, J. Biol. Chem. 264:6597–6600; Modrich and Lahue, 1996, Annu. Rev. Biochem. 65:101–133). The Dam-Instructed pathway promotes a long-patch (approximately 2 kilobase pair) excision repair reaction which is genetically dependent on the mutH, mutL, mutS, and mutU (uvrD) gene products. Discrimination of the newly replicated DNA strand from the original template DNA strand is dependent on transient under-methylation of the adenine nucleotide within GATC Dam sequences. The MutHLS pathway appears to be the most active MMR pathway in *E. coli* and is known to both increase the fidelity of DNA replication as well as to act on recombination intermediates containing mis-paired bases (Fishel et al., 1983, UCLA Symp. Mol. Cell. Biol. New Series 11:309–324; Fishel et al., 1986, J. Mol. Biol. 188:147–157).

Homologs of prokaryotic MutS and MutL proteins have been identified in nearly every organism with the exception of Archaea (Fishel et al., 1997, Curr. Opin. Genet. Dev. 7:105–113; Kolodner, 1996, Genes Dev. 10:1433–1442). At present, there are 41 MutS homologs and 21 MutL homologs in the NCBI database. In *S. cerevisiae*, six MutS homologs (MSH1–MSH6) and three MutL homologs (MLH1, MLH2, PMS1) have been identified. In human cells, a nearly identical set of five MutS homologs (hMSH2–hMSH6) and three MutL homologs (hMLH1, hPMS1, and hPMS2) are known (Acharya et al., 1996, Proc. Natl. Acad. Sci. USA 93:13629–13634; Bronner et al., 1994, Nature 368:258–261; Burns et al., 1994, Genes Dev. 8:1087–1105; Fishel et al., 1993, Cell 75:1027–1038; Fujii et al., 1989, J. Biol. Chem. 264:10057–10064; Hollingsworth et al., 1995, Genes Dev. 9:1728–1739; Kramer et al., 1989, J. Bacteriol. 171:5339–5346; Linton et al., 1989, Mol. Cell. Biol. 9:3058–3072; Mankovich et al., 1989, J. Bacteriol. 171:5325–5331; New et al., 1993, Mol. Gen. Genet. 239:97–108; Nicolaides et al., 1994, Nature 371:75–80; Palombo et al., 1995, Science 268:19121–19914; Prolla et al., 1994, Mol. Cell. Biol. 14:407–415; Reenan et al., 1992, Genetics 132:963–973). Yet, with the exception of gram-negative bacteria, there do not appear to be homologs of MutH. Thus, the mechanism of strand discrimination in even close relatives of *E. coli*, the gram-positive bacteria, remains a mystery. The multiple MutS and MutL homologs have been found to participate in the diverse activities of nuclear (MSH2, MSH3, MSH6, MLH1, PMS1) and organellar (MSH1) post-replication mismatch repair as well as having distinct meiotic functions (MSH4, MSH5) (Fishel et al., 1997, Curr. Opin. Genet. Dev. 7:105–113; Kolodner, 1996, Genes Dev. 10:1433–1442).

Biochemistry of Mismatch Repair

Purification and reconstitution studies by Modrich and colleagues have led to a biochemical model for post-replication mismatch repair in *E. coli*. The reconstituted system requires the MutH, MutL, MutS and UvrD (helicase II) proteins along with DNA polymerase III holoenzyme, DNA ligase, single-stranded DNA binding protein (SSB) and one of the single-stranded DNA exonucleases, ExoI, ExoVII or RecJ (Cooper et al., 1993, J. Biol. Chem. 268:11823–11829; Grilley et al., 1989, J. Biol. Chem. 264:1000–1004; Lahue et al., 1989, Science 245:160–164; Lu et al., 1983, Proc. Natl. Acad. Sci. USA 80:4639–4643; Su et al., 1986, Proc. Natl. Acad. Sci. USA 83:5057–5061; Welsh et al., 1987, J. Biol. Chem. 262:15624–15629). In this widely held biochemical model, initiation of a MMR event occurs when MutS recognizes and binds mis-paired nucleotides that result from polymerase misincorporation errors (Su et al., 1986, Proc. Natl. Acad. Sci. USA 83:5057–5061). It is suggested that MutS mismatch binding is followed by interaction with the MutL protein (Grilley et al., 1989, J. Biol. Chem. 264:1000–1004), which has been proposed to accelerate an ATP-dependent translocation of the MutS-MutL complex (Allen et al., 1997, EMBO J. 16: 4467–4476) to a hemi-methylated GATC Dam site bound by MutH (Welsh et al., 1987, J. Biol. Chem. 262:15624–15629). The MutS-MutL complex then stimulates an intrinsic endonuclease activity of MutH which results in a specific strand scission on the non-methylated newly replicated DNA strand (Cooper et al., 1993, J. Biol. Chem. 268:11823–11829; Lahue et al., 1989, Science 245:160–164; Welsh et al., 1987, J. Biol. Chem. 262:15624–15629). This strand scission directs one of three single-stranded exonucleases (RecJ, Exo I, ExoVII) to degrade the newly replicated strand, which is then re-synthesized by the PolIII holoenzyme complex (Lahue et al., 1989, Science 245:160–164). The net result is a strand-specific mismatch repair event which can be bidirectional. Many of the genetic studies performed with this system appear to support this biochemical interpretation. For example, mutH, mutL, and mutS bacteria exhibit a mutator phenotype that is presumed to be the result of the increased probability of misincorporation errors leading to mutations (Demerec et al., 1957, Carnegie Inst. Wash. Yearbook 370:390–406; Hill, 1970, Mutat. Res. 9:341–344; Miyake, 1960, Genetics 45:755–762; Siegel et al., 1967, J. Bacteriol. 94:38–47). However, not all predictions arising from this model agree with the genetic results. For example, recJ exoI exo VII bacteria do not appear to exhibit a mutator phenotype (Harris et al., 1998, J. Bacteriol. 180:989–993), suggesting that there may be other exonuclease(s) or mechanism(s) involved in the mismatch repair process.

Functions for the Mismatch Repair Proteins

An activity exhibited by mismatch repair proteins is the specific mis-pair binding activity ascribed to MutS homologues (Acharya et al., 1996, Proc. Natl. Acad. Sci. USA 93:13629–13634; Chi et al., 1994, J. Biol. Chem., 269:29984–29992; Drummond et al., 1995, Science 268:1909–1912; Fishel et al., 1994, Science 266:1403–1405; Gradia et al., 1997, Cell 91:995–1005; Marsischky et al., 1996, Genes Dev. 10:407–420; Su et al., 1986, Proc. Natl. Acad. Sci. USA 83:5057–5061). A clear flnction of the MutL homologs has, until the present invention, not been clear. Classification of MutS and MutL homologs is based on the recognition of highly conserved regions of amino acid identity. The most highly conserved region of the MutS homologs is confined to a region of approximately 150 amino acids that encompass a helix-turn-helix domain associated with a Walker-A adenine-nucleotide and magnesium binding motif. Such motifs were described by Walker et al. (1982, EMBO J. 1:945–951). This adenine nucleotide binding domain constitutes 100% of the identity between the known MutS homologs (Fishel et al., 1997, Curr. Opin. Genet. Dev. 7:105–113). Purified bacterial, yeast, and human MutS homologs exhibit an intrinsic low-level ATP hydrolytic (ATPase) activity (Alani et al., 1997, Mol. Cell. Biol. 17:2436–2447; Chi et al., 1994, J. Biol. Chem., 269:29984–29992; Gradia et al., 1997, Cell 91:995–1005; Haber et al., 1991, EMBO J 10:2707–2715). This ATPase activity is likely to be important for the function of the MutS homologs, as evidenced by the observation that mutation of a conserved lysine residue in the adenine nucleotide binding domain results in a dominant mutator phenotype in both bacteria and yeast (Alani et al., 1997, Mol. Cell. Biol. 17:2436–2447; Haber et al., 1991, EMBO J. 10:2707–2715).

The most widely held model for MMR suggests MutS mis-pair binding is followed by MutL association that results in an energy dependent translocation of this complex to a hemi-methylated Dam site occupied by the MutH protein. In retrospect, this appears to have been a simplistic view since the rate of ATP hydrolysis ($k_{cat} \cong 10\ min^{-1}$) is unlikely to be sufficient to drive mechanical translocation the, on average, several hundred to thousand nucleotides required to encounter a MutH bound hemimethylated site. For example, if one ATP was required to translocate one nucleotide, as the most well accepted mechanism suggests, then it would take 25–100 minutes to encounter a MutH on average. Yet, re-methylation of the transiently hemimethylated Dam sites has been found to occur within 0.1 to 3 minutes of passage of the replication fork (Campbell et al., 1990, Cell 62:967–979). While the ATPase activity could in theory be significantly faster in vivo, no stimulatory factor has been identified to date in spite of an extensive search. In addition, the prevailing mechanism does not adequately account for MutL function nor the highly conserved domains recognized between MutL homologs from bacteria to man (regions containing 100% identity in 21 homologs).

The hMSH2–hMSH6 Molecular Switch

As described herein in Example 2 and elsewhere, human MutS homolog dimers, such as the hMSH2:hMSH6 heterodimer, function as molecular switches responsible for the timing of mismatch repair, as illustrated in FIG. 7. This conclusion is based on the observations that:

1) The ADP-bound heterodimer has high affinity for mismatched nucleotides;
2) exchange of ADP for ATP results in release of the heterodimer from mismatched duplex DNA in the absence of hydrolysis;
3) release of the heterodimer from mismatched duplex DNA occurs by hydrolysis-independent diffusion off the ends of the short oligonucleotides used in the experiments described in Example 2, as confirmed by the experiments described in Example 4 herein; and
4) hydrolysis of ATP results in recovery of the mismatch-binding competent ADP-bound heterodimer.

The rate-limiting step and the ultimate control of the hMSH2:hMSH6 molecular switch is likely to be ADP→ATP exchange, which is exceedingly inefficient in the absence of mismatched duplex DNA. The characteristics of the hMSH2:hMSH6 heterodimer appear analogous to the characteristics of G-protein mediators of seven-transmembrane (7-TM) domain receptor signaling such as that used by the β-Adrenergic and Rhodopsin Receptors and the prototypical oncoprotein/G-protein Ras (Tocque et al., 1997 Cell Signal. 9:153–158). More specifically, the observation that the hMSH2:hMSH6 heterodimer is induced to exchange ADP for ATP in the presence of mismatched duplex DNA and then dissociates from the mismatched portion of the duplex DNA to transduce a signal, is analogous to the observation that ligand binding by 7-TM receptors induces associated G-proteins to exchange GDP→GTP and dissociate from the receptor to transduce a signal.

These similarities suggest two related models for mismatch repair that are fundamentally different from all previously suggested models. These models are each based on the concept that MutS and its homologs are a novel type of molecular switch which determines the timing and/or appropriate assembly of repair components. The apparent affinity of the hMSH2:hMSH6 heterodimer for mismatched duplex DNA (Kd≅2–20 nanomolar) suggests that a single mismatch in a human cell should be efficiently recognized and bound. Furthermore, binding of the hMSH2:hMSH6 heterodimer to mismatched duplex DNA is slightly stabilized in the presence of ADP. We would propose two non-exclusive models.

In the first model, tight binding of the ADP-bound form of the hMSH2:hMSH6 heterodimer to mismatched duplex DNA acts as a flag for the assembly or nearby localization of DNA excision repair components. When the complete excision repair complex is assembled, exchange of ADP for ATP is triggered and the hMSH2:hMSH6 heterodimer is released from the mismatched portion of the duplex DNA, thus signaling exonucleolytic excision and resynthesis of the region containing the mismatched nucleotide. Once released from the mismatched portion of the duplex DNA, the intrinsic ATPase activity of hMSH2-hMSH6 hydrolyzes bound ATP, resulting in a form that is once again competent for mis-pair binding.

In the second model, recognition of mismatched duplex DNA by the ADP-bound form of the hMSH2:hMSH6 heterodimer provokes ADP→ATP nucleotide exchange. ATP-hydrolysis-independent DNA-associated diffusion of the hMSH2:hMSH6 heterodimer away from the mismatch portion of the duplex DNA to the assembled (or partially assembled) DNA mismatch repair complex. Activation of these components by the confederation of the ATP-bound form of the hMSH2:hMSH6 heterodimer either engages the repair process (signaling the timing of mismatch repair as above) or triggers assembly of the remaining DNA mismatch repair components. This activation event results in release of the hMSH2:hMSH6 heterodimer from the duplex DNA, hydrolysis of ATP bound to the hMSH2:hMSH6 heterodimer, and recycling of the form of the hMSH2:hMSH6 heterodimer capable of associating with mismatched duplex DNA. An advantage of this second model is that the hMSH2:hMSH6 heterodimer remains associated with the DNA in an activated-form, poised to transduce the mismatch signal to any nearby mismatch repair components.

As a free protein complex, the hMSH2:hMSH6 heterodimer does not efficiently exchange ADP remaining after hydrolysis of ATP bound thereto, providing a long-term mismatch recognition-competent molecule. A key difference in the mismatch repair models described above and those previously proposed, is the concept that ATP hydrolysis is not required to physically transduce the mismatch binding signal to downstream DNA mismatch repair components. Instead, ATP hydrolysis is required only to recycle the mis-pair recognition component (i.e. the hMSH2:hMSH6 heterodimer). Without wishing to be bound by any particular theory, it is thought that the signal state of the hMSH2:hMSH6 heterodimer is related to the conformational state of the heterodimer, which in turn is related to whether ADP or ATP is bound thereto.

One of the most important observations concerning G-proteins is their regulation by associated proteins (Bokoch et al., 1993, FASEB J. 7:750–759). There are two halves to the GTPase cycle: γ-phosphate hydrolysis and GDP→GTP nucleotide exchange. Both of these steps can be regulated either by inhibition or acceleration of these partial reactions. For example, the Ras protein has an remarkably sluggish intrinsic GTPase activity (Trahey et al., 1987, Mol. Cell. Biol. 7:541–544), which can be accelerated at least 104- to 105-fold by a GTPase Activating Protein (GAP) (Trahey et al., 1987, Science 238:542–545). In addition, there are other Regulators of G-Protein Signaling (RGS) that singularly accelerate GTP γ-phosphate hydrolysis, and GDP→GTP exchange stimulators (GES) and guanine dissociation inhibitors (GDI) that singularly affect nucleotide exchange (Dohlman et al., 1997, J. Biol. Chem. 272:3871–3874; Quilliam et al., 1995, Bioessays 17:395–404; Tocque et al., 1997, Cell Signal 9:153–158). It has been discovered herein that MutL homologs perform analogous functions (i.e. accelerate ATP γ-phosphate hydrolysis, and ADP→ATP exchange) with respect to MutS homologs.

Biological Switches and the Second Law of Thermodynamics

One could argue that the concept of a singular ON or OFF state in a molecular switch might violate the second law of thermodynamics. This law requires that biochemical systems transit one state to the other by a series of microscopically reversible steps. This idea is based in statistical mechanics as it is applied to a system at equilibrium—which must be applied a priori to enzyme catalyzed biological processes. It is easy to visualize the origins of the principle of microscopic reversibility by considering the consequences were it NOT true. For example, if the rate of A→B were greater than B→A at equilibrium, each of the rates B→C, C→D, and D→A would also have to be greater than their reverse rates in order to prevent build-up of the concentration of any species, which is not permitted at equilibrium. In this case there would be a preferred direction-of-operation of the reaction cycle. Such a spontaneous cycle in a system at equilibrium (i.e. an engine that spontaneously produces work) is not consistent with the drive toward maximum entropy contained in the second law of thermodynamics.

There is no violation of the second law of thermodynamics if the transit from an OFF to ON state (or visa versa) occurs reversibly. The molecular basis for this type of microscopic reversibility can be visualized for the MutS dimer and G-protein switches as reversible nucleotide-binding as well as intermediate protein conformational changes that occur while transiting the extreme states. It is these conformational transitions that determine interaction with effectors which is ultimately accounted for by the hydrolysis of NTP. More significantly, one can experimentally affect the equilibrium of each state by altering the ratio of NDP/NTP in the absence of any hydrolysis, as indicated in FIG. 4B. It is also important to note that microscopic reversibility has been directly demonstrated for the "gated" maxi $K^+$ ion pump, which is a molecular switch controlled by similar conformational transitions (Song et al., 1994, Biophys. J. 67:91–104). Thus, molecular switches are both reversible and, at equilibrium, clearly preserving a fundamental tenant of thermodynamics.

Similarities Between Signal Transduction and DNA Metabolism

The use of controlled molecular switches appears to pervade all aspects of biology. From the standpoint of DNA metabolism, switch controlled processes appear mechanistically sensible. It is well known that the cellular components which perform replication, recombination, repair, and chromosome segregation are very large and composed of multiple subunits (Alberts, 1998, Cell 92:291–294). Analogous to an assembly-line for an automobile or an airplane, the assembly of DNA metabolic machines must be done precisely and in a specific order to ensure appropriate function. A series of well defined switches could logically control the progression of such an ordered assembly process.

The same type of switch-controlled cascade events that transduce cellular signals may also control DNA metabolic events. An important difference between these switches is the identity of the nucleotide that induces the conformational transitions associated with signaling. At the moment the general rule seems to be that guanine nucleotides are involved in cellular signaling events and adenine nucleotides are involved in DNA metabolic signaling events.

EXAMPLE 4

Interactions of hMSH2 with hMSH3 and of hMSH2 with hMSH6:

Examination of Mutations Associated with HNPCC

In the experiments described in this Example, mutations in the human mismatch repair protein hMSH2 were determined to co-segregate with the occurrence in individuals afflicted with hereditary non-polyposis colorectal cancer (HNPCC). As described herein, hMSH2 forms specific mis-pair binding complexes with hMSH3 and hMSH6. These protein interactions were further characterized by mapping the contact regions between the monomers of the hMSH2:hMSH3 and hMSH2:hMSH6 heterodimers.

The results described in this Example demonstrate that there are at least two distinct regions of monomer:monomer interaction in both hMSH2:hMSH3 and hMSH2:hMSH6 heterodimers. The same regions of the hMSH2 monomer interact with regions of both the hMSH3 monomer and the hMSH6 monomer. Furthermore, there is a coordinated linear orientation of these regions, by which is meant that the amino-terminal region of hMSH2 associates with the amino-terminal of either hMSH3 or hMSH6 and the carboxy-terminal region of hMSH2 associates with the carboxy-terminal region of either hMSH3 or hMSH6. Several missense alterations of hMSH2 obtained from HNPCC kindreds were examined and were determined to occur within the consensus monomer:monomer interaction regions. None of these missense mutations prevented monomer:monomer interaction. These data support the idea that an altered interaction of hMSH2 with hMSH3 or an altered interaction of hMSH2 with hMSH6 is unlikely to be causative of HNPCC.

In the experiments described in this Example the regions of monomer:monomer interaction were ascertained for hMSH2:hMSH3 and hMSH2:hMSH6 heterodimers. Two distinct interaction regions were identified for hMSH2:hMSH3 heterodimers and for hMSH2:hMSH6 heterodimers. The interaction regions of hMSH2 with either hMSH3 or hMSH6 appeared to be identical. Several missense mutations of hMSH2 were constructed. These mutations have been reported by others to co-segregate with HNPCC. None of these alterations affected the interactions between hMSH2 and either hMSH3 or hMSH6 heterodimers.

The materials and methods used in the experiments presented in this Example are not described.

Reagents and Enzymes

Restriction endonucleases were obtained from New England Biolabs (Beverly, Mass.). PCR reactions were performed using the High Fidelity PCR Kit obtained from Boehringer Mannheim (Mannheim, Germany). Oligonucleotides were synthesized using an Applied Biosystems (Foster City, Calif.) model 3948 nucleic acid synthesis and purification system. DNA plasmid constructs were purified using Qiagen (Hilden, Germany) DNA purification kits. In vitro transcription and translation (IVTT) reactions were performed using the Promega (Madison, Wis.) TNT™ Coupled Rabbit Reticulocyte Lysate System. Radiolabeled $^{35}S$ methionine was used to label proteins and was obtained from Dupont NEN (Wilmington, Del.). Glutathione linked (GST) agarose beads were purchased from Sigma (St. Louis, Mo.).

Subcloning of hMSH2 and hMSH3

The cloning of hMSH2, hMSH3, and hMSH6 cDNAs and subcloning into pET expression vectors (obtained from Novagen) has been previously described (Acharya et al., 1996, Proc. Natl. Acad. Sci. USA 93:13629–13634). In this study, we used a HeLa cDNA clone ofhMSH3 (Gen Bank Accession U61981).

GST fusion proteins were synthesized using the pGEX system (Pharmacia, Sweden). For ease of cloning, plasmid pGEX-4T-2 was modified as follows. The vector DNA was digested using EcoRI and BamHI restriction endonucleases and purified by gel electrophoresis. A double-stranded linker oligonucleotide comprising a polynucleotide having the nucleotide sequence SEQ ID NO: 13 and a polynucleotide having the nucleotide sequence SEQ ID NO: 14 was ligated into the vector. SEQ ID NO: 13 is 5'-GATCCGAGAA CCTGTACTTC CAGGGACATA TGGCCATGGG TACCG-3'. SEQ ID NO: 14 is 5'-AATTCGGTAC CCATG-GCCAT ATGTCCCTGG AAGTACAGGT TCTCG-3'. The vector is herein referred to as pGEX-SG1 and permitted subcloning using NdeI and NcoI restriction endonuclease sites in which the ATG initiation codon within each site was in frame with the GST moiety. Vector pGEX-SG1 also contained a TEV protease site just upstream of the NdeI and NcoI sites.

Construction of hMSH2 Truncation Mutations

The hMSH2 deletion mutants were constructed using known PCR truncation mutagenesis methods. 'Forward' primers were generated by adding a polynucleotide homologous with six codons corresponding to the desired 3'-end of Msh2, starting with a codon having a guanine residue in the 5'-position and adding the 17 nucleotides immediately 3'- with respect to that residue, to the 3'-end of a polynucleotide having the nucleotide sequence 5'-GCGGATCCCA TGG-3' (SEQ ID NO: 15). 'Reverse' primers were generated by adding a polynucleotide homologous with the 18 nucleotides of the complementary strand corresponding to the six codons of desired 5'-end of Msh2 to the 3'-end of a polynucleotide having the nucleotide sequence 5'-GGAGGATCCC TA-3' (SEQ ID NO: 16). Using a forward and reverse primer, a PCR reaction was performed using pET3d-hMSH2 as template DNA. The PCR product and pET24d were digested with NcoI and BamHI, purified by gel electrophoresis, and ligated together.

To make truncated peptides containing an internal deletion, pET 24d-hMSH2 (which did not encode amino acid residues 700–800 of hMSH2) was generated by performing PCR on hMSH2 using a pair of polynucleotide primers having sequences 5'-GCGGATCCCA TGGCA-GAAGT GTCCATTGTG-3' (SEQ ID NO: 17) and 5'-GGAGGATCCC ATATGTAGAT TATTAACAGT TGG-3' (SEQ ID NO: 18). The amplification product and pET24d were digested using NcoI and BamHI, and the digested products were purified by gel electrophoresis and ligated together. The resulting vector permitted ligation of fragments using NdeI and BamHI. 'Forward' primers were designed using the first 18 nucleotides of the desired 3'-end of msh2 ligated to the 3'-end of a polynucleotide having the sequence 5'-GGCGGTATCC ATATG-3' (SEQ ID NO: 19). The reverse primer was the same as the one described earlier in this Example. PCR fragments were ligated into this vector using NdeI and BamHI. Site directed mutagenesis of hMSH2 was performed using overlap PCR, as described (Kallal et al., 1997, Mol. Cell. Biol. 17:2897–2907). All of the site directed mutations were completely sequenced using a Perkin Elmer ABI Sequencer with XL upgrade (Perkin Elmer Cetus, Norwalk, Conn.).

Construction of hMSH3 and hMSH6 Truncation Mutations hMSH3 and hMSH6 truncation constructs were created using a method analogous to that used to generate to the hMSH2 deletion mutants. 'Forward' primers were generated using the same method described for designing hMSH2 'forward' primers for hMSH2 mutations having truncations. The reverse primers were generated using the same method described for designing hMSH2 'reverse' primers for hMSH2 mutations having either truncations or internal deletions, except that the polynucleotide had the sequence 5'-GGCATACTCG AGCTA-3' (SEQ ID NO: 20), instead of SEQ ID NO: 16. The PCR amplification product was subcloned into either pET24d or pGEX-SG1.

pET24d-hMSH3 (which did not encode amino acid residues 800–990 of hMSH3) was constructed by performing PCR using msh3 and a pair of polynucleotide primers having sequences 5'-GCGGATCCCA TGGATTTTCT AGAGAAATTC-3' (SEQ ID NO: 21) and 5'-GGACGCGTCG TCGACCTAAC CGGTATCTCT GATGAAATAC TC-3' (SEQ ID NO: 22). The amplified product and pET24d were digested using restriction endonucleases NcoI and SalI and subcloned. This vector permitted ligation of inserts using restriction endonucleases AgeI and XhoI. Forward primers were generated by ligating six codons corresponding to the desired 3'-end of msh3 to a polynucleotide having the sequence 5'-GCGGTGACCG GT-3' (SEQ ID NO: 23). Reverse primers were generated as described earlier, only homologous with the non-coding strand of msh3. PCR was performed, and the amplified products were ligated.

In order to avoid errors introduced by random PCR mutagenesis, all PCR amplification products were either completely sequenced or the experiments were conducted using two separately isolated PCR products.

GST Fusion Protein Interaction Assay

An overnight culture of *E. coli* XL-blue cells which harbored pGEX-hMSH(X) (i.e. 'X' being 2, 3, or 6) was grown in LB with 50 milligrams per milliliter ampicillin. 50 milliliter of Luria broth containing ampicillin was inoculated with 1 milliliter of the overnight culture, and the culture was incubated until the optical density, as assessed at 600 nanometers, was about 0.5. IPTG was added to a final concentration of 0.1 millimolar, and the culture container placed in a shaker at 30° C. for 2 hours to generate induced cells. Induced cells were pelleted and resuspended in 800 milliliters of phosphate buffered saline (Boehringer Mannheim, Germany) containing protease inhibitors (0.5 millimolar PMSF, 0.8 milligrams per milliliter leupeptin, 0.8 milligrams per milliliter pepstatin, and 0.1 millimolar EDTA). Lysozyme was added to a concentration of 1 milligram per milliliter, and the mixture was incubated on ice for 30 minutes. Triton X-100 and dithiothreitol were added to final concentrations of 0.2% (v/v) and 2 millimolar, respectively. The lysate was frozen and thawed twice to completely lyse the cells. DNase (Boehringer Mannheim, Germany) was added to a final concentration of 20 micrograms per milliliter, and the lysate was incubated on ice for an additional 20 minutes. Cell debris was removed by centrifuging the lysate at 14,000 rpm in a refrigerated Eppendorf (Model 5402) centrifuge for 30 min. The supernatant was transferred to a new microfuge tube which contained rehydrated GST-agarose beads in a proportion whereby approximately 10–50 nanograms of protein were present for every 25 microliters of beads that were present. GST-fusion protein levels were quantified as described herein. The lysate was incubated with the GST-agarose beads at 4° C. on a rocking platform. After rocking for 1–2 hours, the incubation mixture was centrifuged at 1000 rpm in an Eppendorf microfuge for 30 seconds, the supernatant removed, and the beads were gently resuspended in 500 milliliters of Binding Buffer. Binding Buffer consisted of 20 millimolar Tris, pH 7.5, 10% (v/v) glycerol, 150 millimolar NaCl, 5 millimolar EDTA, 1 millimolar DTT, 0.1% (v/v) Tween 20, 0.75 milligrams per milliliter BSA, 0.5 millimolar PMSF, 0.8 milligrams per milliliter leupeptin, and 0.8 milligrams per milliliter pepstatin. The centrifugation and re-suspension was repeated three times to wash the beads substantially free of non-specific lysate proteins. Suspended beads were added to a 14 milliliter sterile polypropylene tube, diluted with Binding Buffer to approximately 50 microliters of packed glutathione beads per milliliter and incubated at 4° C. on a rocking platform for 30 minutes in order to allow BSA to coat the beads. 500 milliliters of these coated GST-fusion protein associated glutathione beads, which comprised about 10–50 nanograms of bound GST-fusion protein, was then aliquoted into 1.5 milliliter microfuge tubes. GST-fusion protein expression levels were quantitated by Coomassie Brilliant Blue staining of protein separated by SDS-PAGE gels, using BSA as a standard.

In vitro transcription and translation (IVTT) reactions involving $^{35}$S-Methionine were performed with pET-hMSH (Y) (i.e. where 'Y' was 2, 3, or 6) using purified DNA according to the manufacturers recommendations. IVTT reactions were pre-run to determine the relative molar concentration of each construct. This value was calculated using the specific activity of $^{35}$S-Methionine, correcting for the number of methionine residues in each IVTT construct and using SDS-PAGE and a Molecular Dynamics PhosphorImager device equipped with ImageQuant software (Sunnyvale, Calif.). Up to 10 microliters of the IVTT protein was added to each tube such that each sample contained an approximately equimolar concentration of IVTT protein. An IVTT reaction which used pET24d as the vector was added to normalize the total amount of IVTT mixture in each tube. The tubes were incubated for at least one hour at 4° C. on a rocker. The beads were washed three times with the Binding Buffer and resuspended in 50 microliters of SDS loading buffer, which consisted of 0.25 Tris, pH 6.8, 5% (w/v) sucrose, 2% (w/v) SDS, 5% (v/v) 2-mercaptoethanol, and 0.005% (w/v) bromophenol blue. Samples were resolved by SDS-PAGE, and imaged using the Molecular Dynamics PhosphorImager (Sunnyvale, Calif.).

It is recognized that the GST-IVTT interaction assay system is not quantitative, and may depend on the relative association constant ($k_{assoc}$) which is related to the concentration of interacting peptides. Thus, subtle changes in the relative peptide concentrations may obscure potentially altered interactions. In order to provide control for such concentration-dependent processes between experiments, the molar concentration of the GST-fusion protein and the molar concentration of the IVTT sample were determined. Furthermore, clear changes in interaction between hMLH1 and hPMS2 were observed by the inventors using a similar assay system that correlates with alterations known to be mutations, rather than polymorphisms.

The results of the experiments presented in this Example are now described.

GST Interaction Assay

As described elsewhere herein, a physical interaction may be demonstrated between hMSH2 and either of hMSH3 and hMSH6 using immunoprecipitation (IP) reactions with anti-hMSH2 antibodies, which have been described in the art and are publicly available. However, interaction-region mapping experiments using truncation mutants of hMSH3 and hMSH6 resulted in elevated background as a result of anti-hMSH2 antibody binding to the truncated probes. In addition, this IP assay did not appear sensitive enough to detect weak interactions.

For these reasons, the alternative assay described herein was developed. This assay relies on the use of a GST-fusion protein expressed in *E. coli* as a "bait" and in vitro transcribed and translated (IVTT) protein as "prey". This assay proved to be effective for all of the GST-fusion MutS homolog probe combinations used in the studies described in this application. These GST-fusion MutS homolog probe combinations included GST-hMSH2:IVTT-hMSH3, GST-hMSH3:IVTT-hMSH2, GST-hMSH2:IVTT-hMSH6, and GST-hMSH6:IVTT-hMSH2. The interaction for each of these IVTT full-length peptides was specific for the corresponding GST-hMSH(X) fusion protein, as evidenced by the observation that nearly undetectable background non-specific binding was demonstrated by incubation and centrifugal precipitation of the IVTT-MSH(Y) with:

1) GST-agarose beads alone;
2) *E. coli* lysate +GST-agarose beads; and
3) pGEX (the GST moiety alone) +GST-agarose beads as controls.

Furthermore, densitometric comparison of the PAGE lanes containing only pGEX with PAGE lanes containing GST-hMSH(X) demonstrated that the signal-to-background ratio in this assay approaches 100. These results suggested that this bait-prey system was sufficient to map the interaction regions of the hMSH2–hMSH3 and the hMSH2–hMSH6 heterodimers.

In these studies, a clear interaction between MSH homologs could be demonstrated by comparing association of GST alone and IVTT-MSH(Y) with association of GST-MSH(X) and IVTT-MSH(Y), where X and Y are independently 2, 3, or 6. Furthermore, this assay provided a qualitative measure of interaction efficiency, because each experiment contained a nearly identical molar ratio of GST-MSH(X) and IVTT-MSH(Y). In addition, the GST-hMSH3 and GST-hMSH6 fusion proteins were demonstrated to be active for mis-pair binding when they are combined with purified hMSH2. These results indicate that the structure of the hMSH3 and hMSH6 proteins is not substantially altered by fusion to GST.

Interaction Regions of hMSH2 and hMSH3

Figure 12:
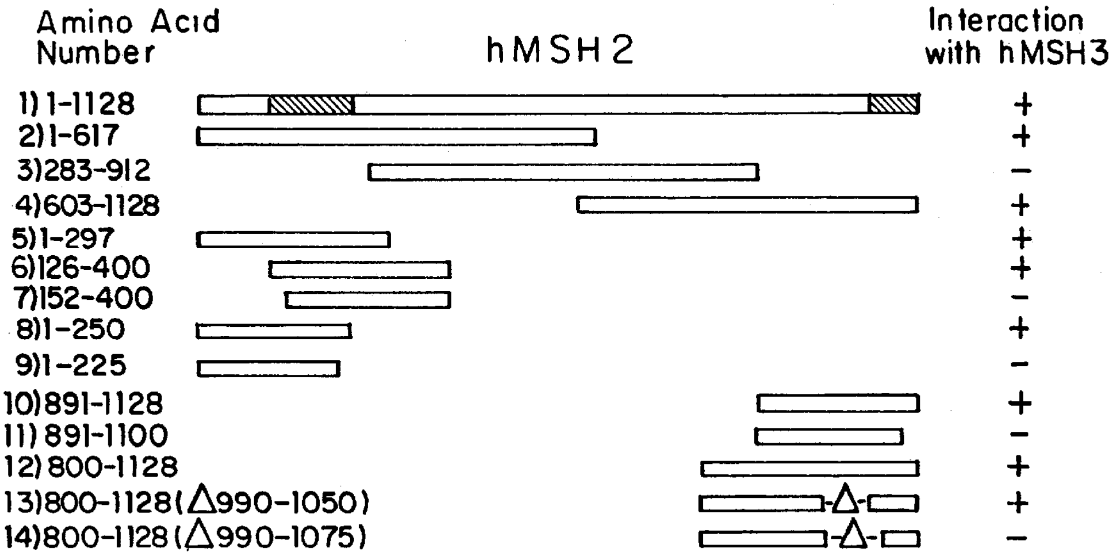
FIG. 12 is a diagram which indicates the primary structure of $^{35}S$-labeled IVTT-hMSH3 polypeptides used to identify approximate boundaries of hMSH2-interaction regions of hMSH3. "Amino Acid Number" refers to the amino acid residues of hMSH3 which the corresponding IVTT-hMSH3 polypeptide comprised. The rectangular entities in the central part of the figure represent relative positions of the amino acid residues which the corresponding IVTT-hMSH3 polypeptide comprised with respect to full length hMSH3, which is represented by polypeptide 1). The symbol, Δ, indicates a deleted region of a polypeptide. The shaded regions of polypeptide 1) represent the hMSH2-interaction regions of hMSH3. "Interaction with hMSH2" indicates whether or not the corresponding polypeptide interacted with GST-hMSH2.

The regions of hMSH3 which interact with hMSH2 were determined, as illustrated in FIG. 12. Truncated hMSH3 polypeptides were constructed such that the protein was represented by three overlapping polypeptides, as illustrated in FIG. 12, polypeptides 2–4. It was determined that there are two separate regions of hMSH3 that interact with hMSH2. It was recognized that an amino-terminal region of hMSH3 and a carboxy-terminal region of hMSH3 are involved in interactions with hMSH2, as illustrated, for example, by the abilities of polypeptides 5 and 10 in FIG. 12 to interact with GST-hMSH2. The amino-terminal region was determined to be located within the region of hMSH3 bounded by amino acid residues 126 and 250, as indicated by the abilities of polypeptides 6–9 in FIG. 12 to interact with GST-hMSH2. Because the level of IVTT expression was insufficient for polypeptides comprising fewer than one hundred amino acids, the carboxy-terminal region was mapped using an internal deletion strategy. Using this strategy, the carboxy-terminal interaction region was determined to be located within the region of hMSH3 bounded by amino acid residues 1050 and 1128, as indicated by the abilities of polypeptides 10–14 in FIG. 12 to interact with GST-hMSH2.

Figure 13:
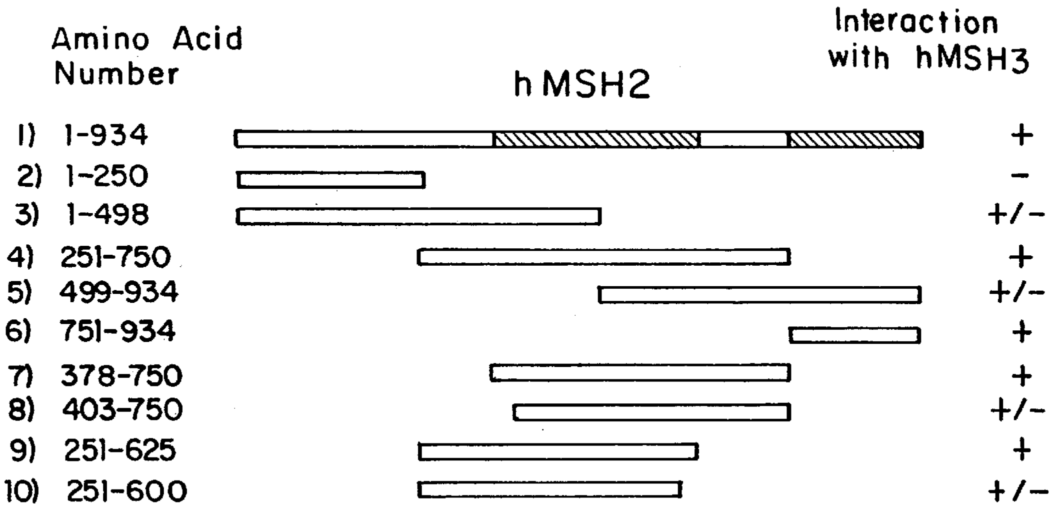
FIG. 13 is a diagram which indicates the primary structure of $^{35}S$-labeled IVTT-hMSH2 polypeptides used to identify approximate boundaries of hMSH3-interaction regions of hMSH2. "Amino Acid Number" refers to the amino acid residues of hMSH2 which the corresponding IVTT-hMSH2 polypeptide comprised. The rectangular entities in the central part of the figure represent relative positions of the amino acid residues which the corresponding IVTT-hMSH2 polypeptide comprised with respect to full length hMSH2, which is represented by polypeptide 1). The shaded regions of polypeptide 1) represent the hMSH3-interaction regions of hMSH2. "Interaction with hMSH3" indicates whether or not the corresponding polypeptide interacted with GST-hMSH3.

The locations of regions of hMSH2 which interact with hMSH3 were determined in a similar fashion. The regions of hMSH2 which interact with hMSH3 were determined, as illustrated in FIG. 13. Truncated hMSH2 polypeptides were constructed such that the protein was represented by four overlapping polypeptides, as illustrated in FIG. 13, polypeptides 2–5. It was determined that hMSH2 comprises two regions which are involved in interaction with hMSH3, as indicated by the abilities of polypeptides 1–6 in FIG. 13 to interact with GST-hMSH3. An amino-terminal region was determined to be located within the region of hMSH2 bounded by amino acid residues 378 and 625, as indicated by the abilities of polypeptides 7–10 in FIG. 13 to interact with GST-hMSH3. The amino acid boundaries of the carboxy-terminal interaction region of hMSH2 were not resolved with precision, due to sub-optimal signal strength. Nonetheless, the data illustrated in FIG. 13 indicate that the carboxy-terminal interaction region of hMSH2 may at least be localized in the region bounded by amino acid residues 751 and 934 (the carboxy terminus), as indicated by the abilities of polypeptide 6 in FIG. 13 to interact with GST-hMSH3.

Because there were two interaction regions between hMSH2 and hMSH3, a system was designed to determine the linear orientation of the two regions. GST fusion proteins comprising truncated hMSH3 polypeptides were constructed. A GST-hMSH3 fusion protein comprising hMSH3 amino acid residues 1–297 comprised the consensus amino-terminal interaction region. A GST-hMSH3 fusion protein comprising hMSH3 amino acid residues 1025–1128) comprised the consensus carboxy-terminal interaction region. These two fusion proteins were used as "bait" against a series of hMSH2 "prey" truncation mutants. We found that non-truncated hMSH2 interacted with both the GST-hMSH3 fusion protein, as indicated by the ability of polypeptide 1 in FIG. 14 to interact with both the GST-hMSH3 fusion protein comprising the consensus amino-terminal interaction region and the GST-hMSH3 fusion protein comprising the consensus carboxy-terminal interaction region. The GST-hMSH3 fusion protein comprising the consensus amino-terminal interaction region interacted most strongly with amino acid residues 251–750 of hMSH2 protein, as indicated by the ability of polypeptide 4 in FIG. 14 to interact with this GST-hMSH3 fusion protein. The GST-hMSH3 fusion protein comprising the consensus carboxy-terminal interaction region interacted most strongly with amino acid residues 751–934 of hMSH2 protein, as indicated by the ability of polypeptides 5, 6, 7, and 8 in FIG. 14 to interact with this GST-hMSH3 fusion protein.

These results indicate that the amino-terminal interaction region of hMSH3 normally interacts with the amino-terminal interaction region of hMSH2 and that the carboxy-region interaction region of hMSH3 normally interacts with the carboxyl region interaction region of hMSH2. Use of the GST-hMSH3 fusion protein comprising the consensus carboxy-terminal interaction region permitted further resolution of the carboxy-terminal interaction region of hMSH2. It was determined that the carboxy-terminal interaction region of hMSH2 is bounded by amino acid residues 875 and 934, as indicated by the ability of polypeptide 8 in FIG. 14 to interact with this GST-hMSH3 fusion protein.

Interaction Regions of hMSH2 and hMSH6

Using a similar strategy, the locations of the interaction regions of hMSH2 and hMSH6 were determined. It was recognized that an amino-terminal region of hMSH6 and a carboxy-terminal region of hMSH6 are involved in interactions with hMSH2, as illustrated, for example, by the abilities of polypeptides 1–6 in FIG. 15 to interact with GST-hMSH2. The amino-terminal region was determined to be located within the region of hMSH6 bounded by amino acid residues 326 and 575, as indicated by the abilities of polypeptides 7–10 in FIG. 15 to interact with GST-hMSH2. The carboxy-terminal region was determined to be located within the region of hMSH6 bounded by amino acid residues 953 and 1360, as indicated by the abilities of polypeptide 6 to interact with GST-hMSH2.

The regions of hMSH2 which interact with hMSH6 were determined, as illustrated in FIG. 16. Truncated hMSH2 polypeptides were constructed such that the protein was represented by four overlapping polypeptides, as illustrated in FIG. 16, polypeptides 2–5. It was determined that hMSH2 comprises two regions which are involved in interaction with hMSH6, as indicated by the abilities of polypeptides 1–6 in FIG. 15 to interact with GST-hMSH6. The amino-terminal region was determined to be located within the region of hMSH2 bounded by amino acid residues 378 and 625, as indicated by the abilities of polypeptides 7–10 in FIG. 15 to interact with GST-hMSH6. Using a GST fusion protein which contained a truncation mutant of hMSH6 comprising amino acid residues 1302–1360, it was determined that the carboxyl terminal interaction region of hMSH2 is located within the region of hMSH2 bounded by amino acid residues 875 and 934, as indicated by the ability of polypeptide 8 in FIG. 17 to interact with this GST fusion protein. The ability of polypeptide 8 in FIG. 17 to interact with this GST fusion protein also indicates that the carboxy-terminal interaction region of hMSH6 is bounded by amino acid residues 1302 and 1360.

These results indicate that the same amino acid regions of hMSH2 are involved in the interactions between hMSH2 and hMSH3 and the interactions between hMSH2 and hMSH6.

The linear orientation of the hMSH2–hMSH6 interaction regions was determined. Using IVTT amino-terminal and carboxy-terminal hMSH2 interaction regions and GST fusion proteins comprising the amino-terminal and carboxy-terminal interaction regions of hMSH6, it was determined that the amino-terminal interaction region of hMSH6 interacts with the amino-terminal interaction region of hMSH2, as indicated by the ability of polypeptides 3–5 in FIG. 17 to interact with the GST fusion protein comprising the amino-terminal interaction region of hMSH6. It was further determined that the carboxy-terminal interaction region of hMSH6 interacts with the carboxy-terminal interaction region of hMSH2, as indicated by the ability of polypeptides 5–8 in FIG. 17 to interact with the GST fusion protein comprising the carboxy-terminal interaction region of hMSH6. Thus, the linear orientation of the interaction regions of the hMSH2:hMSH6 heterodimer is identical to that of the hMSH2:hMSH3 heterodimer.

Interaction Regions of hMSH2 with Itself hMSH2 homodimers bind mismatched duplex DNA (Acharya et al., 1996, Proc. Natl. Acad. Sci. USA 93:13629–13634). Using a GST-hMSH2 fusion protein comprising hMSH2 amino acid residues 751–934, it was determined that this portion of hMSH2 (i.e. the carboxy-terminal interaction region) interacts with the carboxy terminus of hMSH2. Thus, the hMSH2 homodimer exhibits the same carboxy-terminal interaction pattern that was observed between hMSH2 and either of hMSH3 and hMSH6.

The Effect of hMSH2 Mutations Observed in HNPCC Kindreds on hMSH(X):hMSH(Y) Interaction Several HNPCC-associated missense mutations have been described which are located within one of the two interaction regions of hMSH2 identified herein. Six of these HNPCC-associated mutations were constructed, and the effect of the mutations on hMSH(X):hMSH(Y) interaction were investigated, wherein X and Y are independently 2, 3, or 6. The six HNPCC-associated mutations were those designated L390V, K393M, R524P, N596D, P622L, and T905R. These mutations are described in the HNPCC database (Peltomalei et al., 1997).

Interaction experiments were performed using mutated hMSH2 fragments which comprised either only an amino-terminal interaction region or a carboxy-terminal interaction region to eliminate any confusion that the presence of multiple interaction regions might generate. These hMSH2 IVTT mutant consensus interaction regions were examined for interaction with GST fusion proteins which comprised either full length hMSH3 or full length hMSH6. No difference could be discerned between binding of any mutated hMSH2 fragment to either of the fusion proteins and binding of a corresponding wild type hMSH2 fragment to either of the fusion proteins. These results suggest that altered interaction between hMSH2 and either hMSH3 or hMSH6 are not likely to be causative functional defects resulting in HNPCC.

The results of the experiments described in this Example suggest a model for regional interactions of hMSH2 with hMSH3 and with hMSH6. This model is illustrated in FIG. 18. The results described herein indicate that hMSH2 employs the same interaction regions, regardless of whether it interacts with hMSH3 or with hMSH6. These interactions are mediated by two distinct regions of hMSH2, an amino-terminal interaction region bounded by amino acid residues 378 and 625 and a carboxy-terminal interaction region bounded by amino acid residues 875 and 934. The adenine nucleotide binding region and the putative helix-turn-helix motif of hMSH2 are not contained within either of these regions. Thus, the results described in this Example indicate that it is unlikely that helix-turn-helix is essential for interaction of hMSH2 with hMSH3 or with hMSH6. FIG. 18 illustrates both the relative positions and the linear orientation of the interaction regions of hMSH2, hMSH3, and hMSH6.

Since hMSH3 and hMSH6 appear to contact hMSH2 within the same binding regions, the amino terminal and carboxyl terminal regions of hMSH3 and hMSH6 were aligned and compared. The amino terminal interaction regions of hMSH3 and hMSH6 exhibited little identifiable homology. The carboxyl terminal interaction regions of hMSH3 and hMSH6 exhibited moderate homology, 16 of 60 residues being identical. The carboxyl-terminal regions of hMSH3 and hMSH6 may provide a conserved function for these proteins such as, but not limited to, protein-protein interaction.

EXAMPLE 5 hMSH5, A Human MutS Homolog that Participates in the Second Meiotic Division In the experiments presented in this Example, the human MSH5 protein (hMSH5) and the cDNA sequence encoding it are described. The msh5 gene is located at chromosome 6p22-21, and is involved in meiosis, as evidenced by expression of msh5 in the testes and confinement of such expression to secondary spermatocytes and developing spermatids. hMSH5 specifically interacts with hMSH4, confirming the generality of functional heterodimeric interactions in eukaryotic MutS homologs. The hMSH4:hMSH5 heterodimer may thus be analogized with the hMSH2:hMSH3 and hMSH2:hMSH6 heterodimers.

The materials and methods described in the experiments presented in this Example are now described.

Cloning the hMSH4 and hMSH5 cDNAs

A search of the NCBI EST database indicated that a 466-base pair sequence derived from Soars human fetal liver spleen cDNA (T67203) exhibited significant homology with both yeast MSH3 and yeast MSH5. The amino acid sequence of the yeast and the human MSH2 homologs were used to screen the Human Genome Sciences (HGS, Bethesda, Md.) computer database using TFASTA computer software designed by the Genetics computer Group (GCG, University of Wisconsin). The HGS database contains nucleotide sequence information of expressed sequence tags (ESTs) which identify a diverse collection of cDNAs derived from more than 400 cDNA libraries (Adams et al., 1991, Science 252:1651–1656). One EST (designated C4) was determined to exhibit significant homology, but not identity, to yeast and human MSH2 and MSH3 protein sequences.

Two PCR fragments were amplified using primers derived from these two EST sequences, which were identified in cDNA derived from human testis. The PCR product were used to screen a normal human testis cDNA library (obtained from Clontech, Palo Alto, Calif.) using conventional plaque hybridization techniques. One of the primer sets derived from C4 yielded a consistent sequence and identified numerous phage clones. This set of primers comprised a forward primer (5'-ACGCCATCTT CACACGAAT-3'; SEQ ID NO: 31) and a reverse primer (5'-TGCAGTGGCA TTGTTCACT-3'; SEQ ID NO: 32). Six clones were identified which were amplified using these primers, and these clones were excised using the pDR2 phagemid, according to the manufacturer's recommendations. The six clones were subcloned into pBSK (Stratagene, La Jolla, Calif.), and double strand sequencing of the six clones was performed using the PRISM™ Ready Reaction DyeDeoxy Terminator Cycle Sequencing Kit and an Applied Biosystems 377 Sequencer (Foster City, Calif.).

One clone, designated b29, comprised an open reading frame (ORF) 2505 base pairs in length. This ORF comprised one STOP codon N-terminal to the start methionine codon and one STOP codon at a position corresponding to the C-terminus of the protein encoded by the ORF. The completeness of the N-terminal region of the ORF was confirmed by performing a RACE reaction using human normal testis cDNA (Clontech, Palo Alto, Calif.), as described (Apte et al., 1993, BioTechniques 15:890–893). The EST sequence obtained from NCBI (T67203) was found to be located in the C-terminal portion of the b29 ORF.

Clone b29 was further subcloned into pGEX (Pharmacia, Piscataway, N.J.) for expression of the GST fusion protein in *E. coli* XL1 Blue (Stratagene, La Jolla, Calif.) and into pET29a (Clontech, Palo Alto, Calif.) for in vitro transcription and translation (IVTT) using restriction endonucleases NdeI and NotI (New England Biolabs, Beverley, Mass.).

An hMSH4 clone was obtained from human testis cDNA (Clontech, Palo Alto, Calif.) by PCR amplification and subsequent ligation into the pCR2.1 vector using a TA cloning kit (Invitrogen, San Diego, Calif.). The primer sequences which were used in these reactions included an outer forward primer (5'-GGAAGGTTTG GGAGGATGC TGAGG-3'; SEQ ID NO: 33), a reverse primer (5'-ATTGTGATTA TTCTTCAGTC TT-3'; SEQ ID NO: 34), a nested PCR: forward primer (5'-ATCTCGAGAT GCTGAG-GCCT GAG-3'; SEQ ID NO: 35), and a second reverse primer (5'-GCGCTAGCTT ATTCTTCAGT CTTTTC-3'; SEQ ID NO: 36). The nucleotide sequence of the amplified clone was confirmed by complete double strand sequencing of both strands.

The hMSH4 clone contained a deletion of a C residue in codon 18 and an insertion of a G residue in codon 20, resulting in V19S and V20S mutations. Furthermore, the hMSH4 clone contained a G→A mutation at base 1219 of the published sequence (numbered starting with the A in the ATG initiator codon), which resulted in an E407K amino acid substitution. In addition, an apparent polymorphism at codon 368 (CGC→AGA) was detected, which does not alter the coding Arg.

Chromosomal Mapping of hMSH5

PCR reactions were performed using the primers described above respectively, to screen the Genebridge-4™ Radiation Hybrid Panel (Hudson et al., 1995, Science 270:1945–1954). 35 amplification cycles were performed using an annealing temperature of 60° C. for 30 seconds followed by 72° C. for 1 minute. Fragments were visualized by agarose gel electrophoresis.

Northern Blotting

Three multiple tissue northern blots containing poly-A+ RNA obtained from a total of 23 different human tissues were obtained from Clontech (Palo Alto, Calif.). 50 nanograms of a fill length hMSH5 cDNA and a beta-actin cDNA control were radiolabeled using alpha-($^{32}$P)-dCTP by random primed labeling (Boehringer Mannheim, Germany). Northern Blots were hybridized according to the manufacturer's instructions. The blots were washed in 2×SSC containing 0.05% (w/v) SDS at room temperature (i.e. about 20° C.) for a total of 60 minutes and at 50° C. in 0.1×SSC, 0.1% (w/v) SDS for a total of 40 minutes. Phosphorimager screens were exposed for one day. A 2.5–2.6 kilobase transcript was detected at a high level in testis. Tissues with significantly lower expression levels included bone marrow, lymph nodes, brain, and spinal cord.

Antibodies

Five different 15-mer peptides were synthesized, each corresponding to predicted immunogenic regions of the hMSH5 protein. These peptides were conjugated to hemocyanin, and polyclonal antibodies were raised in rabbits (H.T.I. Bio-Products, Ramona, Calif.). Antibody clone C924-2 was found to be most sensitive and specific in Western Blot experiments and was purified over a Protein-A column for Western analysis. Further affinity purification of the antibody was performed using a crude lysate of SF9 insect cells overexpressing hMSH5 protein. hMSH5 protein lysate was separated by SDS-PAGE, transferred to nitrocellulose and the hMSH5 specific region excised and used to affinity purify the antibody as described (Wilson et al., 1995, Cancer Res. 55:5146–5150).

Immunohistochemistry 5-micron sections of formalin-fixed and paraffin embedded tissues were cut onto Neoprene coated slides (Aldrich Chemicals, Milwaukee, Wis.). After de-paraffinization, including a 30 minute methanolic peroxide block for endogenous peroxidase activity (Leica Autostainer, Leica, Deerfield, Ill.), the slides were subjected to microwave radiation in 200 milliliters of Chem.Mate H.I.E.R buffer, pH 5.5–5.7 (Ventana Medical Systems, Tucson, Ariz.) at high energy for 5 minutes using a Panasonic Microwave #NN-5602A (Franklin PK, Ill.). 50 milliliters of water were replaced for additional microwave exposure for 4 minutes at high energy.

Immunostaining using the catalyzed signal amplification system (DAKO™, Carpinteria, Calif.) was performed according to the manufacturer's instructions. Incubation with Protein-A and hMSH5 specific affinity purified polyclonal antibody was performed for 50 minutes at room temperature at concentrations of 1:800 or 1:2000, respectively, using the hMSH2 polyclonal antibody. For counter staining with Harris Hematoxylin (Surgipath, Richmond, Ill.), the Leica Autostainer was used.

GST Fusion Protein Interaction Assay 500 microliters taken from a 5 milliliter overnight starter culture of cells which expressed an hMSH2-, hMSH3-, hMSH5-, or hMSH6-pGEX-fusion protein with (or non-fused pGEX as a negative control) was inoculated into 50 milliliters of Luria broth which contained 50 micrograms per milliliter ampicillin, and this culture was grown until the optical density at 600 nanometers was about 0.5. Protein expression was induced by addition of 0.1 millimolar (final concentration) IPTG for 2 hours at 30° C. Cells were pelleted and resuspended in 750 microliters of phosphate buffered saline containing protease inhibitors. A 10 minute digestion on ice using 1 milligram per milliliter lysozyme was then performed. After the addition of 0.2% (v/v) Triton X-100 and 1 millimolar dithiothreitol (final concentrations), the lysate was snap-frozen in liquid nitrogen and thawed twice. DNaseI (200 units per milliliter; Boehringer Mannheim, Germany) digestion was performed using the thawed lysate for 30 minutes on ice, after which cell debris was removed by centrifugation at 14,000 rpm at 4° C. for 30 minutes in a benchtop microfuge. Equal amounts of lysates obtained from cultures which separately expressed one of the fusion proteins (or GST alone as a negative control) were incubated on a rocking platform for 1 hour at 4° C. in the presence of 2 milligrams of glutathione-agarose beads (Sigma Chemical Co., St. Louis, Mo.) which had been pre-swollen in phosphate buffered saline containing protease inhibitors for 1 hour at room temperature. The beads were washed three times with 500 microliters of Interaction Buffer, which comprised 20 millimolar Tris-HCl, pH 7.5, 10% (v/v) Glycerol, 150 millimolar NaCl, 0.1% (v/v) Tween 20, 5 millimolar EDTA, 1 millimolar DTT, 0.75 milligrams per milliliter bovine serum albumin (Amresco, Solon, Ohio), and proteinase inhibitors). The beads were subsequently incubated in Interaction buffer for 1 hour at 4° C. on a rocking platform.

In vitro transcriptions and translation (IVTT) reactions were performed using 1 microgram each of hMSH2, hMSH3, hMSH5, and hMSH6 inserts (separately) in pET vectors and using the hMSH4 insert in pCR 2.1 using the TNT coupled reticulocyte lysate system (Promega, Madison, Wis.) according to the manufacturer's protocol. About 40 microcuries of $^{35}S$-methionine was incorporated into each protein. 5 microliters of individual IVTTs was added to 500 microliters of glutathione-agarose beads in Interaction buffer, and the mixture was incubated for 1 hour at 4° C. on the rocking platform. After three final washing steps, the supernatant was removed, and the beads were resuspended in 35 microliters of 2×Spear's buffer, boiled for 5 minutes, and centrifuged for 5 minutes at 14,000 rpm in a benchtop microfuge. 15 microliters of each reaction mixture was loaded onto separate lanes of an 8% (w/v) SDS-PAGE Gel (BioRad MiniProtean II), and electrophoresis was performed for about 90 minutes at 135 volts. PhosphorImager screens (Molecular Dynamics) were exposed to the dried gels for one day.

The results of the experiments described in this Example are now described.

Isolation an Chromosomal Map of hMSH5, a New Human MutS Homolog

Six clones which contained the EST later determined to correspond to msh5 were isolated, and the nucleotide sequence of both strands of the clone inserts were determined. Sequence analysis of clone b29 indicated the presence of an ORF 2505 base pairs in length. This ORF encoded putative 834-amino-acid protein, as indicated in FIGS. 19A–19C. The predicted molecular weight of the protein is 97 kilodaltons. A STOP codon was identified beyond the N-terminal end of the ORF, in the non-coding region, and the completeness of the ORF was confirmed by T-RACE analysis.

The Genebridge-4 Radiation Hybrid Panel for PCR products having a length corresponding to this ORF. In this way, the msh5 gene was located 6.94 cR from D6S478 on chromosome 6p22.1–21.3.

MSH5 Defines a New Family of MutS Homologs Involved in Sporulation and Meiosis

Of all eukaryotic and prokaryotic MutS homologs, the b29 clone was found to be most closely related to *Caenorhabdis elegans* MSH5 (29% amino acid identity) and *Saccharomyces cerevisiae* MSH5 (25% amino acid identity). A region encompassing the adenine nucleotide binding domain displayed approximately 60% amino acid identity among these homologues. The gene was therefore designated human msh5.

Among MutS homologs, the next closest relatives to hMSH5 are the MSH2 proteins. hMSH3 and hMSH6 proteins appear to be less closely related to hMSH5 than are the bacterial MutS proteins. In the present alignment, the MSH4 proteins appear to be the most divergent of the MutS homologs.

Expression of hMSH5

Human msh5 was determined to be transcribed at a high level in testis (FIG. 3). These results correspond to the observation that, in yeast, MSH5 expression was meiosis specific (Hollingsworth et al., 1995, Genes Dev. 9:1728–1739). The size of the human transcript corresponded to the length of the cDNA sequence, which is 2.5 kilobases. The presence of hMSH5 was detected in testis and tonsil tissue and, at very low levels, in two T- and B-cell tunor lines (Jurkat, CEM, Daudi, and GM 1500 cell lines) by Western Blot analysis. The Western signal in these autopsy tissues revealed low molecular weight protein band(s) that were likely degradation products of the significant autolytic reactions occurring in these samples. msh5 expression was also observed in human bone marrow and lymph node tissues. The presence of msh5 transcript in human tissues where B- and T-cells develop as well as expression in the T- and B-cell lines suggests a relationship to cellular development processes that include recombination events. However, it is also possible that the low levels of hMSH5 protein expression in the B- and T-cell lines could result from the fact that the cell lines are derived from hematologic malignancies and thus do not represent normal B- and T-cell precursors or other undefined factors. hMSH5 expression may also occur in human brain, spinal cord, and trachea tissues.

Western analysis suggested that several of the purified polyclonal antibodies derived from synthetic peptides are useful use immunohistochemical (IHC) studies. IHC stains for surgical specimens obtained from patients with various testicular tumors exhibited nuclear expression of hMSH5 in spermatids in statu nascendi in round and elongated spermatids (S3). In contrast, all of the preceding phases of spermatogenesis, as well as the spermatozoa themselves exhibited no expression of hMSH5. These observations indicate that hMSH5 has a specific role in the processes associated with the second meiotic division.

The testicular histology of the orchiectomy specimens was not entirely normal. Thus, it is possible that hMSH5 was abnormally expressed in the testicular samples obtained from surgical patients. In the samples examined, histological examination revealed occasional intratubular neoplasia and the presence of discrete lymphocytic infiltrates. However, spermatogenesis in these samples was still functioning sufficiently to produce mature sperm cells and a number of tubules were found where there was no evidence of neoplasia. Furthermore, staining of spermatids was evident in all of the tubules that appeared normal based on the presence of all stages of spermatogenesis. Textbook examples of normal tubules would show the cell types of spermatogenesis filling the entire tubule.

In contrast, hMSH2 is expressed in the nuclei at nearly all phases of spermatogenesis except for the round and elongated spermatids (where hMSH5 is expressed) and the spermatozoa. Sertoli cells exhibit faint nuclear staining with hMSH2-specific antibody. hMSH2 expression in tissue is clearly correlated with proliferation in general, which is exemplified in the experiments described in this Example by nuclear expression of hMSH2 in the seminoma. In addition, tissues that were positive for hMSH2 expression were also positive for expression of the proliferation marker Ki67. hMSH5 protein expression was absent in seminoma and other testicular malignancies such as embryonal cell carcinoma and mature and immature teratoma. Expression of hMSH5 was absent in dividing spermatogonium A, suggesting that expression is not induced during mitosis.

Protein Interaction Studies

Because hMSH2, hMSH3 and hMSH6 are, as described herein, known to act as heterodimers, interaction studies of hMSH5 with hMSH2, hMSH3, hMSH4 and hMSH6 were performed.

hMSH2 interacts strongly with hMSH3 and hMSH6, as described herein in Example 1. IVTT-hMSH5 did not interact with GST-hMSH2, -hMSH3 or hMSH6 fusion proteins. Similarly, none of IVTF-hMSH2, -hMSH3, and -hMSH6 interacted with GST-hMSH5. The lack of interaction of hMSH5 with hMSH2, hMSH3, and hMSH6 was confirmed as the intensity of the bands never exceeded the background. However, there was significant interaction of GST-hMSH5 with IVTT-hMSH4. Furthermore, a significant interaction of GST-hMSH3 fusion protein with IVTT-hMSH4 was observed. However, this potential interaction could not be confirmed since significant amounts of soluble GST-hMSH4 fusion protein could not be obtained. These results suggest that hMSH5 specifically interacts with hMSH4 alone.

In yeast, msh5 mutants have decreased spore viability, increased levels of Meiosis I chromosomal nondisjunction and decreased levels of reciprocal exchange between, but not within, chromosomes (Hollingsworth et al., 1995, Genes Dev. 9:1728–1739). This observation, combined with the results described herein suggest that hMSH5, and thus also hMSH4, is involved in meiotic processing. hMSH5 is located on chromosome 6p22-21 and is expressed at very high levels in the testis where meiosis occurs continually throughout adult life. Immunohistochemical examination of testicular sections revealed that the protein expression of hMSH5 occurred in developing round and elongated spermatids. Spermatogonia and primary spermatocytes did not express hMSH5, and expression of hMSH5 ended abruptly upon development of mature sperm. Because the expression of hMSH5 is exceedingly strong in the round spermatocytes, it is likely that expression of hMSH5 begins in the secondary spermatocyte. The expression pattern of hMSH5 is consistent with the phenotypes exhibited in yeast, since the meiosis I chromosomal non-disjunction occurs at the cellular division between the primary and secondary spermatocyte, at the stage where the expression of hMSH5 is likely to be initiated.

The observations described herein that hMSH5 was expressed in human tissues such as bone marrow and lymph nodes, where T-cell and B-cell development takes place, suggests that hMSH5 has a role in development of B-cells, T-cells, or both, and that defects in hMSH5 might result in hematological defects.

hMSH5 appears to specifically interact with hMSH4. No interaction with hMSH5 above background was observed for hMSH2, hMSH3 or hMSH6. Thus, it is likely that the hMSH4–hMSH5 heterodimer is specific and constitutes a functional interaction that is separate from hMSH2–hMSH3 and hMSH2–hMSH6 heterodimers. Based on the conservation of the adenine nucleotide binding and hydrolysis domain, it is likely that the hMSH4–hMSH5 heterodimer also functions as a molecular switch (Gradia et al., 1997, Cell 91:995–1005).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of modifying a ismaced duplex DNA, the method comprising contacting a MutS homolog (MSH) dimer and the mismatched duplex DNA in the presence of a binding solution comprising ADP and optionally ATP, wherein the concentration of ATP, if present, in the binding solution is less than about 3 micromolar, whereby the MSH dimer binds ADP, and ADP-bound MSH dimer associates with a mismatched region of the mismatched duplex DNA, thereby modifying the mismatched duplex DNA.

2. The method of claim 1, wherein the MSH dimer is selected from the group consisting of a prokaryotic MSH homodimer, a prokaryotic MSH heterodimer, a eukaryotic MSH homodimer, and a eukaryotic MSH heterodimer.

3. The method of claim 2, wherein the MSH dimer is a eukaryotic homodimer of a MutS homolog selected from the group consisting of a human MutS homolog, a murine MutS homolog, a rat MutS homolog, a Drosophila MutS homolog, a yeast MutS homolog, and a *Saccharomyces cerevisiae* MutS homolog.

4. The method of claim 3, wherein the eukaryotic MSH homodimer is an MSH2 homodimer.

5. The method of claim 2, wherein the MSH dimer is a eukaryotic MSH heterodimer which comprises MutS homologs independently selected from the group consisting of an MSH2 protein, an MSH3 protein, an MSH4 protein, an MSH5 protein, and an MSH6 protein.

6. The method of claim 5, wherein the MSH dimer is selected from the group consisting of an MSH2:MSH3 heterodimer, an MSH2:MSH6 heterodimer, and an MSH4:MSH5 heterodimer.

7. The method of claim 2, wherein the MSH dimer is a homodimer of *Escherichia coli* MutS.

8. The method of claim 1, wherein the MSH dimer concentration in the binding solution comprises at least 10 percent by weight.

9. The method of claim 1, wherein the concentration of ATP in the binding solution is less than about 0.3 micromolar.

10. The method of claim 9, wherein the concentration of ATP in the binding solution is less than about 30 nanomolar.

11. The method of claim 1, wherein at least one of the MSH dimer and the mismatched duplex DNA is bound to a support.

12. The method of claim 1, wherein the mismatched duplex DNA has at least one free end.

13. The method of claim 1, wherein the mismatched duplex DNA comprises a DNA strand generated by reverse transcription of mRNA obtained from an organism.

14. The method of claim 1, wherein the mismatched duplex DNA comprises a first DNA strand having a reference nucleotide sequence and a second DNA strand selected from the group consisting of a DNA strand obtained from an organism, a DNA strand obtained by amplification of at least a portion of a polynucleotide obtained from an organism, a DNA strand obtained by cleavage of a polynucleotide obtained from an organism, and a DNA strand obtained by reverse transcription of a polynucleotide obtained from an organism.

15. The method of claim 14, wherein the second DNA strand comprises at least a portion of a gene associated with a cancer in the organism.

16. The method of claim 15, wherein the organism is a human and wherein the gene is selected from the group consisting of an oncogene and a tumor suppressor gene.

17. The method of claim 16, wherein the gene is selected from the group consisting of abl, akt2, apc, bcl2α, bcl2β, bcl3, bcr, brca1, brca2, cbl, ccnd1, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf1, wnt1, wnt2, wt1, and yes1.

18. The method of claim 17, wherein the cancer is hereditary non-polyposis colon cancer and the gene is selected from the group consisting of mlh1, msh2, msh3, msh6, pms1, and pms2.

19. The method of claim 15, wherein the cancer is selected from the group consisting of a leukemia, a lymphoma, a meningioma, a mixed tumor of a salivary gland, an adenoma, a carcinoma, an adenocarcinoma, a sarcoma, a dysgerminoma, a retinoblastoma, a Wilms' tumor, a neuroblastoma, a melanoma, and a mesothelioma.

20. The method of claim 1, wherein the mismatched duplex DNA and the MSH dimer are contacted in the presence of at least one non-mismatched duplex DNA.

21. The method of claim 20, further comprising separating the MSH dimer from the non-mismatched duplex DNA after contacting the mismatched duplex DNA and the MSH dimer.

22. The method of claim 21, further comprising dissociating the mismatched duplex DNA and the MSH dimer after separating the MSH dimer from the non-mismatched duplex DNA and thereafter amplifying the mismatched duplex DNA.

23. The method of claim 22, wherein the MSH dimer is bound to a support prior to separating the non-mismatched duplex DNA from the MSH dimer.

24. The method of claim 23, wherein the non-mismatched duplex DNA is separated from the MSH dimer in the presence of a separating solution, wherein the concentration of ATP in the separating solution is less than about 30 nanomolar.

25. The method of claim 21, further comprising releasing the mismatched duplex DNA from the MSH dimer after separating the non-mismatched duplex DNA from the MSH dimer.

26. The method of claim 25, wherein the mismatched duplex DNA has at least one free end and is released from the MSH dimer by contacting the MSH dimer with a releasing solution selected from the group consisting of a solution comprising ATP and $Mg^{2+}$ ions, a solution comprising ATP and a magnesium-chelating agent, a solution comprising high salt, a solution comprising a gamma-modified ATP analog and $Mg^{2+}$ ions, and a solution comprising a gamma-hydrolysis-resistant ATP analog and $Mg^{2+}$ ions.

27. The method of claim 26, wherein the releasing solution comprises ATP and $Mg^{2+}$ ions.

28. The method of claim 25, wherein the mismatched duplex DNA does not have a free end and is released from the MSH dimer by contacting the MSH dimer with a releasing solution selected from the group consisting of a solution comprising a magnesium-chelating agent, a solution comprising high salt, a solution comprising a double-stranded DNA cleaving enzyme, ATP and $Mg^{2+}$ ions, a solution comprising a double-stranded DNA cleaving enzyme, a gamma-modified ATP analog, and $Mg^{2+}$ ions, and a solution comprising a double-stranded DNA cleaving enzyme, a gamma-hydrolysis-resistant ATP analog, and $Mg^{2+}$ ions.

29. The method of claim 1, further comprising contacting the MSH dimer with a MutL homolog after contacting the mismatched DNA and the MSH dimer.

30. The method of claim 1, further comprising detecting association of the MSH dimer with the mismatched duplex DNA.

31. The method of claim 30, wherein association of the MSH dimer with the mismatched duplex DNA is detected using an assay selected from the group consisting of a gel mobility shift assay, a filter binding assay, an immunological assay, a sedimentation centrifugation assay, a spectroscopic assay, an optical affinity assay, a DNA footprint assay, and a nucleolytic cleavage protection assay.

32. The method of claim 1, wherein the duplex DNA does not have a free end.

33. The method of claim 32, wherein the MSH dimer is present in molar excess with respect to the mismatched duplex DNA, whereby an average of more than one MSH dimer associates with one molecule of mismatched duplex DNA.

34. A method of modifying a mismatched duplex DNA which does not have a free end, the method comprising contacting the mismatched duplex DNA and an MSH dimer having ADP bound thereto with a binding solution which optionally comprises ATP, wherein the concentration of ATP, if present, in the binding solution is less than about 3 micromolar, whereby the dimer binds a mismatched region of the mismatched duplex DNA, thereby modifying the mismatched duplex DNA.

35. The method of claim 34, wherein the MSH dimer is selected from the group consisting of a prokaryotic MSH homodimer, a prokaryotic MSH heterodimer, a eukaryotic MSH homodimer, and a eukaryotic MSH heterodimer.

36. The method of claim 35, wherein the MSH dimer is a eukaryotic homodimer of a MutS homolog selected from the group consisting of a human MutS homolog, a murine MutS homolog, a rat MutS homolog, a Drosophila MutS homolog, a yeast MutS homolog, and a *Saccharomyces cerevisiae* MutS homolog.

37. The method of claim 36, wherein the eukaryotic MSH homodimer is an MSH2 homodimer.

38. The method of claim 35, wherein the MSH dimer is a eukaryotic MSH heterodimer which comprises MutS homologs independently selected from the group consisting of an MSH2 protein, an MSH3 protein, an MSH4 protein, an MSH5 protein, and an MSH6 protein.

39. The method of claim 38, wherein the MSH dimer is selected from the group consisting of an MSH2:MSH3 heterodimer, an MSH2:MSH6 heterodimer, and an MSH4:MSH5 heterodimer.

40. The method of claim 35, wherein the MSH dimer is a homodimer of *Escherichia coli* MutS.

41. The method of claim 34, wherein the MSH dimer concentration in the binding solution comprises at least 10 percent by weight.

42. The method of claim 34, wherein the concentration of ATP in the binding solution is less than about 0.3 micromolar.

43. The method of claim 42, wherein the concentration of ATP in the binding solution is less than about 30 nanomolar.

44. A method of detecting a difference between a sample nucleotide sequence and a reference nucleotide sequence, the method comprising a) annealing a first DNA strand and a second DNA strand to form a duplex DNA, i) wherein the first DNA strand has the sample nucleotide sequence ii) wherein the second DNA strand has a nucleotide sequence which is complementary to the reference nucleotide sequence, and iii) whereby if there is a difference between the sample nucleotide sequence and the reference nucleotide sequence then the duplex DNA is a mismatched duplex DNA;

b) thereafter contacting the duplex DNA and an MSH dimer in the presence of a binding solution comprising ADP and optionally ATP, wherein the concentration of ATP, if present, in the binding solution is less than about 3 micromolar, whereby the MSH dimer binds ADP, and ADP-bound MSH dimer binds the duplex DNA if the duplex DNA is a mismatched duplex DNA; and c) determining whether the MSH dimer is associated with the duplex DNA molecule, whereby association of the MSH dimer with the duplex DNA molecule is an indication that there is a difference between the sample nucleotide sequence and the reference nucleotide sequence.

45. The method of claim 44, wherein the MSH dimer is selected from the group consisting of a prokaryotic MSH homodimer, a prokaryotic MSH heterodimer, a eukaryotic MSH homodimer, and a eukaryotic MSH heterodimer.

46. The method of claim 45, wherein the MSH dimer is a eukaryotic homodimer of a MutS homolog selected from the group consisting of a human MutS homolog, a murine MutS homolog, a rat MutS homolog, a Drosophila MutS homolog, a yeast MutS homolog, and a *Saccharomyces cerevisiae* MutS homolog.

47. The method of claim 46, wherein the eukaryotic MSH homodimer is an MSH2 homodimer.

48. The method of claim 45, wherein the MSH dimer is a eukaryotic MSH heterodimer which comprises MutS homologs independently selected from the group consisting of an MSH2 protein, an MSH3 protein, an MSH4 protein, an MSH5 protein, and an MSH6 protein.

49. The method of claim 48, wherein the MSH dimer is selected from the group consisting of an MSH2:MSH3 heterodimer, an MSH2:MSH6 heterodimer, and an MSH4:MSH5 heterodimer.

50. The method of claim 45, wherein the MSH dimer is a homodimer of *Escherichia coli* MutS.

51. The method of claim 44, wherein the MSH dimer concentration in the binding solution comprises at least 10 percent by weight.

52. The method of claim 44, wherein the concentration of ATP in the binding solution is less than about 0.3 micromolar.

53. The method of claim 52, wherein the concentration of ATP in the binding solution is less than about 30 nanomolar.

54. A method of determining whether a mammal is predisposed for carcinogenesis, the method comprising a) annealing a first DNA strand and a second DNA strand to form a duplex DNA, i) wherein the first DNA strand has the nucleotide sequence of at least a portion of a gene selected from the group consisting of an oncogene and a tumor suppressor gene of the mammal, and ii) wherein the second DNA strand has a nucleotide sequence which is complementary to the nucleotide sequence of the gene portion, iii) whereby if there is a sequence difference between the first DNA strand and the second DNA strand then the duplex DNA is a mismatched duplex DNA;

b) thereafter contacting the duplex DNA and an MSH dimer in the presence of a binding solution comprising ADP and otionally ATP, wherein the concentration of ATP, if present, in the binding solution is less than about 3 micromolar, whereby the MSH dimer binds ADP, and ADP-bound MSH dimer binds the duplex DNA if the duplex DNA is a mismatched duplex DNA; and c) determining whetler the MSH dimer is associated with the duplex DNA, whereby association of the MSH dimer with the duplex DNA is an indication that the mammal is predisposed for carcinogenesis.

55. The method of claim 54, wherein the MSH dimer is selected from the group consisting of a prokaryotic MSH homodimer, a prokaryotic MSH heterodimer, a eukaryotic MSH homodimer, and a eukaryotic MSH heterodimer.

56. The method of claim 55, wherein the MSH dimer is a eukaryotic homodimer of a MutS homolog selected from the group consisting of a human MutS homolog, a murine MutS homolog, a rat MutS homolog, a Drosophila MutS homolog, a yeast MutS homolog, and a *Saccharomyces cerevisiae* MutS homolog.

57. The method of claim 56, wherein the eukaryotic MSH homodimer is an MSH2 homodimer.

58. The method of claim 55, wherein the MSH dimer is a eukaryotic MSH heterodimer which comprises MutS homologs independently selected from the group consisting of an MSH2 protein, an MSH3 protein, an MSH4 protein, an MSH5 protein, and an MSH6 protein.

59. The method of claim 58, wherein the MSH dimer is selected from the group consisting of an MSH2:MSH3 heterodimer, an MSH2:MSH6 heterodimer, and an MSH4:MSH5 heterodimer.

60. The method of claim 55, wherein the MSH dimer is a homodimer of *Escherichia coli* MutS.

61. The method of claim 54, wherein the MSH dimer concentration in the binding solution comprises at least 10 percent by weight.

62. The method of claim 54, wherein the concentration of ATP in the binding solution is less than about 0.3 micromolar.

63. The method of claim 62, wherein the concentration of ATP in the binding solution is less than about 30 nanomolar.

64. A method of determining whether the nucleotide sequence of a first copy of a genomic sequence differs from the nucleotide sequence of a second copy of the genomic sequence, the method comprising amplifying a region of each of the first copy and the second copy of the genomic sequence to yield amplified first copies and amplified second copies;

mixing and denaturing the amplified first copies and the amplified second copies to form a first mixture;

annealing the nucliec acids in the first mixture to form a second mixture comprising duplex DNAs, whereby if the nucleotide sequence of the first copy and the nucleotide sequence of the second copy of the genomic sequence differ then at least some of the duplex DNAs are mismatched duplex DNAs;

contacting the second mixture with an MSH dimer in a binding solution comprising ADP and optionally ATP, wherein the concentration of ATP, if present, in the binding solution is less than about 3 micromolar, whereby the MSH dimer binds ADP, and ADP-bound MSH dimer binds the mismatched duplex DNAs; and determining whether the MSH dimer is associated with at least some of the duplex DNAs, whereby association of the MSH dimer with at least some of the duplex DNAs is an indication that the nucleotide sequence of the first copy of the genomic sequence differs from the nucleotide sequence of the second copy of the genomic sequence.

65. The method of claim 64, wherein the MSH dimer is selected from the group consisting of a prokaryotic MSH homodimer, a prokaryotic MSH heterodimer, a eukaryotic MSH homodimer, and a eukaryotic MSH heterodimer.

66. The method of claim 65, wherein the MSH dimer is a eukaryotic homodimer of a MutS homolog selected from the group consisting of a human MutS homolog, a murine MutS homolog, a rat MutS homolog, a Drosophila MutS homolog, a yeast MutS homolog, and a *Saccharomyces cerevisiae* MutS homolog.

67. The method of claim 66, wherein the eukaryotic MSH homodimer is an MSH2 homodimer.

68. The method of claim 65, wherein the MSH dimer is a eukaryotic MSH heterodimer which comprises MutS homologs independently selected from the group consisting of an MSH2 protein, an MSH3 protein, an MSH4 protein, an MSH5 protein, and an MSH6 protein.

69. The method of claim 68, wherein the MSH dimer is selected from the group consisting of an MSH2:MSH3 heterodimer, an MSH2:MSH6 heterodimer, and an MSH4:MSH5 heterodimer.

70. The method of claim 65, wherein the MSH dimer is a homodimer of *Escherichia coli* MutS.

71. The method of claim 64, wherein the MSH dimer concentration in the binding solution comprises at least 10 percent by weight.

72. The method of claim 64, wherein the concentration of ATP in the binding solution is less than about 0.3 micromolar.

73. The method of claim 72, wherein the concentration of ATP in the binding solution is less than about 30 nanomolar.

74. A kit for screening a genomic region for a nucleotide sequence which differs from a reference nucleotide sequence, the kit comprising a pair of primers complementary to the ends of the region for amplifying the region;

ADP;

a DNA strand having the reference nuclcotide sequence;

at least two MutS homologs; and an instructional material which describes contacting the MutS homologs and annealed DNA in the presence of a binding solution comprising ADP, wherein the concentration of ATP in the binding solution is less tan about 3 micromolar, whereby in at least two of the MutS homologs dimerize in the binding solution, the dimer binds ADP, and ADP-bound dimer binds duplex DNA formed of the reference DNA and a complementary DNA if the duplex DNA is a mismatched duplex DNA.

75. The kit of claim 74, wherein each MutS homolog is independently selected from the group consisting of an MSH2 protein, an MSH3 protein, an MSH4 protein, an MSH5 protein, and an MSH6 protein.

76. The kit of claim 75, comprising MSH2 and MSH3 proteins.

77. The kit of claim 75, comprising MSH2 and MSH6 proteins.

78. The kit of claim 75, comprising MSH4 and MSH5 proteins.

79. A method of modifying a mismatched duplex DNA, the method comprising contacting an MSH dimer and the mismatched duplex DNA in the presence of a binding solution comprising ADP and optionally ATP, wherein the concentration of ADP in the binding solution is at least about ten times the concentration of ATP, if ATP is present in the binding solution, whereby the MSH dimer binds the mismatched region of the mismatched duplex DNA, thereby modifying the mismatched duplex DNA.

80. The method of claim 79, wherein the MSH dimer is selected from the group consisting of a prokaryotic MSH homodimer, a prokaryotic MSH heterodimer, a eukaryotic MSH homodimer, and a eukaryotic MSH heterodimer.

81. The method of claim 80, wherein the MSH dimer is a eukaryotic homodimer of a MutS homolog selected from the group consisting of a human MutS homolog, a murine MutS homolog, a rat MutS homolog, a Drosophila MutS homolog, a yeast MutS homolog, and a *Saccharomyces cerevisiae* MutS homolog.

82. The method of claim 81, wherein the eukaryotic MSH homodimer is an MSH2 homodimer.

83. The method of claim 80, wherein the MSH dimer is a eukaryotic MSH heterodimer which comprises MutS homologs independently selected from the group consisting of an MSH2 protein, an MSH3 protein, an MSH4 protein, an MSH5 protein, and an MSH6 protein.

84. The method of claim 83, wherein the MSH dimer is selected from the group consisting of an MSH2:MSH3 heterodimer, an MSH2:MSH6 heterodimer, and an MSH4:MSH5 heterodimer.

85. The method of claim 80, wherein the MSH dimer is a homodimer of *Escherichia coli* MutS.

86. The method of claim 79, wherein the MSH dimer concentration in the binding solution comprises at least 10 percent by weight.

87. The method of claim 79, wherein the concentration of ATP in the binding solution is less than about 0.3 micromolar.

88. The method of claim 87, wherein the concentration of ATP in the binding solution is less than about 30 nanomolar.

* * * * *

UNITED STATES PATENT AND TRADEMARK OFFICE

CERTIFICATE OF CORRECTION

PATENT NO. : 6,333,153 B1
DATED : December 25, 2001
INVENTOR(S) : Richard A. Fishel, Scott Gradia and Samir Acharya It is certified that error appears in the above-identified patent and that said Letters Patent is hereby corrected as shown below:

<u>Column 91,</u>
Line 34, "ismaced" should be replaced with -- mismatched --.

Signed and Sealed this

Seventh Day of May, 2002

*Attest:*

JAMES E. ROGAN

*Attesting Officer*

*Director of the United States Patent and Trademark Office*

SEQUENCE LISTING

```
<160> NUMBER OF SEQ ID NOS: 36

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence:  DNA
      Substrate
```

-continued

<400> SEQUENCE: 1
cggcgaattc caccaagctt gatcgctcga ggtaccagg 39

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: DNA Substrate

<400> SEQUENCE: 2
cctggtacct cgagcgatca agcttggtgg aattcgccg 39

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: DNA Substrate

<400> SEQUENCE: 3
cctggtacct cgagcgatcg agcttggtgg aattcgccg 39

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: DNA Substrate

<400> SEQUENCE: 4
aaagctggag ctgaagctta gcttaggatc atcgaggatc gagctcggtg caattcagcg 60
gtacccaatt cgccctatag t 81

<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence: DNA Substrate

<400> SEQUENCE: 5
actatagggc gaattgggta ccgctgaatt gcaccgagct cgatcctcga tgatcctaag 60
ctaagcttca gctccagctt t 81

<210> SEQ ID NO 6
<211> LENGTH: 81
<212> TYPE: DNA
<213> ORGANISM: Artificial Sequence
<220> FEATURE:
<223> OTHER INFORMATION: Description of Artificial Sequence: DNA Substrate

<400> SEQUENCE: 6
actatagggc gaattgggta ccgctgaatt gcaccgagct tgatcctcga tgatcctaag 60
ctaagcttca gctccagctt t 81

<210> SEQ ID NO 7
<211> LENGTH: 26

-continued

```
<212> TYPE: DNA
<213> ORGANISM: Artificial Sequence
<220> FEATURE:
<223> OTHER INFORMATION: Description of Artificial Sequence:  p53
      Primers

<400> SEQUENCE: 7

gtgtttcatt agttccccac cttgac                                           26


<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:  p53
      Primers

<400> SEQUENCE: 8

atgggaggct gccagtccta accc                                             24


<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:  p53
      Primers

<400> SEQUENCE: 9

gtgggaggga caaaagttcg aggcc                                            25


<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:  p53
      Primers

<400> SEQUENCE: 10

tttacggagc cctggcgctc gatgt                                            25


<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:  Mouse
      DXMIT6 Primers

<400> SEQUENCE: 11

accattcaaa ttggcaagg                                                   19


<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:  Mouse
      DXMIT6 Primers

<400> SEQUENCE: 12

gtggctcgag ttgtttgcag                                                  20


<210> SEQ ID NO 13
<211> LENGTH: 45
<212> TYPE: DNA
```

-continued

```
<213> ORGANISM: Artificial Sequence
<220> FEATURE:
<223> OTHER INFORMATION: Description of Artificial Sequence:  MSH
      Subcloning Linkers

<400> SEQUENCE: 13

gatccgagaa cctgtacttc cagggacata tggccatggg taccg                45


<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence:  MSH
      Subcloning Linkers

<400> SEQUENCE: 14

aattcggtac ccatggccat atgtccctgg aagtacaggt tctcg                45


<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence:  hMSH2
      Truncation Primers

<400> SEQUENCE: 15

gcggatccca tgg                                                   13


<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence:  hMSH2
      Truncation Primers

<400> SEQUENCE: 16

ggaggatccc ta                                                    12


<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:  hMSH2
      Truncation Primers

<400> SEQUENCE: 17

gcggatccca tggcagaagt gtccattgtg                                 30


<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:  hMSH2
      Truncation Primers

<400> SEQUENCE: 18

ggaggatccc atatgtagat tattaacagt tgg                             33


<210> SEQ ID NO 19
<211> LENGTH: 15
<212> TYPE: DNA
<213> ORGANISM: Artificial Sequence
```

-continued

<220> FEATURE:
<223> OTHER INFORMATION: Description of Artificial Sequence: hMSH2
      Primers

<400> SEQUENCE: 19
ggcggtatcc atatg 15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: hMSH2
      Primers

<400> SEQUENCE: 20
ggcatactcg agcta 15

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: DNA
      Linkers

<400> SEQUENCE: 21
gcggatccca tggattttct agagaaattc 30

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: DNA
      Linkers

<400> SEQUENCE: 22
ggacgcgtcg tcgacctaac cggtatctct gatgaaatac tc 42

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: hMSH3
      Primer

<400> SEQUENCE: 23
gcggtgaccg gt 12

<210> SEQ ID NO 24
<211> LENGTH: 21
<212> TYPE: PRT
<213> ORGANISM: Homo sapiens
<220> FEATURE:
<223> OTHER INFORMATION: region I of hMSH2

<400> SEQUENCE: 24

```
Leu Phe Asp Arg Gly Asp Phe Tyr Thr Ala His Gly Glu Asp Ala Leu
  1               5                  10                  15

Leu Ala Ala Arg Glu
             20
```

<210> SEQ ID NO 25
<211> LENGTH: 33

-continued

```
<212> TYPE: PRT
<213> ORGANISM: Homo sapiens
<220> FEATURE:
<223> OTHER INFORMATION: region II of hMSH2

<400> SEQUENCE: 25

Thr Pro Gln Gly Gln Arg Leu Val Asn Gln Trp Ile Lys Gln Pro Leu
  1               5                  10                  15

Met Asp Lys Asn Arg Ile Glu Glu Arg Leu Asn Leu Val Glu Ala Phe
             20                  25                  30

Val


<210> SEQ ID NO 26
<211> LENGTH: 28
<212> TYPE: PRT
<213> ORGANISM: Homo sapiens
<220> FEATURE:
<223> OTHER INFORMATION: region III of hMSH2

<400> SEQUENCE: 26

Leu Lys Ala Ser Arg His Ala Cys Val Glu Val Gln Asp Glu Ile Ala
  1               5                  10                  15

Phe Ile Pro Asn Asp Val Tyr Phe Glu Lys Asp Lys
             20                  25


<210> SEQ ID NO 27
<211> LENGTH: 104
<212> TYPE: PRT
<213> ORGANISM: Homo sapiens
<220> FEATURE:
<223> OTHER INFORMATION: region IV of hMSH2

<400> SEQUENCE: 27

Ile Ile Thr Gly Pro Asn Met Gly Gly Lys Ser Thr Tyr Ile Arg Gln
  1               5                  10                  15

Thr Gly Val Ile Val Leu Met Ala Gln Ile Gly Cys Phe Val Pro Cys
             20                  25                  30

Glu Ser Ala Glu Val Ser Ile Val Asp Cys Ile Leu Ala Arg Val Gly
         35                  40                  45

Ala Gly Asp Ser Gln Leu Lys Gly Val Ser Thr Phe Met Ala Glu Met
     50                  55                  60

Leu Glu Thr Ala Ser Ile Leu Arg Ser Ala Thr Lys Asp Ser Leu Ile
 65                  70                  75                  80

Ile Ile Asp Glu Leu Gly Arg Gly Thr Ser Thr Tyr Asp Gly Phe Gly
                 85                  90                  95

Leu Ala Trp Ala Ile Ser Glu Tyr
            100


<210> SEQ ID NO 28
<211> LENGTH: 41
<212> TYPE: PRT
<213> ORGANISM: Homo sapiens
<220> FEATURE:
<223> OTHER INFORMATION: region V of hMSH2

<400> SEQUENCE: 28

Leu Thr Met Leu Tyr Gln Val Lys Lys Gly Val Cys Asp Gln Ser Phe
  1               5                  10                  15

Gly Ile His Val Ala Glu Leu Ala Asn Phe Pro Lys His Val Ile Glu
             20                  25                  30

Cys Ala Lys Gln Lys Ala Leu Glu Leu
```

35 40

<210> SEQ ID NO 29
<211> LENGTH: 834
<212> TYPE: PRT
<213> ORGANISM: Homo sapiens

<400> SEQUENCE: 29

```
Met Ala Ser Leu Gly Ala Asn Pro Arg Arg Thr Pro Gln Gly Pro Arg
  1               5                  10                  15

Pro Gly Ala Ala Ser Ser Gly Phe Pro Ser Pro Ala Pro Val Pro Gly
             20                  25                  30

Pro Arg Glu Ala Glu Glu Glu Glu Val Glu Glu Glu Glu Glu Leu Ala
         35                  40                  45

Glu Ile His Leu Cys Val Leu Trp Asn Ser Gly Tyr Leu Gly Ile Ala
     50                  55                  60

Tyr Tyr Asp Thr Ser Asp Ser Thr Ile His Phe Met Pro Asp Ala Pro
 65                  70                  75                  80

Asp His Glu Ser Leu Lys Leu Leu Gln Arg Val Leu Asp Glu Ile Asn
                 85                  90                  95

Pro Gln Ser Val Val Thr Ser Ala Lys Gln Asp Glu Asn Met Thr Arg
            100                 105                 110

Phe Leu Gly Lys Leu Ala Ser Gln Glu His Arg Glu Pro Lys Arg Pro
        115                 120                 125

Glu Ile Ile Phe Leu Pro Ser Val Asp Phe Gly Leu Glu Ile Ser Lys
    130                 135                 140

Gln Arg Leu Leu Ser Gly Asn Tyr Ser Phe Ile Pro Asp Ala Met Thr
145                 150                 155                 160

Ala Thr Glu Lys Ile Leu Phe Leu Ser Ser Ile Ile Pro Phe Asp Cys
                165                 170                 175

Leu Leu Thr Val Arg Ala Leu Gly Gly Leu Leu Lys Phe Leu Gly Arg
            180                 185                 190

Arg Arg Ile Gly Val Glu Leu Glu Asp Tyr Asn Val Ser Val Pro Ile
        195                 200                 205

Leu Gly Phe Lys Lys Phe Met Leu Thr His Leu Val Asn Ile Asp Gln
    210                 215                 220

Asp Thr Tyr Ser Val Leu Gln Ile Phe Lys Ser Glu Ser His Pro Ser
225                 230                 235                 240

Val Tyr Lys Val Ala Ser Gly Leu Lys Glu Gly Leu Ser Leu Phe Gly
                245                 250                 255

Ile Leu Asn Arg Cys His Cys Lys Trp Gly Glu Lys Leu Leu Arg Leu
            260                 265                 270

Trp Phe Thr Arg Pro Thr His Asp Leu Gly Glu Leu Ser Ser Arg Leu
        275                 280                 285

Asp Val Ile Gln Phe Phe Leu Leu Pro Gln Asn Leu Asp Met Ala Gln
    290                 295                 300

Met Leu His Arg Leu Leu Gly His Ile Lys Asn Val Pro Leu Ile Leu
305                 310                 315                 320

Lys Arg Met Lys Leu Ser His Thr Lys Val Ser Asp Trp Gln Val Leu
                325                 330                 335

Tyr Lys Thr Val Tyr Ser Ala Leu Gly Leu Arg Asp Ala Cys Arg Ser
            340                 345                 350

Leu Pro Gln Ser Ile Gln Leu Phe Arg Asp Ile Ala Gln Glu Phe Ser
        355                 360                 365
```

-continued

```
Asp Asp Leu His His Ile Ala Ser Leu Ile Gly Lys Val Val Asp Phe
    370                 375                 380

Glu Gly Ser Leu Ala Glu Asn Arg Phe Thr Val Leu Pro Asn Ile Asp
385                 390                 395                 400

Pro Glu Ile Asp Glu Lys Lys Arg Arg Leu Met Gly Leu Pro Ser Phe
                405                 410                 415

Leu Thr Glu Val Ala Arg Lys Glu Leu Glu Asn Leu Asp Ser Arg Ile
            420                 425                 430

Pro Ser Cys Ser Val Ile Tyr Ile Pro Leu Ile Gly Phe Leu Leu Ser
        435                 440                 445

Ile Pro Arg Leu Pro Ser Met Val Glu Ala Ser Asp Phe Glu Ile Asn
    450                 455                 460

Gly Leu Asp Phe Met Phe Leu Ser Glu Glu Lys Leu His Tyr Arg Ser
465                 470                 475                 480

Ala Arg Thr Lys Glu Leu Asp Ala Leu Leu Gly Asp Leu His Cys Glu
                485                 490                 495

Ile Arg Asp Gln Glu Thr Leu Leu Met Tyr Gln Leu Gln Cys Gln Val
            500                 505                 510

Leu Ala Arg Ala Ala Val Leu Thr Arg Val Leu Asp Leu Ala Ser Arg
        515                 520                 525

Leu Asp Val Leu Leu Ala Leu Ala Ser Ala Ala Arg Asp Tyr Gly Tyr
    530                 535                 540

Ser Arg Pro Arg Tyr Ser Pro Gln Val Leu Gly Val Arg Ile Gln Asn
545                 550                 555                 560

Gly Arg His Pro Leu Met Glu Leu Cys Ala Arg Thr Phe Val Pro Asn
                565                 570                 575

Ser Thr Glu Cys Gly Gly Asp Lys Gly Arg Val Lys Val Ile Thr Gly
            580                 585                 590

Pro Asn Ser Ser Gly Lys Ser Ile Tyr Leu Lys Gln Val Gly Leu Ile
        595                 600                 605

Thr Phe Met Ala Leu Val Gly Ser Phe Val Pro Ala Glu Glu Ala Glu
    610                 615                 620

Ile Gly Ala Val Asp Ala Ile Phe Thr Arg Ile His Ser Cys Glu Ser
625                 630                 635                 640

Ile Ser Leu Gly Leu Ser Thr Phe Met Ile Asp Leu Asn Gln Val Ala
                645                 650                 655

Lys Ala Val Asn Asn Ala Thr Ala Gln Ser Leu Val Leu Ile Asp Glu
            660                 665                 670

Phe Gly Lys Gly Thr Asn Thr Val Asp Gly Leu Ala Leu Leu Ala Ala
        675                 680                 685

Val Leu Arg His Trp Leu Ala Arg Gly Pro Thr Cys Pro His Ile Phe
    690                 695                 700

Val Ala Thr Asn Phe Leu Ser Leu Val Gln Leu Gln Leu Leu Pro Gln
705                 710                 715                 720

Gly Pro Leu Val Gln Tyr Leu Thr Met Glu Thr Cys Glu Asp Gly Asn
                725                 730                 735

Asp Leu Val Phe Phe Tyr Gln Val Cys Glu Gly Val Ala Lys Ala Ser
            740                 745                 750

His Ala Ser His Thr Ala Ala Gln Ala Gly Leu Pro Asp Lys Leu Val
        755                 760                 765

Ala Arg Gly Lys Glu Val Ser Asp Leu Ile Arg Ser Gly Lys Pro Ile
    770                 775                 780

Lys Pro Val Lys Asp Leu Leu Lys Lys Asn Gln Met Glu Asn Cys Gln
```

-continued 785 790 795 800

Thr Leu Val Asp Lys Phe Met Lys Leu Asp Leu Glu Asp Pro Asn Leu
805 810 815

Asp Leu Asn Val Phe Met Ser Gln Glu Val Leu Pro Ala Ala Thr Ser
820 825 830

Ile Leu

<210> SEQ ID NO 30
<211> LENGTH: 2734
<212> TYPE: DNA
<213> ORGANISM: Homo sapiens
<220> FEATURE:
<223> OTHER INFORMATION: coding region of hMSH5 cDNA from residue 102-2606

<400> SEQUENCE: 30
cagaaacctc atacttctcg ggtcagggaa ggtttgggag ggcgtggcgg tcggtcagcg 60
gggcgttctc ccacctgtag cgactcagag cctccaagct catggcctcc ttaggagcga 120
acccaaggag gacaccgcag ggaccgagac ctggggcggc ctcctccggc ttccccagcc 180
cggccccagt gccgggcccc agggaggccg aggaggagga agtcgaggag gaggaggagc 240
tggccgagat ccatctgtgt gtgctgtgga attcaggata cttgggcatt gcctactatg 300
atactagtga ctccactatc cacttcatgc cagatgcccc agaccacgag agcctcaagc 360
ttctccagag agttctggat gagatcaatc cccagtctgt tgttacgagt gccaaacagg 420
atgagaatat gactcgattt ctgggaaagc ttgcctccca ggagcacaga gagcctaaaa 480
gacctgaaat catatttttg ccaagtgtgg attttggtct ggagataagc aaacaacgcc 540
tcctttctgg aaactactcc ttcatcccag acgccatgac tgccactgag aaaatcctct 600
tcctctcttc cattattccc tttgactgcc tcctcacagt tcgagcactt ggagggctgc 660
tgaagttcct gggtcgaaga agaatcgggg ttgaactgga agactataat gtcagcgtcc 720
ccatcctggg ctttaagaaa tttatgttga ctcatctggt gaacatagat caagacactt 780
acagtgttct acagattttt aagagtgagt ctcacccctc agtgtacaaa gtggccagtg 840
gactgaagga ggggctcagc ctctttggaa tcctcaacag atgccactgt aagtggggag 900
agaagctgct caggctatgg ttcacacgtc cgactcatga cctgggggag ctcagttctc 960
gtctggacgt cattcagttt tttctgctgc cccagaatct ggacatggct cagatgctgc 1020
atcggctcct gggtcacatc aagaacgtgc ctctgattct gaaacgcatg aagttgtccc 1080
acaccaaggt cagcgactgg caggttctct acaagactgt gtacagtgcc ctgggcctga 1140
gggatgcctg ccgctccctg ccgcagtcca tccagctctt tcgggacatt gcccaagagt 1200
tctctgatga cctgcaccat atcgccagcc tcattgggaa agtagtggac tttgagggca 1260
gccttgctga aaatcgcttc acagtcctcc ccaacataga tcctgaaatt gatgagaaaa 1320
agcgaagact gatgggactt cccagtttcc ttactgaggt tgcccgcaag gagctggaga 1380
atctggactc ccgtattcct tcatgcagtg tcatctacat ccctctgatt ggcttccttc 1440
tttctattcc ccgcctgcct tccatggtag aggccagtga ctttgagatt aatggactgg 1500
acttcatgtt tctctcagag gagaagctgc actatcgtag tgcccgaacc aaggagctgg 1560
atgcattgct gggggacctg cactgcgaga tccgggacca ggagacgctg ctgatgtacc 1620
agctacagtg ccaggtgctg gcacgagcag ctgtcttaac ccgagtattg gaccttgcct 1680
cccgcctgga cgtcctgctg gctcttgcca gtgctgcccg ggactatggc tactcaaggc 1740

-continued

```
cgcgttactc cccacaagtc cttggggtac gaatccagaa tggcagacat cctctgatgg   1800

aactctgtgc ccgaaccttt gtgcccaact ccacagaatg tggtggggac aaagggaggg   1860

tcaaagtcat cactggaccc aactcatcag ggaagagcat atacctcaaa caggtaggct   1920

tgatcacatt catggccctg gtaggcagct ttgtgccagc agaggaggcc gaaattgggg   1980

cagtagacgc catcttcaca cgaattcata gctgcgaatc catctccctt ggcctctcca   2040

ccttcatgat cgacctcaac caggtggcga aagcagtgaa caatgccact gcacagtcgc   2100

tggtccttat tgatgaattt ggaaagggaa ccaacacggt ggatgggctc gcgcttctgg   2160

ccgctgtgct ccgacactgg ctggcacgtg gacccacatg cccccacatc tttgtggcca   2220

ccaactttct gagccttgtt cagctacaac tgctgccaca agggcccctg gtgcagtatt   2280

tgaccatgga gacctgtgag gatggcaacg atcttgtctt cttctatcag gtttgcgaag   2340

gtgttgcgaa ggccagccat gcctcccaca cagctgccca ggctgggctt cctgacaagc   2400

ttgtggctcg tggcaaggag gtctcagact tgatccgcag tggaaaaccc atcaagcctg   2460

tcaaggattt gctaaagaag aaccaaatgg aaaattgcca gacattagtg gataagttta   2520

tgaaactgga tttggaagat cctaacctgg acttgaacgt tttcatgagc caggaagtgc   2580

tgcctgctgc caccagcatc ctctgagagt ccttccagtg tcctccccag cctcctgaga   2640

ctccggtggg ctgccatgcc ctctttgttt ccttatctcc ctcagacgca gagtttttag   2700

tttctcacaa ttctaatgta ataatatatc ttaa                               2734


<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence:  hMSH5
      Primers

<400> SEQUENCE: 31

acgccatctt cacacgaat                                                   19


<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence:  hMSH5
      Primers

<400> SEQUENCE: 32

tgcagtggca ttgttcact                                                   19


<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:  hMSH4
      Primers

<400> SEQUENCE: 33

ggaaggtttg ggaggatgct gagg                                             24


<210> SEQ ID NO 34
<211> LENGTH: 22
<212> TYPE: DNA
<213> ORGANISM: Artificial Sequence
```

-continued

```
<220> FEATURE:
<223> OTHER INFORMATION: Description of Artificial Sequence:  hMSH4
      Primers

<400> SEQUENCE: 34

attgtgatta ttcttcagtc tt                                          22


<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence:  hMSH4
      Primers

<400> SEQUENCE: 35

atctcgagat gctgaggcct gag                                         23


<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence:  hMSH4
      Primers

<400> SEQUENCE: 36

gcgctagctt attcttcagt cttttc                                      26
```